US010907160B2

(12) United States Patent
Zhao et al.

(10) Patent No.: US 10,907,160 B2
(45) Date of Patent: Feb. 2, 2021

(54) METHODS FOR REDUCING LRRK2 EXPRESSION

(71) Applicant: Ionis Pharmaceuticals, Inc., Carlsbad, CA (US)

(72) Inventors: Hien Thuy Zhao, San Diego, CA (US); Holly Kordasiewicz, San Diego, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/063,903

(22) PCT Filed: Jan. 5, 2017

(86) PCT No.: PCT/US2017/012374
§ 371 (c)(1),
(2) Date: Jun. 19, 2018

(87) PCT Pub. No.: WO2017/120365
PCT Pub. Date: Jul. 13, 2017

(65) Prior Publication Data
US 2018/0362988 A1 Dec. 20, 2018

Related U.S. Application Data

(60) Provisional application No. 62/424,346, filed on Nov. 18, 2016, provisional application No. 62/275,121, filed on Jan. 5, 2016.

(51) Int. Cl.
*C12N 15/113* (2010.01)
*A61K 31/712* (2006.01)
*A61K 31/7125* (2006.01)
*A61K 31/7115* (2006.01)
*C12N 9/12* (2006.01)
*A61P 25/16* (2006.01)

(52) U.S. Cl.
CPC ........ *C12N 15/1137* (2013.01); *A61K 31/712* (2013.01); *A61K 31/7115* (2013.01); *A61K 31/7125* (2013.01); *A61P 25/16* (2018.01); *C12N 9/12* (2013.01); *C12N 2310/11* (2013.01); *C12N 2310/315* (2013.01); *C12N 2310/3231* (2013.01); *C12N 2310/3341* (2013.01); *C12N 2310/341* (2013.01); *C12N 2310/346* (2013.01); *C12Y 207/11001* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,185,444 A | 12/1993 | Summerton et al. |
| 5,276,019 A | 1/1994 | Cohen et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |

(Continued)

FOREIGN PATENT DOCUMENTS

| | | |
|---|---|---|
| WO | WO 2004/094636 | 11/2004 |
| WO | WO 2006/045392 | 5/2006 |
| WO | WO 2007/124096 | 11/2007 |
| WO | WO 2008/091799 | 7/2008 |
| WO | WO 2009/099991 | 8/2009 |

(Continued)

OTHER PUBLICATIONS

Sibley et al., "Identification of allele-specific RNAi effectors targeting genetic forms of Parkinson's disease" PLoS One (2011) 6(10): e26194.

(Continued)

*Primary Examiner* — Sean McGarry
(74) *Attorney, Agent, or Firm* — McNeill Baur PLLC

(57) ABSTRACT

Provided herein are methods for decreasing LRRK2 mRNA expression. Such methods are useful to ameliorate LRRK2 associated diseases. Such LRRK2 associated diseases include Parkinson's Disease, including non-LRRK2 mediated Parkinson's Disease.

48 Claims, No Drawings

Specification includes a Sequence Listing.

(56) References Cited

U.S. PATENT DOCUMENTS

| | | |
|---|---|---|
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,300,319 B1 | 10/2001 | Manoharan |
| 6,426,220 B1 | 7/2002 | Bennett et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,660,720 B2 | 12/2003 | Manoharan |
| 6,770,748 B2 | 8/2004 | Imanishi et al. |
| 7,015,315 B1 | 3/2006 | Cook et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,029,986 B2 | 10/2011 | Meitinger et al. |
| 8,030,467 B2 | 10/2011 | Seth et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,187,811 B2 | 5/2012 | Ericksson et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,440,803 B2 | 5/2013 | Swayze |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,669,048 B2 | 3/2014 | Reijo Pera et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 9,840,710 B2 | 12/2017 | Hastings et al. |
| 2001/0053519 A1 | 12/2001 | Fodor et al. |
| 2003/0158403 A1 | 8/2003 | Manoharan et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2005/0130923 A1 | 6/2005 | Bhat et al. |
| 2006/0148740 A1 | 7/2006 | Platenburg |
| 2007/0031844 A1 | 2/2007 | Khvorova et al. |
| 2008/0039618 A1 | 2/2008 | Allerson et al. |
| 2010/0190837 A1 | 7/2010 | Migawa et al. |
| 2010/0197762 A1 | 8/2010 | Swayze et al. |
| 2012/0135941 A1 | 5/2012 | Collard et al. |
| 2013/0130378 A1 | 5/2013 | Manoharan et al. |
| 2014/0107330 A1 | 4/2014 | Freier et al. |
| 2014/0128322 A1 | 5/2014 | Chen et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |

(56) References Cited

U.S. PATENT DOCUMENTS

| | | |
|---|---|---|
| 2015/0267195 A1 | 9/2015 | Seth et al. |
| 2015/0275212 A1 | 10/2015 | Albaek et al. |
| 2012/0052487 A9 | 11/2015 | Khvorova et al. |
| 2017/0137826 A1* | 5/2017 | Hastings ............ C12N 15/1137 |
| 2018/0362988 A1 | 12/2018 | Zhao et al. |

FOREIGN PATENT DOCUMENTS

| | | |
|---|---|---|
| WO | WO 2011/114106 | 9/2011 |
| WO | WO 2013/173635 | 11/2013 |
| WO | WO 2016/097212 | 6/2016 |
| WO | WO 2012/131365 | 3/2017 |
| WO | WO 2017/087282 | 5/2017 |
| WO | WO 2017/120365 | 7/2017 |
| WO | WO 2019/118325 | 6/2019 |
| WO | WO 2020/006267 | 1/2020 |

OTHER PUBLICATIONS

Sibley et al., "Silencing of Parkinson's disease-associated genes with artificial mirtron mimics of miR-1224" Nucleic Acids Res. (2012) 40(19): 9863-9875.

Ynigo-Mojado et al., "Efficient allele-specific targeting of LRRK2 R1441 mutations mediated by RNAi" PLoS One (2011) 6: e21352.

Alegre-Abarrategui et al., LRRK2 regulates autophagic activity and localizes to specific membrane microdomains in a novel human genomic reporter cellular model: Hum Mol Genet (2009) 18(21): 4022-4034.

Branch et al., "A good antisense molecule is hard to find," TIBS (1998) 23:45-50.

Chan et al., "Rac1 protein rescues neurite retraction caused by G2019S leucine-rich repeat kinase 2 (LRRK2)." J Biol Chem (2011) 286(18):16104-9.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Crooke, ST., et al., "Antisense Drug Technology" Second Edition, CRC Press (2008) Chapters 1-28.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Genbank Acc. No. NM_198578.3.

Genbank Acc. No. NT_029419.11.

Gautschi et al., "Activity of a novel bcl-2/bcl-xLbispecific antisense oligonucleotide against tumors of diverse histologic origins" J. Natl. Cancer Inst. (2001) 93:463-471.

Herzig et al., "LRRK2 protein levels are determined by kinase function and are crucial for kidney and lung homeostasis in mice" Human Mol Gen (2011) 20(21): 4209-4223.

Herzig et al., "High LRRK2 Levels Fail to Induce or Exacerbate Neuronal Alpha-Synucleinopathy in Mouse Brain" PLoS One (2012) 7(5): 1-14.

Hinkle et al., "LRRK2 knockout mice have an intact dopaminergic system but display alterations in exploratory and motor co-ordination behaviors" Mol Neurodegener (2012) 7: 1-17.

International Search Report for PCT/US17/12374 dated Mar. 23, 2017.

Lloret et al, "Validation of LRRK2 as a Drug Target for Treatment of Parkinson's Disease Using Antisense Technology" Michael J. Fox Foundation Funded Grant Interim Progress Report, (2009) retreived from the internet on Sep. 11, 2018 (https://www.michaeljfox.org/foundation/grant-detail.php?grant_id=542).

Luk et al., "Pathological α-synuclein transmission initiates Parkinson-like neurodegeneration in nontransgenic mice" Science (2012) 338(6109): 949-953.

Maher et al., "Comparative hybrid arrest by tandem antisense oligodeoxyribonucleotides or oligodeoxyribonucleoside methylpbosphonates in a cell-free system" Nucl. Acid. Res. (1998) 16(8):3341-3358.

New England Biolabs 1998/1999 Catalog (cover page and pp. 121 and 284).

Nichols et al., "Substrate specificity and inhibitors of LRRK2, a protein kinase mutated in Parkinson's disease." Biochem J. (2009) 424(1):47-60.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.

Sheng et al., "Deletion of the WD40 Domain of LRRK2 in Zebrafish Causes Parkinsonism-Like Loss of Neurons and Loco-motive Defect" PloS Genetics (2010) 6(4):e1000914.

Tong et al., "Loss of leucine-rich repeat kinase 2 causes age-dependent bi-phasic alterations of the autophagy pathway" Mol Neurodegener (2012) 7: 1-16.

Tran et al., "Antisense oligonucleotides to LRRK2 ameliorate alpha-synuclein pathology and behavioral deficit induced by pre-formed alpha-synuclein fibrils." Abstract from Society for Neuro-science meeting Nov. 15, 2016, retreived from the internet Aug. 15, 2018 http://www.abstractsonline.com/pp8/index.html#!/4071/presentation/14652/.

Volpicelli-Daley et al, "LRRK2 Expression Augments α-Synuclein Sequestration into Inclusions in Neurons" J Neuroscience (2016) 36(28):7415-7427.

Volpicelli-Daley et al., "LRRK2 facilitates formation of alph-synuclein inclusions." abstract from Society for Neuroscience meeting, Nov. 15, 2016, retreived online Aug. 21, 2018 http://www.abstractsonline.com/pp8/index.html#!/4071/presentation/14651.

Volta et al., "Chronic and acute LRRK2 silencing has no long-term behavioral effects, whereas wild-type and mutant LRRK2 overexpression induce motor and cognitive deficits and altered regulation of dopamine release." Parkinsonism anRelat Disord (2015) 21(10):1156-63.

Woolf et al., "Specificity of antisense oligonucleotides in vivo" PNAS (1992) 89: 7305-7309.

Zhao et al., "Antisense oligonucleotides to LRRK2 ameliorate alpha-synuclein pathology and behavioral deficit induced by pre-formed alpha-sunuclein fibrils" Abstract from American Acadamy of Neurology meeting, Oct. 16, 2012, retreived from the internet Aug. 15, 2018: http://www.abstractsonline.com/pp8/#!/4046/presentation/8588.

Zhao et al., "Antisense Oligonucleotides to LRRK2 Ameliorate alpha-Synuclein Pathology and Behavioral Deficit Induced by Pre-Formed alpha-Synuclein Fibrils." Annals of Neurology (2017) 82(21): S56-S57.

Zhao et al., "Antisense Oligonucleotides to LRRK2 Ameliorate alpha-Synuclein Pathology and Behavioral Deficit Induced by Pre-Formed alpha-Synuclein Fibrils." 13th International Conference on Alzheimer's and Parkinson's diseases, abstract presented Apr. 1, 2017.

Zhao et al., "LRRK2 Antisense Oligonucleotides Ameliorate α-Synuclein Inclusion Formation in a Parkinson's Disease Mouse Model" Mol Ther Nucleic Acids (2017) 8:508-519.

International Search Report for PCT/US19/39558, dated Nov. 14, 2019, 13 pages.

Cho et al., "Leucine-rich repeat kinase 2 regulates Sec16A at ER exit sites to allow ER-Golgi export" EMBO J (2014) 33: 2314-2331.

Daher et al., "Abrogation of α-synuclein-mediated dopaminergic neurodegeneration in LRRK2-deficient rats" PNAS (2014) 111: 9289-9294.

Daher et al., "Leucine-rich Repeat Kinase 2 (LRRK2) Pharmacological Inhibition Abates α-synuclein Gene-induced Neurodegeneration" J Biol Chem (2015) 290: 19433-19444.

(56) References Cited

OTHER PUBLICATIONS

Guerreiro et al., "LRRK2 interactions with α-synuclein in Parkingson's disease brains and in cell models" J Mol Med (2013) 91: 513-522.
Atashrazm et al. "LRRK2 Inhibitors and Their Potential in the Treatment of Parkinson's Disease: Current Perspectives" Clin Pharmacol (2016) 177-189.

* cited by examiner

SEQUENCE LISTING

```
<160> NUMBER OF SEQ ID NOS: 18

<210> SEQ ID NO 1
<211> LENGTH: 8231
<212> TYPE: DNA
<213> ORGANISM: Mus musculus

<400> SEQUENCE: 1
gagcagctct gagagcagga gccgtcccag ctcgccgcag tccccgccgg ctgcaccatg      60
gccagtggcg cctgtcaggg ctgcgaagag gaagaggagg aggaggctct gaagaagttg     120
atagtcaggc tgaataatgt ccaggaaggc aagcagatcg agacgttgct tcagctcctg     180
gaggacatgc tggtgttcac ctactcggac cgcgcctcca agttatttga agataaaaat     240
ttccacgtgc ctctgttgat tgtcctggac tcctacatga gagttgccag tgtacagcag     300
gcggggtggt cacttctgtg caaattaata gaagtctgtc cagggacatt gcaaagctta     360
ataggacccc aggatattgg aaatgattgg gaagtccttg gtattcaccg gctgattctt     420
aaaatgttaa ctgttcatca cgccaatgta aacctgtcaa tagttggact aaaagccttg     480
gatctcctcc tagattcagg taaactcacc ttgctgatac tggatgaaga atgtgatatt     540
ttcttgttaa tttttgatgc catgcacaga tattcagcca atgatgaagt ccaaaaactg     600
ggatgcaaag ctttacacgt gcttttttgag agagtttccg aggaacagct gactgagttt     660
gtggagaaca aagattacac gatactgctg agtacgttcg gcagcttcag aagggacaag     720
gagattgtgt accacgtact ttgctgcttg cattccctgg cggttacatg cagcaatgta     780
gaggtcctca tgagtgggaa tgtccggtgc tacaatcttg tggtggaggc catgaaagcc     840
ttccccacca atgaaaacat ccaagaggtg agctgctcct tgttccagaa gcttacatta     900 ggtaacttt tcaacatcct ggtgttgaac gaagtgcatg tctttgtggt gaaagcggtc     960
cgacagtatc ctgagaacgc agccttacag atctctgcac tcagctgttt agcactcctc    1020
actgagacta ttttcttaaa ccaagacttg gaggaaagaa gtgagactca agagcagagc    1080
gaagaggaag acagtgagaa gcttttctgg ctggaaccct gctataaagc cctggtgcgc    1140
catcgaaagg acaaacacgt gcaggaggct gcctgctggg cactaaataa cctccttatg    1200
taccagaaca gtttgcatga gaagatcgga gatgaagatg gccagttccc tgcgcacagg    1260
```

```
gaagtgatgc tgtctatgct gatgcactct tcttccaaag atgtcttcca agcagctgca    1320
catgctctgt ccactctctt ggaacaaaat gttaatttca ggaaaatcct gctggcaaaa    1380
ggagtatacc tgaatgtctt ggaattgatg cagaagcatg cccatgcgcc tgaggtggca    1440
gagagtggct gcaagatgct gagtcacctg tttgaaggaa gtaacccttc tctggataca    1500
atggcagcag tggtccctaa atactaaca gtgatgaaag cccacggaac gtctctgtca    1560
gtccagctgg aggcgctgcg agctatcttg catttcgttg tgccaggact attggaagaa    1620
tccagggagg actctcaatg cagaccaaat gtgctcagaa acagtgtttt caggactgac    1680
atccacaagc tggttctagt cgctctgaac aggttcattg ggaatcctgg gattcagaaa    1740
tgtggattga agtaatctc ttctctcgcg caccttcctg atgccacaga acattgtcc     1800
ctgcaaggag cagttgactc agtcctccac accttacaga tgtatccaga tgaccaagaa    1860
attcagtgtc tgggcttaca ccttatggga tgcttgatga caaagaagaa tttctgcata    1920
gggacagggc acctcctggc aaaaattctg gcttccactt tgcagcgctt taaagatgtt    1980
gctgaggtgc agactacagg attacagaca acctgtcaa tacttgagct gtcagtatct     2040
ttctccaagc tgctagtgca ctattccttt gatgtggtga tatttcatca gatgtcttcc    2100
agtgttgtag aacaaaagga tgagcagttc ctcaatctat gttgcaaatg ctttgcaaaa    2160
gtggccgtgg atgatgagct gaaaacacc atgctagaga gagcctgcga tcagaataac     2220
agcatcatgg ttgaatgttt gctcctcttg ggagctgatg ccaaccaagt gaaggggca     2280
acttctttaa tctatcaggt atgtgagaaa gagagcagtc ctaaattggt ggaactgttg    2340
cttaatggtg gttgtcgtga acaagatgta cggaaggccc tgaccgtaag catccaaaag    2400
ggcgacagcc aggtcatcag cttgctcctc aggaaacttg ccctggacct ggccaacaac    2460
agcatttgcc ttggaggatt tggcatagga aaaattgatc cttcttggct tggtcctttta    2520
tttccagata agtcatccaa tttaaggaag caaacaaaca caggatctgt cctagcgagg    2580
aaagtgctcc ggtatcagat gagaaacacc cttcaagaag gcgtggcctc aggcagtgac    2640
ggcaagtttt ctgaagacgc gctggcgaaa tttggagaat ggacctttat tcccgactct    2700
tctatggaca gtgtgtttgg ccagagcgat gatctggata gcgaaggcag cgagagctca    2760
tttctcgtga agaggaagtc caactcaatt agtgtagggg aagtttacag agatctagct    2820
ctgcagcgct gctcaccaaa tgctcagagg cattccaatt cgctgggtcc tgttttgac     2880
catgaagact tactgagacg aaaaagaaaa atactgtctt cagatgagtc tctcaggtcc    2940
tcaaggctgc cgtcccatat gaggcaatca gatagctctt cttccctggc ttctgagaga    3000
gaacacatca cgtcgttaga cctatctgcc aacgaactca agatattga tgctctgagc     3060
cagaagtgtt gcctcagtag ccacctggaa catctcacca aactggaact tcaccagaat    3120
tcactcacga gcttcccaca gcagctgtgt gagactctga agtgtttgat acacttggat    3180
ttgcacagta caaaattcac ctcatttccc tctttcgtgt tgaaaatgcc acgtatcacc    3240
aacctagatg cctctcgaaa tgacatcggg ccaacagtag ttttagaccc tgcgatgaag    3300
tgtccaagcc tcaaacagtt gaatctgtcc tataaccagc tctcttcaat cccagagaat    3360
cttgcccaag tggtggagaa acttgagcag ctcctactgg aaggaaataa atatccgggg    3420
atttgctctc ccctgagcct gaaggaactg aagattttaa atcttagtaa aaatcacatt    3480
ccatccctac ctggagattt tcttgaggct tgttcaaaag tcgagagttt cagtgctcgc    3540
atgaattttc ttgctgcaat gcctgcctta ccttcttcca taacgagctt aaaattgtct    3600
cagaactctt tcacgtgcat tccagaagcg attttcagtc ttccgcactt gcggtccttg    3660
```

```
gatatgagcc acaacaacat tgaatgtctg ccgggacctg cacattggaa gtctctgaac    3720
ttaagggaac tcattttag caagaatcag atcagcacct tagactttag tgagaaccca    3780
cacgtgtggt caagagtaga gaaactgcat ctctctcata ataaactgaa agagattcct    3840
ccagaaattg gctgccttga aaatctgacg tctctcgacg tcagttacaa cttggaactg    3900
aggtccttcc caaatgaaat ggggaagttg agcaagatat gggatcttcc cttggacgga    3960
ctgcatctga attttgactt taagcacgta ggatgcaagg ccaaagacat cataaggttt    4020
ctacaacaac gtctgaaaaa ggctgtaccc tacaaccgaa tgaagctcat gattgtggga    4080
aatacgggga gcgtaagac cactttactg caacaactca tgaaaatgaa gaaaccagaa    4140
cttggcatgc agggtgccac agtcggcata gacgtgcgag actggtccat ccaaatacgg    4200
ggcaaaagga gaaaggacct ggttctaaac gtgtgggatt ttgcaggtcg tgaggaattc    4260
tacagcactc accccccactt catgacccag agagccctct acctggctgt ctatgatctc    4320
agcaaggggc aggcagaggt ggacgccatg aagccctggc tcttcaatat caaggctcgt    4380
gcctcttctt ccccggtgat tctggtgggc acacatttgg atgtttctga tgagaagcag    4440
cggaaagcgt gcataagcaa aatcacgaag gaactcctaa ataagcgagg attccccacc    4500
atccgggact accactttgt gaatgccacc gaggagtcag atgcgctggc aaagcttcgg    4560
aaaaccatca taaatgagag ccttaatttc aagatccgag atcagcctgt ggttgggcag    4620
ctaattccag attgctacgt agaactggag aaaatcattt tatcagagcg gaaagctgtg    4680
ccgactgagt ttcctgtgat taaccggaaa cacctgttac agctcgtgaa cgaacatcag    4740
ctgcagctgg atgagaacga gctcccacac gccgttcact tcctaaatga gtcgggagtt    4800
cttctgcatt ttcaagaccc tgccctgcag ctaagtgacc tgtactttgt ggaacccaag    4860
tggctttgta aagtcatggc acagatcttg acagtgaagg tagacggctg tctgaaacat    4920
cctaagggca tcatttcccg gagagatgtg gaaaaattcc tttcaaagaa gaagcgattc    4980
ccgaagaact atatgatgca atactttaaa ctattagaaa aatttcagat cgcattgcca    5040
ataggggaag aatatcttct ggttccaagc agcttgtctg accacaggcc agtgatagag    5100 ctccccccact gtgagaactc tgagatcatc atccggctgt acgaaatgcc gtactttccc    5160
atgggatttt ggtcaagatt gattaaccga ttacttgaaa tctcacccct catgcttctc    5220
ggcagagaga gagcactacg ccctaacagg atgtattggc ggcaaggcat ctacttgaat    5280
tggtctccag aagcatactg tctggtaggc tctgaagtct tagacaatcg acctgagagt    5340
ttcttgaaaa tcacagttcc gtcttgtaga aaaggttgta ttcttctggg ccgagttgtg    5400
gatcatattg actcactcat ggaagaatgg tttcccgggt tactggagat tgacatttgt    5460
ggggaaggag aaactctgtt gaagaaatgg gcattgtaca gttttaatga tggtgaagaa    5520
catcagaaga tcttgcttga tgagttgatg aagaaggctg aagaaggaga cctgttaata    5580
aatccagacc aaccaaggct cactattcca atatcccaga ttgctccgga cttgatcttg    5640
gctgacctgc ctagaaatat catgttgaac aatgatgagt tggaatttga ggaagcacca    5700
gagtttctct taggcgatgg aagttttgga tccgtttatc gagctgccta cgaaggagag    5760
gaagtggctg tgaagatttt taataagcac acatctctta ggctgttaag acaagagttg    5820
gtggtccttt gtcaccttca ccaccccagc ctgatatcct tgctggcggc tggtattcgt    5880
cctcggatgt tggtaatgga gttggccctcc aaaggttcct tggatcgcct gctgcagcag    5940
gacaaagcca gcctcaccag aaccctccag cacaggatcg cgttgcatgt ggccgacggc    6000
```

```
ctgaggtatc tccactcagc catgattatt taccgtgacc tgaagcccca caatgtgctg    6060
cttttacccc tgtatcccaa tgctgccatc attgcgaaga ttgcggacta cgggatcgca    6120
cagtactgct gcaggatggg aataaagaca tcagagggca ccccagggtt ccgggcacct    6180
gaagttgcca gggggaatgt catttataac caacaggccg atgtttattc ttttggctta    6240
ctacttcacg atatttggac aactgggagt aggattatgg agggtttgag gttcccaaat    6300
gagtttgatg agttagccat acaagggaag ttgccagatc cagttaaaga atatggctgt    6360
gccccatggc ctatggttga aagttaatt acaaagtgtt tgaaagaaaa tcctcaagaa     6420
agacccactt ctgcccaggt ctttgacatt ttgaattcgg ctgaattaat ttgcctcatg    6480
cgacacattt taatacctaa gaacatcatt gttgaatgca tggttgccac gaatctcaat    6540
agcaagagtg cgactctctg gttgggatgt gggaacacag aaaaaggaca gctttcctta    6600
tttgacttaa acacggaaag atacagctat gaggaagttg ctgatagtag aatactgtgc    6660
ttggctttgg tgcatctcgc tgctgagaaa gagagctggg ttgtgtgcgg acacagtct    6720
ggggctctcc tggtcatcaa tgttgaagag gagacaaaga gacacaccct ggaaaagatg    6780
actgattctg tcacttgttt gcattgcaat tcccttgcca agcagagcaa gcaaagtaac    6840
tttcttttgg tgggaactgc tgatggtaac ttaatgtatat ttgaagataa agccgttaag    6900
tgtaaaggag ctgcccctt gaagacacta cacataggcg atgtcagtac gccctgatg     6960
tgcctgagcg agtccctgaa ttcatctgaa agacacatca catggggagg gtgtggcaca    7020
aaggtcttct ccttttccaa tgatttcacc attcagaaac tcatcgagac aaaaaccaac    7080
cagctgtttt cttacgcagc tttcagcgat tctaacatca tagcgctggc agtagacaca    7140
gccctgtata ttgccaagaa aaacagcccct gtcgtagagg tgtgggacaa gaaaacagaa    7200
aagctctgtg aattaataga ctgtgtgcac ttcttaaagg aggtgatggt aaaactaaac    7260
aaggaatcga acatcagct gtcctactct gggagggtga aggccctctg cctgcagaag    7320
aacacggctc tctggatcgg aactggagga ggccacatct tactcctgga tctttctact    7380
cggcgagtta tccgcaccat tcacaatttc tgtgattctg tgagagccat ggccacagca    7440
caattaggaa gccttaagaa tgtcatgctg gttttggggt acaagcggaa gagtacagag    7500
ggtatccaag aacaaaaaga gatacaatct tgtttgtcta tttgggacct caatcttcca    7560
cacgaggtgc aaaatttaga aaaacacatt gaagtaagaa cagaattagc tgataaaatg    7620
aggaaaacat ctgttgaata gaaagacatc aggcagtctc gatgttatat tgaataagac    7680
atcagacatc ctcgtcacta tattgaaaag gacatcagac atcctcgcca atatgttaga    7740
aaatgtactc ttcttttaa aatatatttt taaaatgttt acattgaaaa gagtatgcct    7800
attctttaca aagttcatat gtatatgaag gaatgtgtat gtcttatgtt taatttaata    7860
tatgtaaaaa tatttatcag taaatatgtt ttaaaaaact atttaattta gcattatatt    7920
ttctatactc cttaactaat ttgaagggat aaacaaagaa atctacaaa gcatttaatt    7980
tcagtattta tactaaaatt aataaaaata tcatgtttgt tttgctatgt attgtgatga    8040
taaagcctat tttaaattgt tgattaagac acagatgttg cttgattatc tatggactca    8100
gcggagtaga ataaaatatc tggtcaattt ccaagtaaga gactctttca tatcttgttt    8160
tcaagtgaat tatcatcatt aatgtaaact gtcatatttt cactaataaa gattttgtt     8220
agctcaggaa a                                                          8231

<210> SEQ ID NO 2
<211> LENGTH: 150001
```

```
<212> TYPE: DNA
<213> ORGANISM: Homo sapines

<400> SEQUENCE: 2
gtactttttc cttcttcaga aattgataga gaaaggctac tacatactct gaatggatgt      60
caattggaca tccaaaagga caagatggca attctcccat cttgtccttc ttcaaaagtg     120
tctagtctat actaggcctt ttgatcttgc tgaaatctat gtaaatcttg ttgagaattt     180
cactaatctt gcattgtttt ttattacttt gtagagaatt gacatatttt tgaatttagt     240
tttcccatta attaatgtga tattaatatt tattcatgcc ttttttaatgc cttttaacag    300 agttcaataa tttattcata aaggttttgt aaatatttgt taatttattt tcaaggtttc     360
cctttcattg tcatcataca cacacacaca cacaattgca ctttatgctt gtgcatcact     420
catgtttagg aacacatttt tttataatgt atgacattaa aaaatactta ttggtcattc     480
aaaatgaatt tccttttcaa aaccttagtt tattattttt tttcctggtc tatctgtggc     540
gtaataccct cctcccagtg atttgtaaga acttttgaaa gttgaaggca aattgtattt     600
catcatatgt atttcaaatt ttttcttcct gtttgccgtt tgacttctag tttcattatt     660
gggtattttt tctttgactg cagaaaattt aaatttgatg gagtcacata tactacccctt   720 atgtgatttc ttttttgttt ttatgtttcc ttttttcaaga ttatataact attaatttat    780
attttatttt tgaagttatt tttatttaac tttttaatct atttgatgtt tgctgtaatt    840
agtaatgtca gttttatttt ttttcttttc aggaaattag ccaaatgttc tagcaccatt    900
ttattctcca ctgaaccctg cttccatcat aaattcatgc cttaatcttc attttcagtc   960
ttgttaacta cttgaagagt tgataaatct tggaatttca gtcaatcaat taaacatttt  1020
tgaaaactaa gagaatactt taccttaaca ctgcagtagt tcatgggaga atgctcccaa  1080
caaataattc atattttcac actgtctact cacagtctgg ccaatataga gtagataata  1140
aataggcaat agatggatga atgaattgtg gaaattagga gacatctttt aatttagatt  1200
tatttttctt tggaagggag gtaggtttta atttcttgca aggttgtaat tcagtagaac  1260
aggaagggag aaactaatgc agaggaacag aaggaatgca tgagatggag aatgcctaga  1320
aatgtttgag acattgatta agtcatcaga aatggaaaca agtttagaaa caacttagaa  1380
aataatacac tgtaggtctg ataaatattg taagattggg agttttttgt taaattatgg  1440
aaaattttat atagatacaa tagtagaaca gaccacatga acccatctca tattatcttc  1500
aacaattatc aattcaaaag ttgttatcgt tatctctatc tccacacatt tcatcttttc  1560
ctccaccact ggatgacttt gaaagaaatc ctaaccattt caactataaa tattttagca  1620
tgtctctgta aaagttaaag actctataac aacaagacat agacccaata tccaggttga  1680
gtaggagttt gctatcttac taatctaatg tattaacaaa gtctagagca ttcttattaa  1740
agtggtagag catgaagaac cttctacctg gagttaggag atttgctggg ttgaagtcct  1800
ggctctcaac ttcccacctg tgtgactcca gcaaagctct tcacttctca attccaaatc  1860
tcaatttcct cactagtgaa agaaggatac atagtagtag ttgtatccat ttcagaattg  1920
tcatcaggat tgaagtaaca gatgtgaaaa caaaactaaa attgtgaagt agtaacttcc  1980
agtccaatcc tcttctttgt aagtgatctt gaggacagac acatcacctg aaggatagat  2040
catctttgcc tagccttgtc tacaatgttc ttgctaggtt tcttttccta aaaacacatt  2100
acttaggtac ttaacagaac aaacaaacaa acaatcaaaa gacaaaaacca aaaaactttg  2160 gggttataga cacccatact cataagtatt tctgaatacc aagagaagag tatttaggtt  2220
```

```
tgcttctctc aacttttcac cttttcatttc atgtaccctg tcctttgtct cagctctaat    2280
agctctgaga gctgattact tttcgggtgt cccaagtatc aggatcctgc ctagtgcaac    2340
tcaaatttcc aaaagttaat ttagtggcct tttggtgacc agagcttcag ataactcaca    2400
gggaaacaat gtttatttcc tctcccacta acagtcacaa aaatcataa aaagagtag     2460 cgggggcagt tttgatggct aacccctctt tccatccttt gggggaaaat tgctcatctc    2520
cctataggtg gaactctaaa gacaatgtat tcctaaaagg ggccatctgg gcggtgtcct    2580
cttttcccag cgccctgatt tctattctta gatctggaga taggcggctt tcattttcc    2640 tgctcccagt tccagacct tccgtggggc cgcaggatcc ccggctggcg ggtcgcggag    2700
ggtggccggc cgggctgcgc actgcgcgcc tccgctgcgg ggctccgggc ctgtggactc    2760
agcggagtcc gctgagtcag tttcttcccg cgcgactccc ggccgcgccg ccgctgcggt    2820
ggaatctggt cccaggaggc ggcgtccgcc cggggtccgg tctaggcgtg cgtggggcc    2880 acggtcacgg tcatcccagc caggcccggc tccagcagcc ccacggccgc cgccagagtt    2940
ctgcgcggcc cgtcgcctcg gcggagcctc tggcaggccc ctgagctcgt ttttggggcc    3000
tgagtggggg aggaggaagc cgagcaggag ggctccggag agggagggca acgcggggcg    3060
gggagctgcc tccttcctca taacaggcg ggcgtgggcg ccgatggggc ccgcggggag    3120
cgctggctgc gggcggtgag ctgagctcgc ccccggggag ctgtggccgg cgcccctgcc    3180
ggttccctga gcagcggacg ttcatgctgg gagggcggcg ggttggaagc aggtgccacc    3240
atggctagtg gcagctgtca gggctgcgaa gaggacgagg aaactctgaa gaagttgata    3300
gtcaggctga acaatgtcca ggaaggaaaa cagatagaaa cgctggtcca atcctggag    3360 gatctgctgg tgttcacgta ctccgagcgc ggtaatcact tgaaaataaa ctgtgcttt    3420 attttgcaa acttctccc cctccttaca tttgcaaatt ttgtcctcct ccccttgacc    3480
ctgctcaaac ccggactctt aaggagccgc aaactcccat atccttttcct tagggcagaa    3540 agcagctgag aatttcagga aggtcttcac cttttttgact tttctcccg tttcagacta    3600 aaaaggagag ggggtgctgt ggattgtgac tttgcttctt ttccccaccc acttgttttc    3660
cagcctccaa gttatttcaa ggcaaaaata tccatgtgcc tctgttgatc gtcttggact    3720
cctatatgag agtcgcgagt gtgcagcagg taaaggcatt gttttcactt caactcattc    3780
tcccttctgt ttggaaggag acgttttact ggcaatgtta atatagccga gagttcttgg    3840
ttattcccaa aatttggctt gaggaacctc tgactgtgat tttaagatgg aatattgtt    3900 aaatcattac gcaatgtaaa cgggatgaag agccccagta tgtgttccct gagtgtcttt    3960
aagaagtaac tttataaaac caacagtatg gatggtggta gaaggaggat aaaaatgggt    4020
tcggttttag tctcgttatt ggcaagatga attcattagt gtttagactt gactattcca    4080
agtatcttcc caatacagag catgtcctag atgagaagat tatgaatagt ttggaaaagg    4140
ggaataatta atagtgataa aatgcaactt tgtcactagc aaactcttgt agagttcagc    4200 acttttaaa attcaaagat ttctagcctt tagttgtagt ataccttgta gtatctaaag    4260
aaagtgatgt cttatgagac cctcatagtt tgcaactgtt gtcatataaa atgcatgtag    4320
aagtgaaact tttacaatct gtaccatagg aaacccagaa atttgctatg tatcttggat    4380
ttttttttaa aggggccctt aaaaatggta attaagaatg atttacagtc aaaacaaaat    4440
tataggccaa ggtgataact tccttcggag cacttagaga tttggggaac tgaaatcagt    4500
tttgtcatct gcatgttaac tcatgcagag aaagagaatt ggactttgaa ctccttggag    4560
gtgcagtcag aaagccaatg tttcttaatg gttgagaggc ttgacagaca tgaggcatct    4620
```

```
caatctttaa agtggtgtgg gtctatcttt atcttgatgt ttatctctgt atctagctgt    4680
atctagtctg ggtgaaccat ctagcttctt tgatatgagg acatttacat ctggaagaaa    4740
tattttaatt tgttttcaac tgtgaaatat tttccatctg actattatag attttcacgc    4800
tgctatcaaa ccaaaccaag aaaagatgga ggcataataa agatgctgtt cttttaagac    4860
tcaaagtcgg aattttgcct gtggaatatg agtcactttt tgggcactgg cctattgtgc    4920
ttcctgctct gcacccacgt catcccttct tacttgtctc tgctttggtg ttcagaagtg    4980
cctgattctg gccaccttca ttccctagac tctgtacttg atagagtcac tcctgcttga    5040
tactgctcag gacagtcaga tcctgggtag gcgttttggt ctgcagggtc tagataaggc    5100
agtgctatac ttgacaaccc aggggagcct ggaacatact tcctaattct taattttaga    5160
aattgcccaa gcctgagcat acttgtccgg agtagttatg agtgtcactt agtatttctg    5220
cctagagagt accagaggca agtatgctg gaaaataagg aagagttttt ttaaaagtaa     5280
ttaattactt ttttggatat atcatagttg tatatatttt ggggatacat atgctatttg    5340
atacatgtat acaatgtgta atgttcaaat cagggtaact ggaatatccg tcacctcgaa    5400
catttttctt tgtgttggca acgttgcaat ttctttcttc tagctatttt aaaatatgca    5460
atgaattatt aaccataatt tccctgctat actattaaat attaacttaa ttgcttgtat    5520
ctaattatat ttttgtacac attaaccacc ttctctttat ccctccccat cctttcattt    5580
ccagtctctg gtaaccacca ttctactctc ttcctccatg agatccacct tttccgctcc    5640
tacatatgag tgagattatg caatatttta tttctgtacc tggcttattt aatttaacct    5700
aatgacctcc agtcccaccc atgctgttgc aaatgacagg atttcatttt ttatgactga    5760
ataatattcc attgtgtatg tataccacat tttcttttat ttttagttaa gtaattaatt    5820
tagagacagg gtctcactct gttgcccaga ctggagagca gtggtgtgat caaagctcac    5880
tgcaggcctg caatcctggg ctgaagtagt cctcctgcct cagcctccca ggtagctagg    5940
actataagca tgtgccacca tgctcagcta attttttttt ctttttttac tttttgtaga    6000
gatggagtct tgctatgttg cccaggttag tttcaaactc ctgacctcaa gtaatcctcc    6060
tgcctcggcc tccatatttt ctttgttaat ctgttgatag acatataagg tgattctgta    6120
ttttaactat tgtgaacagg gctgcaataa acatgggagt tcagatatat ctttgatata    6180
ctgatgttct tttttggat atatacccag cgatgagatt actggatcat atgaaaattc     6240
tcttttagt tttttaagat acctccatac tgtgtttcat catggctgtg ctactttata     6300
ttcccatcag cagtgtacca ccattcccct ttttctgcat ccttaccagc atttgttatt    6360
ttttgtcttt ttgataatag ccattctgcc tgtggtgaga taatatctca ttatggtttt    6420
gatttgcctc tccctaatga ttagtgaagt ttaggatttt tttttcatgt acctgttagc    6480
catttgtctg tcttcttttg agaaatgtct atttggatct tttgtccatt taaaaataag    6540
actttttttt tttttttttt tttgctaat tgagttttt tagttcctta tgtattctgg      6600
ttgttaatct tttgttgaat ggatattttg caaatatttt ctccctttct ttatgttgtc    6660
tcttcacttt gttaattatt ttctttgttg tgcagaagct ttttagcttg atataatccc    6720
atttgcctat ttttgttgta attgcctgtg cttttgaggt cctacccaa aaatcattgc     6780
acagaccaat gtcctgtagc atttccccag tgttttcttc tagtagttgc atattttcag    6840
gtctgagatg taagtcttta atccattttg aaatgatttg tgtatatggt gaaagctgtg    6900
gatctagttt ccttcttttg cacagccaat atttgattct cactgaaatc tcactgccct    6960
```

```
cctggaaata ttaccggatg ttttactgtc atagcgaagt gagagtaagc tgctcactga    7020
ggatcaaaga gcttgtgaca gacctaagac tcaagtcttc tcacaccttc aaaatctctt    7080
tccatcatac aatctactag ctgctgaatt cgcaagcttt ttgtgcaagc tagtaaaaag    7140
caaaatggtt tgatacaaat actgtggcca tgctaggtac aatgacatca atttaaatta    7200
tcattggtct taacaagggg atgtagaaag gggtctccta ctgacatttt aatactcact    7260
taaaagtagt ttttttcctt cagatttctt tatattatta gtataattac tgtaagtatc    7320
ctttactgct ttatatgttg aattagctgg aagtgccaaa agaaaaactc ttaatgataa    7380
atttaaggta ttaaggtaaa tttctccttc atttaatta atagtaattc ttaattacta    7440
tttaaaataa agattaaggt ttgtttctag atgccattta acatgatatt ccagactgcc    7500
agttttattt tcaaagtttg tttcatattt tattaatgtt tcttcataaa tgacagtctt    7560
tagaaaattg acggttaagc taggtgcttt atattttct tttcctgcct atcttttcac    7620
tgtgctccta aattttacat ctctttattc tcaagggttc aacctttgaa gaaggggagc    7680
aaaataaatg aaagtggcta aaatttttc tttaacccct agactctttc ctgttgtgca    7740
ttaattacat gcttgagttt ttagaataat tataataaag taaaactacc aatttaattg    7800
tattgtaact gtgcaagatg ggaaccttct ctcttagaga gataagcttt taattgaata    7860
gattaatgga tcaattgtta cctctgcttt gctgccagag attctattta atcacagaag    7920
ttccatgtag tgctggagag ctcagttgcc tgaatctttt tgcaaagcgt ttactgatac    7980
tgttgcttca ccaaccaaaa caaacaggtt ttttccttga gtcagctttg taggtacaga    8040
gatgagtttg gcatcctatg tgactttttt tttttttttt ttttttttt ttaccaccag    8100
aagctgttca gaatgttatt ttcttaaata gttcggaaaa aagtcttgat gtattctatg    8160
aaagcacaaa aatagtcagt ttctatgaca gctggattgt caacgtctgt tcagcttacg    8220
tggaggagga tgtcctactt gagtagtata ggtagaaata gctatcagaa attgccgcct    8280
ttgaaagcaa tttgaaatta tgtaaaagga agtaatgaca aaataaagca atttatgttt    8340
aatctggaaa agatccaaaa gtaatattgt aaagagatct tgagtaatca tttttatctt    8400
cctaaaatag ccgttgttta ctcccgtaag cgagtaagaa acttgtgcca ttattcctta    8460
ttgggtgcat atagatttct caccttgtca ttcaactcct tgcaatattc aactttactt    8520
atgcatccag cctatcccca aaatagcctc ttccctgtag cagcttcctt atcatgtagc    8580
agcctactct cctcaccgct catccgttct tatacaatct ggcttaagct ctacctcttc    8640
atattatatt cttctctgag taatttcaac tcacactgag tcttactttc agtatttcta    8700
ttatattggt atttattaca catcacactt agatacttt ccattagtct ctagagggta    8760
catatatgca ctttctcttt ttttttttt ttttgaccat gtcaagtata gttctatagt    8820
ataatagaat gaattggaga tcctttacat ttagagaggg aggagtctac agtaggaaga    8880
ataggttaat tttcatctcc ggtttgaaat caggactttc aattttttt tcagaggtaa    8940
agagcaactt agtcaagttg gcatcttgta aacagactga gtgaagatat acttaaaatg    9000
catctataat ttcatatttt atttcgaaat gtgaaagagc ctactagggg tgtctgtgat    9060
ctctagacct tatcaattca ttctagagaa atctggaggg agccattgag gagttctacc    9120
tcctgtctat tttatagagc tctttctctt tttctcctat cagatgtaga ttcaattgct    9180
aaaaatgcca cgtttcttgc ctctattatt ctagcttcat tacttgggga gcagccattc    9240
tgataactta cattttgcta ctaaaatctc caacttcacc taatccttca ttataagcca    9300
cttcatttt tcctataatt aaaattttaa atatgtggag gaaattctgt caggtagata    9360
```

```
tgacttaaaa cctactaagg gccaggtgca gaggctcacg cctgtaatcc cagcactttg    9420
agaggccaag tcaggaggat tgcttgagcc caggagcttg agaccagcct gggcaacaga    9480
gcgagacccc tgtcttcaca aaaaaaaaaa aaaaaaaatt agctgggtgt ggtggcacat    9540
acctgtagtc ccagctactt gggaggctga agtgggtgga tcacctaagg acaggagttc    9600
taggctgcag tgatctatga ttgcaccatt gcactccagc ctgggtgaca gagtgagacc    9660
ctatctcaaa aacaaaaaca aaccaaaaa aaaaaaaaa acaagaaaaa aaaagtacta      9720
aggatctggt atagccattc ttgcacttaa taatcttggt acaacctcta aaactatttt    9780
ttatagttta ttttattttg ccttatttag acaattggca tgtctatgtt cttcataatt    9840
tagaaattat atgtatttat atatataaat tatatatatt atatattatg tataaattaa    9900
attatatata tatataatat atatatattt gaaatggatt cttgctctgt catccaggct    9960
agagtgcagt ggcacaatct tggctcactg caccctctgc ctcctgggtt caagcgattc   10020
tccttcctca gcctcccgag tagctgagat tacaggcgcc catcaccatg cctggctaat   10080
ttttgtattt ttagtagaga ctgggtttca ccatcttggc cacattggtc tcaaactgcc   10140
ggctgaaatg ttgtattttt tgtatgtctt tctggtatga ttttggaga aaggtgtatc    10200 ctaagaatac ggcttgcttt tgtttctggg taagcatttt agggtatcat tttgttgtat   10260
aaccattgtt tacaagtgag ataagcatct attccactaa gattgaagag attcatgttt   10320
gactgagtat gctctattaa cattctttaa aacatgtgaa tatatgtctt tcttgttttc   10380
aggtgggttg gtcacttctg tgcaaattaa tagaagtctg tccaggtaca atgcaaagct   10440
taatgggacc ccaggatgtt ggaaatgatt gggaagtcct tggtgttcac cagtaagtat   10500
gatagatatg taaaacaaat ggccttgagt atttatttgt acacatgaca accttcccct   10560
gatacactgt gtttgcaatc caaggctact cctgtggaat tctttaaaat acagatatttt  10620 ttccttgagt caatgattta catttataga gagctttaaa ctcagaagtt tgatttagaa   10680
agcaaacatt taaggtaaca tgtcagaagt tattatttta ataatataat catataatta   10740
taaaactggt taagttgtag attttttgatg agtacttttg aattcaaacc atgaagagat  10800
tttggctttt aataatagaa tcgatacaaa ccactagttc ttaaaaaaat gggaactgag   10860
aaaagttagt tctgtaagta gtaatttgaa agttgatgtt ctactgtctt taaatagtac   10920
atttatatat atattcctat atatacagta agtttaaact atggctttca gaaagagtta   10980
agaaagagga aattaacttt cagcacatct gtagccaaat cttgatagta attttaccag   11040
ctatgttttt gcagtttgca gcataatggc ttcttagatg agactacttc cttagccatc   11100
attaattaag aaaatatttt ctcaagaaga atgtgtttcc aggaaaatac attttggata   11160
gctttgtttc ttgacagtta aaaaatatct tctaagctac tgaggaggct gaggaaggag   11220
aatcacttga acctgggagg cggaggttgc agtgagcgga ggttgcagtg agccgagatt   11280
gcaccactgc actccagcct gggtgacaga gcgacactct gtctcaaaaa caaacaaaca   11340 aacaacctt ttgtcattaa ctttaaatct ttttatacc taatatgact tttctttatc     11400
acagaaaagg aaattgtgaa tattttttgg cttccaatgg tatatggttt atgaaaattt   11460
aatttatgaa aaattttcag gtgtttgtat tgctgatcag tgtcaagtag tgctataaat   11520
ttagacaaat tagagctatg tgtttgtcca taagtgaaca tgtctgtgct tatacatttt   11580
cccctctttg acaaatgtgt tgctcttctt gttttcagta cataaagggt gtgttttgga   11640
aagagcatat ttacaattaa ttggagttct cgtcttcaat ctaatctctg taattctatg   11700
```

-continued

```
tatcagttct aaagtataca gcatttgatg aggaattact caaaatatac cagtaattag    11760
gaattgtaac tttaaatgtc ccttggtttg ggtgataatt tccaggaagt ccaaagatga    11820
gccagtctat aacctcaggg agtgtttggg aaactcatct agtcatattc ctgtacaaac    11880
caactgttca aattaaatta cataaaagtt tatgtaggaa atttcattca ctcactcact    11940
tactcattca ctcactttgt tcatccagtc attcatcttc tattcattga atgtttttga    12000
agcctgtcct ctgggtcaga aaccatgcag ttgtgaagaa gatagacaca ctgctgtctc    12060
cagtggagtg tattagatca ctcccagcaa aaattgattg taaaacagat ttctcttttt    12120
tcaaggcctt ttccctccaa agacttacca gtactgaaga aaaatttctt ccgtggtaat    12180
aaagtcagga attgtgggaa tggtataggg agaggtaggg gcagggtgat taggaggaag    12240
gctggcagag aatcgaagac tggcttcatt caggtcctcc aattgccaaa tggagattat    12300
gcaacgtttc ttgaatacat acaaaactct agatgtggcc agctcagtct tcttccaata    12360
atgtaaagcc aaacaatgct tgcaggaat agactagaga ttatattttg ggattaataa    12420
catagggatt aaaatcttat cttgaactaa ctaaacatta ttgatatgct aaattcactt    12480
tttttttttt tttttttttt ttttttttaga cagagtcttt ctctgttgcc aggctggcgt    12540
gcagtggcgt gatctcggct cactgtaacc tctgtgtccc gggttcaagt gattctcctg    12600
cctcagcctc tcgagtagct gggactgcag gagtacgcca ccacgcccag ctaattttg    12660
tattttagt agagacaggg tttcatcatg ttggccagga tggtcttgat ctattgacct    12720
catgatcccc ccgcctcggc gtcccaaagt gctgagatta caggcgtgag caacggccac    12780
cggcccacta cttttaata tatcattaat ttctcttta aaaacagtag caatcaataa    12840
tttaaatatt caaatgaatt cttaattta atacacaaac taacatcttt attatatctc    12900
tatattttaa tatatcaaca tgtctaagat aattataaa tttacatcat atataaaaat    12960
gggtttgctc tcgatgtata taaggcttca tgatattttg aatatggagt tgggtgaaaa    13020
tagtgaatct gaatatttga atttaatat ttattggaaa ataagtagtg cttttaactt    13080
tttaaatgag acacataata gtcccctgtt gatttttttt tattttttta actttattaa    13140
agtatagttg acaattaaaa attgtttata tttaaggtat acaattgatg atttgacatg    13200
tgtacattgt gaattattca ccacaatcaa gctaattaac attccctgtt agtttttata    13260
agcctggttc aggtttgtag aaagaaacaa acacacatgg ccaggcacgg tggctcacac    13320
ctataatccc agactttggg aggccaaggc aggaggatca cttgaaccca gaagtttaga    13380
ccagcctagg caaaatagca aaccctgtct ctccaaaaa gaatgaaaaa attagcctgg    13440
tgtggtggca tgtacctgta tccctagcaa ctcaggaggc tgaggcagga ggattgctca    13500
cttgagccca ggagtttgag gtttcagtga gctatgattg caccattgca ttccagcctg    13560
ggtgacacag caagaccctg tctctaaaag caggcaacaa aaacacatga gcttcactac    13620
agggaattaa atacaatgag agtaataaaa aataggtgag caaaaaaaat gcaaataagc    13680
aaacttttga gtatgatatt tcattcttat cttgatttct gttttaact ccagattgat    13740
tcttaaaatg ctaacagttc ataatgccag tgtaaacttg tcagtgattg gactgaagac    13800
cttgatctc ctcctaactt caggtaatat gtgtatatgt tttttgtgtt gattcaaatt    13860
aaaaaaaaag ttgataccat taagtaaatg tgtgtgtgtg tgttttttt ttttttttt    13920
tgaagatcag gattagggta gcttgattta aatgtcctaa aattgcatct gttttttagac    13980
ctagtgatgg gacagccata atataatcta aatatcagtt atttccaaaa ttctttctgt    14040
ttccatctct tctccttatc tcttttctct atactttgcc tctcaaaaat ctcattcaat    14100
```

```
acattggttt taaacattac cttatatatt atccccaaat ctctgttggt agtccgatgt   14160
ttgctcccaa aatctggacc tacatctcat attcccccag gttagtggtc attcctgccc   14220
ttgccattat tacttctttc tccctatata tctttaataa attttctata atatatgttc   14280
tggagtatgc cataatcgtt acattttgaa aacacatagt attacttctt gagtatttgc   14340
tagatgccag gcttcacaag taaaatgctt cacgtgcttt taaacacctg aatctgaaaa   14400
caccccttga gatagggatt ttatctcagt tttctaagtg acaaacactg aagtgcagag   14460
aagttgcttt ggccactaag aggtagaaac agggtctgat tctccatgtc aggttccttc   14520
cctgagaaaa ctttggcctg gtagataatg gacctgaaaa caaaaaatct tgaaatgatg   14580
caacagttgt gggcattgct gtgctggaca ctggctatta tataaggttc cgagaagaaa   14640
ggccgctcac agggagctaa tcttgaaggg ctgggaggag tttccttcca tgtagggag   14700 ggcttttag gttgagagaa gtatgggtgc agaggcctgg gaggatagca tgagagaggc   14760
tggacgtgtg attgggaagg tttgaattgt cctcatcagt cctgctaaga gatgtaaaga   14820
ccatgctgga gaaagaggaa gatgagagta tgagggaaaa acaagaaggt actcaacatt   14880
tcactacagc tttttatgac catgttgtat ggcatgcact aagagtcttt aaccatgatt   14940
taatttaacc tcacccttgg gaggtatttt tttttgacg gagattcatt ctccatttgg   15000
cgatggacag gaagatgagg gtttattaat atgaaaaatc taccaacact ggaatatatt   15060
gaagttagcc tcatacagta ctactactcc tattccagta ttattatttt tattgacaga   15120
atagatgctg tttgtgttaa gtttgggatt atgataggaa atgtttggta tagtaaaagg   15180
caagagtgtg acatgcagtt agtccaagta cgaagagata ccaaaaaaaa aatgtttagt   15240
gaggagcaga gtttagcata tttggagtga agacaatgtg cggaaggaaa ggagctgatg   15300
agatacatgt actatagtcg gttgtgtgaa aggtcttgtt tttcatacta aggatcatga   15360
gaagatctta gtagattcca gcaagggatt tgcaagacca catttgtgtt ttagaaatat   15420
aatgcaggca ataaaccagt tggatagaaa ttggggactg tagagcaatt aagcaactgt   15480
ttttgcattc tagatgagaa tgcaaaacac aataggaatg aaggtgcctt gttcaaaagg   15540
agttttgttc aaaaggaatc ttcaagatgt gtaggagata ttcttaaagg acttggtaat   15600
gaattgattt gttgcttgga tagaatgatga aagagaaag gagggtggaa gaaggaagat   15660
gacttaggag tttctcttgg gtagctagtg gattatggta tcattgatga agacaggaa   15720 caggagtagg ccaggtttgg ggtaactgtg gaatattcag atgttgtcta agaggcataa   15780 gaatgtatt cagatgtttg gggcaagttg tctaggctag aagtactgat tgagactcat   15840
gaaattatag taaagtgaac tgggagttta tctcatttat aaagatctag agcttgataa   15900
gtctaacatc tagggcagtt aagtagttta tcaacaaaca aacaaacaaa caacaagaa   15960 aaccatgggt ctacaaacca ttcacagtct tcatgtaaaa attaattcat gtaaaaatta   16020
acacattaaa tgttaaagca gctctttact cagagcatat tattctcttt aaaataggta   16080
aaatcacctt gctgatattg gatgaagaaa gtgatatttt catgttaatt tttgatgcca   16140
tgcactcatt tccagccaat gatgaagtcc agaaacttgg atgcaaagct ttacatgtgc   16200
tgtttgagag aggtatttta aaatgtcaaa ttccttaaag tatatataag aaaaaaggc   16260 ttatactggg aaaagtagaa cacagttata ataagaagaa ggtttctaaa atcctactat   16320
ttattaagaa gtgggagttg tctgtcaagg gtgaggaatg gggttaattc agaagtattg   16380
cttgttttgg tggggtgaat ttcattcgtg ggttataaat catgcccctg gagtagactt   16440
```

```
tcttcaattg cttaacaagg cataaggttt actttgaaaa ctggatgtgt gggtgctatg    16500
aaagaaaaaa taaaactgtg aagccaagca taggttacac tgggattatg atgttgagtc    16560
atcaccagaa atcatagaaa ttgcataaag agcctgaagg tttacaaagt gtccttcagg    16620
aaaaagacta atatgcattt catagcctgg ccctgagatt gataactgag attattatgt    16680
aattttagag ttggttggag tccttgttta gtctttccat tgaccttagg aggaagtggg    16740
tcacagcagt gaagtgagca tcctgcctga ggacacagag cttgtgacag tacagttcaa    16800
ttagcaatta ttttaagagc ccttttgta tcattatgag agccaactgt gctaggggtt    16860
tagataagaa tgatttatgt gggccctgtg tcagttatca gtttaccagt ctaatttctt    16920
gcagttccca gaatgggata gatcacctga taactgttga attccctgtc tcctcccaga    16980
aggattttaa acagcttata gataattata atacacaaga gtaaacaaaa tggatgagaa    17040
aataggtgaa gggacaataa tataaagcta gattaagttt actgtgtttc taaggtcctg    17100
catatttaca aaggggtggg ccagaaattt gtctgtttgc ttcctatctg acaaagaaaa    17160
gaggtaaata tcagtggtta caaagttcct taagataaaa gtaaacctat tattcaggag    17220
aagcaattgg tctcatggga gatctgagaa acatcttccc atgggttttc ctggatgaga    17280
caataaagga catacatttt gcaaggaata caaagtgtat tgcagcgaga gtgactctgt    17340
caaaagtcag aatagcatgg gcctggtacc cagctctttg ataatcatac accgtgaagt    17400
agaagatagt ttacagcgag tacgaaattc cttcaggctg tcatgtataa atgttctatc    17460
ttgcaactaa gctttcgatg acaattagga taaagtttga ggttctattg tcttgcaggg    17520
tctgtaatct tctgtgtgga aggttagggg cacattcttc ttcctggaag gagggctagc    17580
atcactttat caccatcgtt gtttagtcca tctaagacac tggaggtaga ccatagaatg    17640
ttacaaagaa gaatgttgct caatagaaaa accatcagtg ctgagagggt tatgactata    17700
aatgtagagt agaaaaattt ctgattttc caggagtatc aggttctcca ggactcaggg    17760
gtgactataa agttaatttt caaaatttga agtgtactgt tggaaactag accataaagt    17820
gagaaagttc catgatattc ttcacttgtt aggaaaactt aactgatttc acattatatt    17880
atagggacac tctggcataa aattaaaaaa aatgaatgtt gatcacttag agtgctgtgt    17940
tttctaacat atttctggcg ccattctcaa gctagataaa ctataatttt atacatgttt    18000
ttcaggttgt tgcccaataa caatgactcc aaatggaact tactggcttg atcaaatgac    18060
tttaattgtg aaaattaatg atttatattt ttgctgtctg atggaaaacc actaagacag    18120
agtatttcaa agtctgatta cttgccattt gctcaagttg acaactcttg aactgaaaca    18180
tttagccgag ctgcccttca gcagcctacc attaatgcct ccctttaaa tattgcaata    18240 tgtccagttc cagttggcca tctttattag tcactgtcag ttttctctag aatttcccaa    18300
atgaaattgt aaataatttt gttttctga gaactgcttg ctgactagca cttttacatt    18360
tcaaaacatg gagtacctaa cataggccga aacaaaatta tttgaatctc cgtagcttgt    18420
tttctcatta taacattctt aggaagggct gcttcacaga aatatatttt ttatttaagg    18480
agattacact tgatgtatct cacacaacta taatgaatat tgtaattttt gaataattaa    18540
actttcatat catctttaag cttattcagt attttgtctt tcattttaa gtctcagagg    18600 agcaactgac tgaatttgtt gagaacaaag attatatgat attgttaagt gcgttaacaa    18660
attttaaaga tgaagaggaa attgtgcttc atgtgctgca ttgtttacat tccctagcga    18720
ttccttgtaa gtagcattta aatgttattt attttttgta tctgaaaaat tacaatatat    18780
ctcattctga gtatatttta acaatatttt tattatttag aaacttgtgg atgctcaacc    18840
```

```
cattcattca tttattcatt taattaattt acattcactg acattatact gaagttggct   18900
gtgggcttgg tgctggagaa acaatcgtgg aaaatacaga tgtgttcctt accttttcag   18960
agcttgtagt acaatggggg acacagataa gtacagaggt gattacagtg gcagaagtga   19020
tggcagatgg cagaagtacc tagagttagg agatcaaata ggaagtgagg cagtgtctct   19080
tagcaaagat ttaataagtg gagcttcctg tgcatgaagg tgtgacctga agtgagaatg   19140
caggcaaagt ggcccaggca gtgggcatgg ttaatgtaaa gatgctggag caagagagag   19200
cagactgcct tcaagaagac aaaagtagct cagtaaaggt gtggggttat gagtgtgcgt   19260
gcatgcatgc gtgtgtgccg ctgtgcatgc acatccccaa atatcctatc cgtttgtgtt   19320
tcattgacag aggcaaggga gagcttgata agaggcagta aatgaggcca gagacatgga   19380
gtggagagca tgaagggcct aaaaagccac atgaaggagt ttgaatttta ttgtgactct   19440
tgattagcat tttaatgagg ctttgaaatt tagccacatt tttcaccaaa aatattaatc   19500
agaagaaatt aatttgatgt gtatgctacc aatgattgct attaggctaa ataatggtt    19560 catattctgt tttgttttgt attaatggtt catattctgt tttgttttgt aagtgaccat   19620
taacactttg tattttatgt attacttgtg tgggtttcta caggatatac atatgcattt   19680
atctagtgat attttcatcc tcacacatgt gaagttttga ggattagagt taaacaatgt   19740
acctggtatg taataagtgt tctaaaatca ctgacaggat tattagacaa tatgtatttt   19800
atatgtgtgt tgtatactat atgtaattgc atttatggtt tcagatatgg aaatcactgt   19860
gtcaatctga aggtgtgagc cttcggtgta ggcagagtaa acccaatgc ccttgtgaaa    19920 gaatgctttt ttttggtgat gtttataaaa tcacaatgtt ttcttatcca caggaaatta   19980
aacactggaa agtgggtggg gctgaacaat aatagagaaa ggccatggtt ttacatttct   20040
ctgagacatc actgccaaca aactgaatat gttttcatt atacttttc cttggctata     20100 tttattcatt tatttattta ttttgggctg gaggttttg gaatccattg ttttccaccc    20160
acattggaca taactccagt aaaaatgtgt tgattcataa tgcaaaagtc aagaaagtag   20220
cagctaaaaa ttaagaaatc aaaagttttt aaaacactga ttctaactga aaaacatttg   20280
cttttcagtc tttaagtcta ttgttctgag tcaaagcagt tcatttcctt acgttgttaa   20340 tttttttct atgtttaagc attgtaatat acttttgtg aaaacagttg attagttttg     20400
gttgtgccaa acaaatact aaaatgtttt gcaaacagcc ttttttaaa caaaaaaga      20460 acagttaaca tttgatgcag agatatacat gttttctcca tgtaggttca cacctcactt   20520
cctttattga ttaattgctt tttctggtag agtctttctt tcctttctgt tttacctgtg   20580
tttgtcccta agacttatat tttaatatta tgcctcctct ctttcgttct cccatctttt   20640
cttccaccta ttttggagcc ttcaggaagc ttgattttgc tgccttgtac attggttgcc   20700
cttctggaat ggaggaaaca ggtcatagct gattttaact gttccatctg gtgacatatt   20760
cttgattttc tttcttttgg ttggggaaaa aaaacaatg caaagtcat tctccaatgg     20820 ggttgagcct cgttaagaaa tagaccctcc acaatggttg aactagttta cagtcccacc   20880
aacagtgtaa aagtgttcct atttctccac atcaaaaaaa aaaaaggta agcaatataa    20940 catgagccat atctaatagg acttcagaaa ttatctatcc tatagttcca ggatgacgat   21000
gatgatggtt gtgataatga tgaagattgt gatgatagtt atatgggaga taaaacttta   21060
agcactttac atattaaatt ctataatatt caccacatct attaaaatat gttacattat   21120
tgtccctatt ttaccaacaa gaaaactgac caacaagatt aaacaacgtg actaagttca   21180
```

```
cacaacctgt aacagcagaa tctatgtcaa tcacaacaca attagcagct atttctgtgg   21240
caattttcaa taaagatgtg tctggaaaaa aaaaaaagaa atagaccctc caatttattt   21300
atctgaaaac ttatgaccaa tacattacat ttccagactt tcatttcag tacttttcct    21360 ttcattttca gtactaaaag tactctgaat ttttcctttt tttgatctta aggctttaag   21420
ccaagaaaca ggaataaagt aaattttcct taatgccaaa gattagtcct acaccccatt   21480
atgttattaa tgaacagcat agtattttt acagctactt aaagaacatg atgtttaaat    21540
ttggaaatgc agtcattatg ctgccatcta tttacagtct atataagacg tctttgtatg   21600
catatttgaa aggagaacat ggttacctta ttgataatta tgatctcttt aaattcaggc   21660
aataatgtgg aagtcctcat gagtggcaat gtcaggtgtt ataatattgt ggtggaagct   21720
atgaaagcat tccctatgag tgaaagaatt caagaagtga gttgctgttt gctccatagg   21780
cttacattag gtgagtttct tagttaatat gtcatcacac actgtatgat atacatatac   21840
atataaaaca tatatatgtt gcataataat ggataagtag catattgaca tactttgaat   21900
gaaaatattg taaaatccca gaaaaaataa attaaaacaa aaagaaaata ctgtaaatta   21960
ccaaactgtt ctgctgtgct tagatggact tttaaaagga gtgtcaaaaa tagatgtgta   22020
gaatgtaaaa aagtattat cttaatctta tttttataga tgtagttcta tagatgagtt    22080
tttttattgt tgaggctata tttaaaatat aattatgtaa gaattgatac atacaaaaat   22140
atgcataaca tatacaatat aaagcataat gcaaataact cactatccaa cttaaatgtt   22200
gtatattccc agtgggggaa gctaccctgg gcttcttcct gcccttgctt tctctataga   22260
ggttaacact atccagaatt ttgtgtttac aaatcttttg tttataaata tgatttacta   22320
cattttcatg tttctctaag caaaattgtt aatgtttgcc tgcttttgct tcatcaaaat   22380
gtaatcatac tgtatgttgt cttctgcaat tttcaaatat cagtgctatg attataagaa   22440
tcagaaatat ttttgcatgt ggttgcatgt agtattctat tatttggaaa taccacaatt   22500
tattttccca tttttctatc catggacatt tggattcttt cttattttat gctactacta   22560
tctgtgttaa aacagataac tgaaaagaa cagttaacat ttggtgcaga gatatacata    22620
ttttctccat atataaataa gggttaatat tttaaaaaat atttatttgc cattggtatg   22680
tccttctttg tgaaatatgc aatctgtcat ttatcaatat tgttcacagg atagtctgtc   22740
tttttaaaac cgattcatag attctggata ataatgtttt ggtggtaggt tatacgtatt   22800
gaaaatacct tcccttgaac atcacactct ggggactgtt gtggggtggg gggagggggg   22860
agggatagca ttgggagata tacctaatgc tagatgacga gttagtgggt gcagcgcacc   22920
aacatggcac atgtatacat atgtaactaa cctgaacatt gtacacatgt accctaaaac   22980
ttaaagtata ataataattt taaaaaaaag gagatgaaga ggtagctgca ggttgactga   23040
gcaagggtca ttgtctattt gaagtttcaa aggtatctct gaaaataaac acagttttt    23100 gcaagagtga aaaaaaaaa aaaagaaaa taccttccct tgacttgtag catgtctttt     23160
caccgtcttt atggtggctt ttgtgatata gttaaattta ataatcagtt cctttgtgat   23220
ttactctttt ttatgtatct tgtttaagaa atcttaatct gtcctttccc taagataata   23280
aatatattgt atattttatt ccaaatctta ctcgtttgtt aaactgttgc agtttgtttt   23340
tgtaaagaac ccaattcccc ctcttttttt cagtgtggag agctagttac catcacagca   23400
caatttatta gaggttcacc tgtttcccag tcatgtggta tataaatatg taaacatata   23460
tgcttatgtt tctgtccttg gcgttctgtt gcattaatct gatttgtctg aatcagtttt   23520
aaatctgatg ttaaatataa cactatttaa attaatagtt ctgtaagtcc tgatatctga   23580
```

```
aaagctaata ggtcaagtca ccatacattc tttttaggc acagcttgcc tttttcttg    23640 ggcctttact attccatgca aattacagga ttaacttgtc cagttccttg gaaaacactg    23700
ttgagatttt gactggaatt gcacaaaata tgtggatcat tttaagaaga actgacatct    23760
ttacattata atttcttcta tacatgtctt gcacatctta gttttgcta cgtatcttat     23820 tttttattat tattgtaaat ggtatttctt tttaaatcat attttgaac tgtgttttca     23880 taaagaaatg caaatgattt tttgtatatt gaactaacct accttctaa actcttcgtt     23940 aattctgaca atttgtttct aaatgcactt aagttctcta cctagcaatt atataatttg    24000
taaataatga cagtctgagt tcttcctttc tgcttcttat attctttatt tcatttcctt    24060
gtcttcttac atgagtcaga attattaata tagtgttaaa tagagccatt gatactagac    24120
atccttgtct tgctcttttt cctgattta aacagaatat tttaatatt ctcccatcca      24180 aaataatgca tcttacaagg gtttaaactt ttaaaaaaaa ttttgttaag aaattttatt   24240
ttatttcttc tttgcttttg ttttttcaat gtgggctttt aaatgtttgc ttttattttt    24300
acaatgtggg cttaaaaata ttaaaatatt taattttatc aaatatactt aaaatgtagt   24360
aagtcttttt tttccttttc attatgttaa tatgaagaaa tacatctaca ggttttctaa    24420
tactaagcta ctgtgcactt cctgataaat ttaacttggt catttattag atttttaaaa    24480
acacttctaa aaaatcttct ctgttttatt tcacatatac caggtgagtt ttggcagcct    24540 cttgttttt cttttttacc ctttctttt tgttaaaaac atcctttat ttatttaatg       24600 attaatacat ggctattttg tgttttgtat ctgataacta tatataaagt tctgggggagt   24660 ctaaaccaac tgcttctagg ctgactgcct gtcagttgcg gagccttgtt ttcttgtatg    24720
gttgtgagtt tctcttttat tgagcatcct gaggacttaa attaaagatg ctctttcaga    24780
ggtgtttgcc aggagtcaga gcacaggact gacctgggag cagtttagga tatgatccag    24840
gcttaatatg ggagactctg gttgagacct taccttgcag agagtctgaa actggtttgt    24900
tgaatgcagc gccaggattc atgctttccc acaagactac tctggcgttc aactcacagc    24960
tcttgtttca gcttcttttt gaactccctc tgccctcaa cacacacctt ggaaatttcc     25020
ttgatatttt tgtgaggaca acaatgcatt taaaagtgag agtggttgct gaataataag    25080
gaatgatcgt taactgttgg acattgattc tgatgacatt ttctcaaaag gataaccagg    25140 aatatttgt acaaaattag gattattata ataggcattt agttttttcat tgttacaaat    25200 tttgaggaaa atcattaatc atttgaaaaa actaattgac atgtctccat tgtagcaact    25260
tgtattttca cttctagtat catgattata tccctgtgt aatttggaaa ttgattttag    25320
cattaggaaa tttcctagtt tcagttaaaa tgaattttttt gtaagctgaa ttctattta    25380 catgcacaac tttagtttgt tatttcttc cttgacaagc atttattgaa tgttgttata    25440
tgactaaaac tgtaagatga taatgtttta atattttcac atttctttca tagcttccaa    25500
agtgtatata tatactcaca tacttcatat atatgaatct acttatatac tgtatataaa    25560
aatatgtata taaatatata cacattgtat ataaatgtgt atatatattt acacatgtat    25620
ataaatatac atacaaatgt atataaatat acatatttat acacagatgt atataaatat    25680
acatatttat acacagatgt atataaatat acatatttat acacagatgt atataaatat    25740
acatatttat acacagatgt atataaatat acaaatataa atatatacat ttatatataa    25800
atatacatat ttatacacag atgtatataa atatacaaat ataaatatat acatttatat    25860
ataaatatac atatttatac acagatgtat ataaatatac aaatataaat atatacattt    25920
```

-continued

```
atatataaat atatatattt tttgatacgt acaactatct tgggagatgg gatattgtta    25980
ttatttccac atttacagat gaggtcctgt ggttcatcaa tctttgtgtt ttattcaaga    26040
ttatgtaagc agtaagggat gaaatcaggc tgagaaccca aatttcttca tccctaaaca    26100
aagtatttct tctaaacatg gtatccattt actagtttat ctctatcagg tgacccttta    26160
ttcattattt ttcatgagaa ggttgtagtt gtacaaagtg gctgatatct gataatgttt    26220
taatctaatt caaagtcgat ttcttaaatc caggtgtcag agtagcacac tactgtacaa    26280
ttctctgttt catgttttac aatttaccac agtcaagtta caacttgcac atgttacatt    26340
aaaatgtgaa ttcaccttaa tttcttgaaa tgagccagaa gaagaagtgg ttttgttttg    26400
tgatcaggga aatgctactt gactgccaaa ttgtctagaa cagcacatta aagttgcttg    26460
attttatact gttaaaatta aataaaacat ggcaactgtc atgtcatatg taacttttgt    26520
attattctgt aactttttttt gaaaataaaa agtgatcaaa ttgatcttca ggtaaagaat    26580
ctttttttctc ttgattatct cttagtggat gatgatttgt tccatttaat gggtagagaa    26640
tttattgttg ctgttattgt ttcaaaagta gctgaatgaa actcttaact ttttcttcat    26700
agttaaaatt aaaacctcaa gtaaataaat atttaacgtt ttgccaaact atgtaatcta    26760
attatgggct taatgcattt aaaggctttg tataatttgc tacgtatttt cacacaagtt    26820
acctgaacat aagtccagtc ttcctgctgt tttctgagtc acacagtgat tcagtgaccg    26880
aacagctgtt ggcagtggtg tgggtataat agggaaaaga gactgatggg gacaacccaa    26940
gtttagacaa gctggtaaaa gtagaagaaa atcttcttga aaacactagt gatcactaag    27000
ggctgtggag aattttttgct tggtgggtga atgtggaaga ggcaacagca tgggaaggtg    27060
ttggtaaagg agctccatac ttgcttaaac tgccttttga ttgtgaggcc gttgatgaat    27120
atttagtttg ggcttaggt tttttatgat acaggatatt ttccatttct ggctttgtat    27180
ctcagagatc acttagttac acttatagat gaataggagt ttcaattcct tgttttagaa    27240
agaagcttgg taactgttag tgagttacaa ataagccaaa tagaagaagg tacatatttc    27300
tgcagtatca ggtaaagttt ttcctcataa ggatttagac tcttggatat catattaatt    27360
ctcagaagag tgggtataaa aaggtatggg acttcttcct ggggtgggtt ggaggtggtg    27420
aaatacctttt ttttttttttt ttctgagatc atcatagaca agatcaaata atggtaaaca    27480
tgccaatgaa ttttctaagc actattcctt taagtgaaag aagagtgttt cagtaaaatg    27540
atttaatatt gggtcttcca aaagatggat ttaagagttt caactttaaa agacagaaaa    27600
attaagttat tttacacaat gaatattgtc gtgccgtgtg tcacagacat gacatgagag    27660
ggaatcagag aacatacagt taatacaacg caaactagta tcattacttt tgctcaatca    27720
cttccattgt ctaagtaaga taattaaagg acagcataaa ataaaatttc aaaactttac    27780
tcaatcatat taagctattt taattaaagt aaatgtttta atgccattga atattcatca    27840
ccattcaaaa ttattgatgt aaatagtgtt atatgttaaa ggtaatttaa cttccatgga    27900
tgagaattca gctaatgttt cacttaactt ttaggtaatt ttttcaatat cctggtatta    27960
aacgaagtcc atgagtttgt ggtgaaagct gtgcagcagt acccagagaa tgcagcattg    28020
cagatctcag cgctcagctg tttggccctc ctcagtaagt aacttcacta aaaggggat    28080
tcttacagag gcatttgaca tcaaatatga acattgtaac aagagaatca tatgtacaga    28140
tggaagcatt caatgccttt tctgtcctgt gtagctcatt ttccagtaga ggatactttc    28200
aaggaaacta acagttgtga caaatataca catctcaatg tagagtttg ctttacatca    28260
ttcttgattt agctttgtca ttaagcagct aatctgtttt aaaaaaattt ttatttgtgc    28320
```

```
ctgggcatgg tggctcacgc ctgtaatctc agaactttgg gaggccgagg cgggtggatc   28380
acaaggtcag gagttcgaga ccagcctggc caacatggtg aaaccccatc tctactaaaa   28440
atataaaaat tagtctggca tggtggcggg cacctataat cccagctgct cgggaggccg   28500
aggcaggagt atcgcttgga actggagggt aggagttgaa gtgagctgag attgtgccac   28560
tgcactccag cctgggcaac aagaatgaaa ctccatctca aaaaaaataa tttatttgtg   28620
ttttaagttc tggtgtacac gtgcaggatg tgcaggtttt tcacataggt agacgtgtgc   28680
catggtggtt tgctatacct attaacccat cacctaggta ttaagcccag catgcattag   28740
ctattttttcc taatgctctc ccttctccag tcccatcccc taacaggccc cagtgtgtat   28800
tgtccctctc cctgtgttca tgtgttctca ttgttcagct cccatttata agtgagaaca   28860
cgcagtgtgt ggttttctct tcatgtgtta gttatctgag gataatggtt tccagctcca   28920
tccgtgtccc tgcaaaggac atgagataat tccttttttat ggctgcatag tattccatgg   28980
tatatatgta ccacatttttc tttatctagt ctatcattga tgggcatttg ggttgattcc   29040
atgtctttgc tcttgtgaat agtgctgtga tgaactaatc ttttcaaata atcctcctct   29100
cgtctattag gttttttttt tttttggtac cttcttcctc attttattat ttatctggat   29160
aggatggtag cattatgaga cgtataatat attaaaaatt atctttataa ttgaccaagg   29220
cttctcctaa agcacacctc attctgttgg taatatttca aaatatggac ttagagttgg   29280
tcaaactgtt aagtagataa tatatataat gttttttatat attttttcaat tttttttcaag   29340
ctgagactat tttcttaaat caagatttag aggaaaagaa tgagaatcaa gagaatgatg   29400
atgagggggga agaagataaa ttgttttggc tggaagcctg ttacaaagca ttaacgtggc   29460
atagaaagaa caagcacgtg caggtaggac tctcataaat attagagtta ttcaaaatta   29520
tgttttccag tcatttatat tttgacagat ttctttttttc tccctaatc caggaggccg   29580
catgctgggc actaaataat ctccttatgt accaaaacag tttacatgag aagattggag   29640
atgaagatgg ccagttagta gttttgattt tatatgatag aaaatttcag ttatatttta   29700
aatcaatacc tataaaatac cttaaccgta acttttattg ttagaaatat ttttgatata   29760
ggcatttagt tttagatgtt gctgcaaaat agtagtaggg atgtagtatt ttgatctcat   29820
caccttcagg agttagaaaa ggtagaatga gagttattat tgagagattt ggaatcaagg   29880
gtcatttggt aattcatgaa tcatggagaa agaatctttc tattttctgg ctgatcgttt   29940
taaaatgcca tattaattca tcttgggtga tagaaattgc agagccatct gtgatctttt   30000
cttctatggt gactagccag caggttgtca atatcagaaa ttagatttgg ttagagagct   30060
tcctatgatg agttcccaac tgatgtgaca gagttgacct gtcttctttc gagagggtta   30120
tttgaagctg tcatctctgg ataactcttt caataggagt gccattcaaa catcataaga   30180
ccggcactct ctcccaaaga tacaagctgt agcaaggagt tttgtgcata tcaggtttgt   30240
ttcatatccg tgagcctttg tgttttatgg caactgattg attatacttg tgctatttgc   30300
aatgggtatc ctctgggttt taaatagtga atgacttatt ttggaaacaa atagtagtat   30360
tctatgtctg aaatcttgac cgtctatttg tttaattatc tattgctgat aagaagggaa   30420
ttaataacac agatgctact taattaaata ttttcatttt gacaagaaac agtaattctt   30480
ttgaaaacta tgctaaattg gcatcttaat aatctcatgt tgagcaaggc ttttggagat   30540
tagggtaagg gagattcatg tcgcagttta taaatttcag ttcataggat acctattttt   30600
caatatccat aagataactt taaaataaat atattattaa aacaaagaaa atatatttac   30660
```

```
gttatacatc tttaaaacct accttgcttc tttacaattt tcagttttc ctctcttgtt      30720 tccattctct tctcctcact ttaccttttt cctcagcatc tctttacata tctgctgagc      30780 tttttattt ctctctgctg catatgcttt tgaaaaagca taaaaatact aatttgttag      30840
gatttaatta attcgagtct taaaaaatga actataattc actcttgtaa gtggaggtgg      30900
catgaaatat tgtttatatg ctcttaattg ttgttagaga tatttgataa tggcaagtga      30960
gaatttgaga tagttattta aaagattact actaacattt tgtttgaatt tttgaaagtt      31020
tcccagctca tagggaagtg atgctctcca tgctgatgca ttcttcatca aaggaagttt      31080
tccaggcatc tgcgaatgca ttgtcaactc tcttagaaca aaatggtaag cagtgggcca      31140
tgttttcaaa taaagggaaa cacattttg tggtatttt aattatagaa gctatatact      31200
gtgaaaaatt tacataattt ataaagctat atattgtgaa agatatctct atgtgtagag      31260
atgtattgac atatggatta tgaatatata ggtaaaagga tgaagaataa aataaacatt      31320
tgttgtatat ttttccggac ttctatgtgt aaactcacac atgacatata caaaatttta      31380
tgtattttgt agaaatggga tcatattata ctcttttata accaaatttt atttattctc      31440
ttttttatgt tgatacatgt gtattctcac attatcattt tatttttaat ttttaaatt      31500 aattttgtt tttagatatg gtctcactct gtcacctagg ctggagtgca gtaccatgat      31560
catggctcac tacaacctca aacttttgga ctcaggtgat gctcccacct cagcttcctg      31620
agtatctggg actacaggca tgcactgcca tacctggcta atttttgca gagatggtgt      31680 tttgccatat tgcccaggct ggtctcgaat tcctgggctc aagcaatcca tctgccttgg      31740
cctcccaagt gctgggatta caggcatgaa ccactgtgcc cggcccaaat tataattttt      31800
aatagctttg tagttttca gtgcttgcct gtattctgtt ttatgaacca atttcttact      31860
gatgaagttt tagtttgtgt ccagtgggat gtttctggaa cccatagtaa acaccagtga      31920
tcactttcct cctctgtttt cctttataca tggttcctat tattttcttg ggaaaatttc      31980
atagaaatgc aactgggtag agagctattc accatttaa aatctggtaa aattgtctat      32040
tataaatttc cacactatac tttttaaaa aatcgttctt taatgtaatt cttataaatc      32100
ttatagcttg gtataattat gaagagaaaa atggcttgta tccctttaga aagacatgag      32160
ttttaagatt atggttcagg ctgctcaaat ttcttccccc ataaacagga atactgccag      32220
aaatccttag gtgaaaactc atcataaagg cattgggact tggcagcttt tgcaggacat      32280
ttttagaggg caaaaatag agaaaaacac tgaaagtcag agacagagac cagtgtaagc      32340
atcagctttt aatagagaaa ctgggtaggg tggaaaaaaa ataaagcaac cacctcatgc      32400
atgtttcttt atattattat tgaagtcaaa taaagaggaa aatcatttct tcttcctctt      32460
cctccttttt catctcacct ctccaatggc actttaataa aacgcttgga gtggccaggg      32520
cactgacaga cagacagggg ctgctctcaa ggataatgag tcaaggggga aggagaggga      32580
atcgctgttc tcgaatctct cttattctac tgtgcagtta aagaggtctg acagggatt      32640 tcactcctga aaatgaggac tggactttgt ggcttctgtt ggggcacctt tagagtggag      32700
gtagactttt actatgtaca gacaacattg tgttggtgac atcattcata accacctgga      32760
aatctccttt gatatgcaaa tcaaacaacc ataactttgt gaaatttcga ctgcttccta      32820
ttgtggtgtc tgaggactgg ttacattcag agtccaccct gatgtctttg ttcagttttc      32880
tgctctttct agttccttac ttctttgttc ctgatcacct gtcaagtaaa atgtcctcag      32940
atccttttgt attgtctttg gagttctgcc ttaataaagc atgaagaact tgagtagctc      33000
gttcatcaac tttcttgggc aatttctcat tgaaagacac ttgggtgtct ttgggtgtgc      33060
```

```
agagctgagc atggctttat gttttagaa aaaatggcta cattggcagg cagaagaact   33120
gcgtccttgg aatcatggag gtcccaaggt tgcatacatt ttgtgtgaca tttttcctat   33180
tcaattaatt aactaatatt tattgagctc ccaagtgtgt agtgtctgta ggcacttggg   33240
atgcattcat taagtaaaaa tcccaggctc atggagttta aactgtagta gggaagataa   33300
taagattaac taaaatatgt aatatttgag gcagttaaga ataaaaaatg aagcaaggaa   33360
ggagaatatg atatgttaga catcagagga gatgaagttg tgaataggca gccaggaaag   33420
aaggtgacta ttgagtaaga cctgcagggc gtcgcatatt gttttttgcc tctgaaagca   33480
gttaatttcc tgttaaaatg gagtggatga gatcaagagt attacgtaga tagctggtaa   33540
atgcgatagt gtgtaaaatg ttctataaag tctaacgtga ctttatgatg aaatttcttc   33600
ttctaggttt attgcttgca attttcaaac cacacattgg gttactgtct aggatagtga   33660
ttcttaaagt gtggttcctg gaccagcagc atttgctggg ggaacttgat aaacagtgta   33720
aattcaagga ccccatacag accttctcaa tcacaaaccc tggagttgag acccagcaat   33780
ccatgtttta acaagctctc caggtgattc tgatgcacac taaagtttga gaaccactaa   33840
cccagtgtca tttttgtctt ttaaagtgtc ttcttggcta gaagctagcc actttgggaa   33900
aggttattac aacttctgat gtgatcaagc aaagtaacca actctttatt gtatcttaat   33960
atgtgatatt ctgaatgtgt ttaaaaggta tgagtttttc aggctctggc agtattttag   34020
aatgtgtatg tgatttctat ttatttccat gtttttgtcct atcttcttaa gatagactac   34080 ttatttaaa agcagtactt aagttaaaac ttttttatgtt tctttttctg ccactttcaa   34140
agtgttgaat cacagtgtgt aatgttggaa ctgatatttt tatagcggct tcaagacaat   34200
tgatatttat gtggaaactt gaagacagta ggtttatgtt tagtgaagga agtttattac   34260
aaagaggaaa attggccagt tgtggtggct cacgcctgta atcccagcac tttgggaggc   34320
caaggcagga ggattgcttg agctcaggag ttcaagacca ggctgggcaa catagtgaga   34380
tcccctctct acaaaatatt aacaaaaatt agccaggcat ggtggcacac ttgtagtccc   34440
tggtacttgg aggctgagac aggaggatca cttgaggcca ggaggttaag actgcagtga   34500
gctatgatca tgctactgca ctccagcctt ggcaacagag agagatgctg tcacaaaaag   34560
aaacaccaac aaaaaaagag gaaaattatt ccttaatcat tattgctgga atatagttac   34620
tttccacaaa tagtgaagtg ccagttgtaa agcatatcta tatgtttcct agactttggc   34680
attactttgt gaaaataact gtaattactt atgttctatg taaatgcttt ccattcattt   34740
gtatatgatg gcatatatag aaattataat gtttgtaaag tccactggga taaatggaca   34800
aagcagctga aggctgaaag caaccaagcc ttttacagcc ccttcattcc ccacactccc   34860
aaaaagctga gtgaatggtc gatacctcca catgcttata actcattccc agcccaccag   34920
tgtctagcat atctggttag tcttagcttt atataagtgc agttatttgt gaacttgttt   34980
taagtattgg aatacaattt aactttcatt cttattttgg agaccattat ttaaacagat   35040
ttcttttttc ctgcaaaaac actcttttca caatggacag agacacggtg attacattaa   35100
aaccatctac tctatgaata aaaatgttaa aaccaaaatc ccaacaaagg gttaataaag   35160
gcaaaaaaaa ttgaaaatga catgtgtttt aagaaataa acatgaatta tctttaagct   35220
gtcaatgaac tataaattat gtgtgctctt gtatatgctt tcctgtaaat ttggactata   35280
ttaatattct aaagcttatg gtaaaattat gaaaatatgc tttcatatct ataagtaaca   35340 tttaaaaaa tctcagttaa tttcagaaaa atactgttat caaaaggaat acacctgaat   35400
```

-continued

```
gttttggagt taatgcagaa gcatatacat tctcctgaag tggctgaaag tggctgtaaa    35460
atgctaaatc atcttttga aggaaggtaa tatagattca ttaacttgta cagaatatat    35520
catattgggc caggtagaat atcaatattt caagcatatt tctaacaatg aaaagaaaaa    35580
gaaaaacata agacacttga aaactgaagc atttttgcaat gtaatctcgt gtcactagta    35640
ccatagactt actttatctg aacactgaaa ggaatggcaa gattgtggaa acatgttgaa    35700
ggtttgcttt tgaacctgat gcttgatgtt gactatattt tgaaaagtgg taattgtata    35760
gcacatagca tacagcagtt tttctaatta ttgtgtgtgt gaaagttata aaagataaaa    35820
tcagtttatg gctaaatttt gctctttcac aacgaatata ttattccttc atctgaatga    35880
actttgtctt ctcttcctgc tctcaatcct tagttaggga aaattttaac tacatctagt    35940
ccaagtgcag agatgctaag attatatagc tggcggttag tggcacaaca gagaccatat    36000
cctttgatct atgtgtggat ggtggtgggg cagggtggga tgaggtgggg gtgaggggtg    36060
gtaggtgtgg gcagaactct catgtgtaaa aaaaataatt ggcacagaag ttgcagtgaa    36120
aactaatttt gttcctggtt ttgccactaa tttgagccaa ctgtttcatc tctaaaactt    36180
cacgttcctc attgataaag aggaatgata ataacaactt tgaaagttgt aagcttagaa    36240
tgtaaggatt aaataaatta atttttacaa agggattagg ataatgcctg ctgcatttta    36300
agcactcaac aaattgtgtc tattgttgtt atactgttac taagtgtgaa taaatgaagt    36360
gcatatagca tgaaatgtag cgtaactgca gacttgtaag aagtagggtt acactgtttt    36420
taacatcagt ctaactaatc tatgtttata tatctttcta agctgtattt ctcttattta    36480
agtgttgttt ttgaacactg agatgaaaag tttatcttaa atgttgattt taatggggcc    36540
ggaagtgtgc aaacctttac aaatgaggca aaaacacagc ggaataaact ccagtctagg    36600
attctgtaga ttctgggcaa ggcatttaat gtttctcgct gcatgctctt acgtaaaatg    36660
tgtacagttg cagccctgga gattccgcat tggctctgac agtgtgtctg cccctacaga    36720
actcatgtga gtcgagagac tgataagtaa acagattatt ataatacagt ctcagaatgc    36780
agtggcagta gtgtgtaaaa gacgcaatgg taagagtaga gtggactcag ctggggttac    36840
ccaaggaggg gaggctccaa tggagggatg tgtttaaact gggactttaa gttggaaaag    36900
aaggaatgta tctcagtgtc cacagaacca tgcaaagtga gaacatggtt ctgatatgca    36960
caagtttcag ttaacaagca aagcaaggat tgactgtatt aaagttcata gtacctactg    37020
cattctagtc aagtgacatt tgctcatatg taaaagaaag aatagcttaa atacctgaga    37080
gaaaccaaga ctgtaaaaca aattaaaaat aattaaaaat accttataag aagtccagtg    37140
atgttaatct ggaagaggaa ggttcgtgtg atgtaaagag gccttgtctt ggggtcagac    37200
aagtttgggt accagccttg tctctgtcac tttctagtga taagacctga atatttaacc    37260
tctatctgtc taagttcttc atgtagaaaa tggggataat aacacctacc tgctgggatt    37320
gttgttattg acccatcgta ggtcagaagg atgttgttag tttatgaag tgaaataatt    37380 cccggattac tatgaattct atcttatgag ttcaaagttt agacaattaa aattatgtat    37440
gctcatacta ctgatttcaa atgcattttc atatagtctt tcctgataaa atatattggt    37500
tctgccctcc tgtacttatt tcaatttggt gtttatacca ttgaatcaga tcagtctttc    37560
aataagcatg ccaattttat atccccagca acacttccct ggatataatg gcagcagtgg    37620 tcccccaaaat actaacagtt atgaaacgtc atgagacatc attaccagtg cagctggagg    37680
cgcttcgagc tattttacat tttatagtgc ctggtaagtt acatagttga ttgtgggaag    37740
agataacaat ttaaatggat ttttgatttt tcatgaaata gcaatattct aggcaaatat    37800
```

```
taaaagacta gtttctgtcg actaaatgta aatctttctg ttaaaccaaa aagaggttaa   37860
atatgatgca gaagagtcac ttagattaat ttttataaga aagcaatatg aattcagtaa   37920
tttatttata caaagtaact acaatgtaaa atgtggagct tttatttta aggagggtgt    37980 tcatctctga taattctttt ctattttgt tgccatgacc tgagttcaag cttttttct     38040 cttgtttgaa ttgtactatt agctaatttt catacctgtt ctcttcctc atttctatcc    38100 ttttcttact ctatgattga attaatcttt ctccaatgtg gcttgtactc atttacctca   38160
atggcttcca ccctccaccc acctttaatt gttactgaca tctgttatca ccttatttgt   38220
tctccaaagc cccttaaaa cacctatgtc tgtattcatc caacacattt attaagtgct    38280
tcttatgttc taagcactgt gatgctgtta aactttaaaa gatgaattgg aaaaaagca    38340 caactgtact attataggag cttagaggta gatggaagtg taaatagata attaacaggc   38400
agcgtgagag aggcgatgat agatgcatat ataaaaggct ttgagaatat cgatggaggc   38460
acaaataatt tcttcaaagg agtaggacag agattgtaat atttgaggtg aagggtaga    38520 tagagctggc ctggtagaaa ggccaaggaa gacatttcaa gcagaagaaa gtgcacatgg   38580 tcggggtga gtgaggcatg gaggataagg agaggagtgc ttggggatga gtgtggaagg    38640
aaaggctgag gcccaaagaa aagggccttg aatgcagtgc taaaaatttt ttgccttta    38700 aaaatggaag ccaacccaag tttattaaaa ttgtttgcag attgtagtgt cacaccgaaa   38760
tttgcaacta aagacaatag cattgtggtg cagaggatga tagacaggga gagagactag   38820
atacaaggag attgggttgg aggtccatgg tagtcaagtg agacccagtg aagggaccca   38880
gcaatggaaa cacagatgag agggcagatt ggacagatgg ttgggagatc tgtttgatgt   38940
gacatcgtga tccctaagta tgagggatga tactttgttc tgtgaagttc ccaatctttt   39000
gaagtcattt ttgctttgtt cttttaaaat gaaatcttcc taaatctatc attttctcta   39060
gttatatagg tattttgttt ctctgtataa gagtattact caatataaaa gttttttcaa   39120
ggacagagct ttcttcagtc atttttttct gggccccca gtcctctggt ggctattcaa    39180
tcagtatttt aaaaattgaa tcatggtgtc ctattcatag tttcagctta gttttgagac   39240
gtaatgtaac agatgtaatt ttacttgaaa atattattgc atgttttatt gaatttttatt  39300 tttagattgt aattaaaaac aataaaaatg ccttttgatt atccttaaag ttgacagcct   39360
tattcttttg agggaggttt tgggttttaa agataaccaa aggacactca aaaccgtttt   39420
ctgttagtta ataaaataat actctttag tccaaaagca agttttgaat acagtatttc    39480 ttttcttta ttgttcttaa actgatcctg aaggaaaatt gttagttaac aatcaatcag    39540
atgtattatg ggtgcccttg aaaataatca cttgaggact gtacttaatg taaaaaaata   39600
cattttataa gcatatcagt atgtaagtac attcttctag taggtaaagg cttaatcatt   39660
tactgtatgc taacatatta tactaccaca gtacaccata ctgtactgta cccaacgtaa   39720
tgtaccatgc cgtgcagtac cgtatcattc taggtatcaa caagtaacta tggtagcaat   39780
actccagtag ttttgaggtt gaatatgatt ctggtttgaa catgttaagt tgaggttctt   39840
atgagatacc taggtgtaca tgtattcatt tattagctag attatattca ggttttttag   39900
tggcaaagat gtacattatg gcaaatgtgt ataatttagg gtccaattaa ggatagcata   39960
ttgcatctag tgcatatatc ttaagttttct ttcaatctat tactgtactt tttctcttct  40020 acttataat aacttgttat atagacattg agctggttgc tttaagaaaa taataatgaa    40080
gacccagtta ctttaataaa atatcatttg acttgtttct tgagttactg ctagttttag   40140
```

```
aggaaataat gtgaaattct ttaagaaggg atataggcaa attgggaagt atatagagga    40200
gagtgattag ggagataaaa gcacatcaaa aagagcaata agaggaactg agattgtttt    40260
atttgaagaa gagatgactc aaagggatat gaaactctat tcaaatctac ttacttataa    40320
ccagtaacag taataatacc aaacaatatg gaggacttaa aaagtattag gcattgtttg    40380
aagtatttta agtatattat ctcttctgat tctaacagca ctccatgagg cagatattat    40440
tattattatt attttggtat tgtatggact acaaaactga ggcatagaat tgtagagatt    40500
tttaaggtca ggcctgatat aacagcacca gattttcagc ttatgcaggc tgactccaga    40560
gtaggcattt taaataaat atttgtgcaa caatcttgtc ctgaacaact gttgtattta    40620
aagcactatg tctagaatcc ttaaggtatc gggagatgat gagattatgg atactgctct    40680
caaaaaaatt tacagtccac acgacctaaa ggactgttat gtagaaagga aattatatcc    40740
atttgaatag taggacctca agtgatagaa caaagactgg agaagaaatt tacaggaatg    40800
ttcatttggt cttaatttaa ggaagatgtt aaataagacc cattacatgt agcatgatgt    40860
ttttactact caggccagtt ttagtggtca catcttctta aggtgtaata ggcagcctca    40920
gaagttactg tggtcttgct cactggaaat gatacacaga cagtttaagg gacttgcccc    40980
agaccacacg gcaagaggtg aatgtcagaa cctctttgag tacattttaa aataaggact    41040
gaaagttgga ggagggtggt tatcaaggct gccttcctta ccatagtatt cccagcatta    41100
acaaaatcct tggcatgtaa ttggaattca gatgcttctt aaataaatga aaagcctgtt    41160
gtagccagct tacagtttgc attaatgcag attattaaag tggaagatca taaatgattt    41220
tttattaata tttatgtcta taatcttagg tttggaaaac attattcatt cataataatt    41280
ttaattatat gttacattac cacattttg acttgtagtg ttttagcat agttcagcta    41340 cagtgtagct taataaagaa tatgattttt aaaatagca atgctattat atagccttta    41400
cagaacttct aaaaaatgac atgttctcta ccaccttaat actgaaactc aaatcttatt    41460
ttttgctacg attattccag ctactctttt ttgtctatat ttcatttctg cctttttatg    41520
ttgtggtcca agtaactctg agcttttctc atgttgtcca ttgttgcata aaaatcttcc    41580
agcatcttaa agcacagcct actcacacaa aaaagtgatt gtttgctaca gaaaatttct    41640
tcaccatcgt aatttttgc tacttcaaat tcagtaagca ttcttacaca ttatatttat    41700
tttatattca gtgatgaact attttttatag attccttaaa atttctggtt atttatttga    41760
taaggaaaca tgtactagaa aaaagtacaa cacatatatt gtgagattaa ttatgacaat    41820
ttctagaaag taacagtctg ttcaactcaa atgtttataa gaaaattctt tctttattta    41880
tttatctgtg catttaggca tgccagaaga atccagggag gatacagaat ttcatcataa    41940
gctaaatatg gttaaaaaac agtgtttcaa gaatgatatt cacaaactgg tcctagcagc    42000
tttgaacagg gtatgttgaa tataagtttt ctgtatttat actattaact aaaatattaa    42060
atttggagaa ctaggggcgc ttttcagtc taagttttct gttctccgtt tgctatgata    42120
ggaggaagtc atgtggttag agacataaga tgacagtggg gatgtgggaa gtgaaaagat    42180
atgtactaag ctaagtccag ctaagtgtat tatcaattat agatgtaggc aagattcttt    42240
tgattgccag taacataaat ccactctagt ttgctcaacc agaaagagaa ccaaagagcc    42300
atatatgcag ctagaccttg tgagtcatgc tgggtactat ggctgctgtt ttctctttct    42360
gtcctctggc tacttgtctt tcttttctgg tctcatagta tatggtttag cccatgaaga    42420
cataccagtg ttaacagtaa agtcttcggc tgggcacagt ggcccacacc tgtaatccca    42480
gcactttggg aggctgaggt gggtggatca cgaggtcagg agttcgagag caacctggcc    42540
```

```
aacatggtga aaccctgtct ctactaaaaa tacaaaaatt aactgggcat ggtggcacgt   42600
gcctgtaatc ccagctactc aggaggctga ggcaggagaa tcgcttgaac ccaggaggca   42660
gaggttgcag tgagctgaga tcacaccact gcactccagc ttgggcgaca agagtgagac   42720
ttcgtctcaa aacaaaaaca aaaacagaca aacaaaaaca gtaaagtctt ctttgattcc   42780
ctacgctcct tttcattgtt ctccggagaa ataacctctg aaatgatttg gtatacattg   42840
tttccatttt ttagcattta catatccatg ttcctacatt ataattaaag tatccataaa   42900
tcatactgag tatgaaaaag agaagaaggg aattacattt aaattgtgta atgcaaaaag   42960
tattggtgga attaagaagt tttggaaatt ttgcataaga tgaattggtt ctttattaaa   43020
gatgttaaga ataaagacat aattagtgtg aacatttta taaaaggagg agcctattta    43080
aaataattaa tggaaatgat tccatgtgat ttgatatact ttgatgaatg tcataaatta   43140
attaaagtgg cttccagaga gatctccctt aaaaattcat tttaaattga actttatact   43200
gtcactcact gcctataata tgtttgagtc atttatactc aaactttaat acaatccttg   43260
agtatggcaa gaatttatgt tgtaatgggt taaatttatc ttgagaaata tttgttgaaa   43320
ataagtatat ggaaggaagg ggttaggcat ttagaagata aataaatatg ctttgtactc   43380
ttctctcctg aatctcataa gccggttgtt gatggctgtt gtgaaacctt ggttcttttc   43440
tttaaacaag agacacacag cagaggagat gcagcatcga gtaatttatt gcaaagaaa     43500 aagaatattt tgcaagttaa gtgaggaata gacacttata ccctgacaga attcagggtg   43560
ggcttactag taaggatgag acagcgtaaa ttggcactag gaagactccc tttgtgggag   43620
ttgtacatga tttttcataa gtgggtggga agaagtgtta ctagtaagca tattctaggt   43680
tgtcctctga gtgaacatgt gcagtagctg tacatgcttg ttcatatatc gcatgtctca   43740
taagtatctg aaatctccac ccaggggtgt gtgtttact attataatga gcaaagggtc    43800
agtctgagga caaggaaaat caaaatgtgc atgctcccca cgctacctga cttcaaacta   43860
tactacaaag ctacagtaac caaaacagca tggtactggt accaaaaaag agatataggc   43920
caatggaaca gaacagagcc ctcagaaata atgccgcata tctacaacca tctgatcttt   43980
gacaaacctg acaaaaacaa gaaatgggga acgattccc tatttaataa atggtgctgg    44040
gaaaactggc tagccatatg tagaaagctg aaactggatc ccttccttac accttataca   44100
aaaataaatt caagatggtt taaagactta aatgttagac ctaaaccat aaaaacccta    44160 gaagaaaacc taagcaatac tattcaggac ataggcatag gcaaggcctt catgtctaaa   44220
acaccaaaag cagtggcaac aaaagccaaa attgacaaat gggatctaat taaactaaag   44280
agcttctgca cagcaaaaga aactaccatc agagtgaaca ggcaacctac agaatgggag   44340 aaaattttg caatctactc atctgacaaa gggctaatat ctagaatcta caatgaactc     44400
caacaaattt acaagaaaga aaaacaacc ccatcaaaaa gtgggcaaag gatatgagca    44460
gacacttctc aaaagaagac atttatgcag ccaacaggca catgaaaaaa tcctcatcat   44520
cattggccat cagagaaatg caaatcaaaa ccacaatgat ataccatctc acaccagtta   44580
gaatggcgat cattaaaaag tcaggaaaca acagatgctg gagaggatgt ggagaaatag   44640
gaacactttt acactgttgg tgggactgta aactagttca accattgtgg aagacagtgt   44700
ggcgattcct cagggatcta gaactagaaa taccatttga cccagccatc ctgttagtgg   44760
gtatataccc aaaggattat aaatcatgct gctataaaga cacttgcaca cctatgttta   44820
ttgtggcact attcacaata gcaaagactt ggaaccaacc caaatgtcca acaatgatag   44880
```

```
actggattaa gaaaatgtgg cacatataca ccatggaata ctaagcagcc ataaaaaatg    44940
atgagttcat gtcctttgta gggacatgga tggtactcag caaagtatgc caaggacaaa    45000
aaaccaaaca ccatatgttc tcactcataa gtgggaattg aacaatgaga acacatggac    45060
acaggaaggg gaacatcaca ctctggggcc tgttgtgggg tggggggagg ggggatagca    45120
tttggagata tacctaatgt taaatgacaa gttactgggt gtagcacacc aacatggcac    45180
atgtatacat atgtaactaa cctgcacgtt gtgcacatct accctaaaac ttaaagtata    45240
attaaaaaaa aatgtgcatg ctccatacag gggcaattcc ctactggaga tagcttttgct   45300 taaatgagct ggactacaat gcaaatgctg aaacttacta tattgacagt aagattgcca    45360
cagttgccgc gtcctgagga catggttact tcctttttaat acctatcctg tctcattgtg   45420
agaggattaa caactgtgca taaaaccagt tgttctacat gagcacttag gagggatacc    45480
agcattgtga acatagttta agtacgtaga ggagggaaca gttaagttta ttcatggtga    45540
gtgttggtga aaagtggaag aggtaccaaa acagccgtat agataactgg ttccagttag    45600
ccaacattct ctaaagttat tagagaagcc taagtgaggt gtaacctcag cagtcgggag    45660
ccaagagagc aagtaagtgc tgtgatgtgg agaaaatcac tttgttccaa ctgagaagaa    45720
atggttgagc actgcttttc ccccatgcca gtactgacgc acagcctttc acttagcact    45780
gattatcgat aggggtgggg agttaaggta tggggaaaca caagtaacaa tattttatttt  45840 caaaaacctc tccactgtaa ttcccctaat ccttcatcat ggttgaggaa aatggctcta    45900
aaaaatgaga gcaattactg tagctccaaa attctgtgat tgcatgtctt actctgaata    45960
gcaattacaa agcatcagag gatttaggtc caaatattgc agacacaaga aaatgaatta    46020
cattttaata catctaaact tggagagcag agttccaaat aaggtagaac ttgagattca    46080
actctgattt ataaagcaga gactaagaag agtatttata aagcgaatcc atgtttggat    46140 acataaagt gcaataaaat tcaagctgaa gttaaaatct ctgtctagaa cagcgatgtt     46200
ccatttatgc ctgatccttt tagcttttcc acagatgaag actttgtcac ctgttccaga    46260
gagatatatt tgttcattat tgtttccaga gagcaaaatg gaaaataaac tctgcacatt    46320
ttggccgcat ctgtgttttta tatgcggtga cactcctgtt ctcttcagtg aggaaatcca   46380
gtaaagtaaa accagtcttc tgatgaaatg ggcacaaatc aaagaacttg tgagcttcac    46440
aaaaaccttg aagcaaaata taccaagctt aaatattgaa tgtattgatt tcagtagtca    46500
aaaacagagc tcatctgcaa agcaacaac aacaatgaca acaacaaatt acatataagt    46560
aaaatttaaa aaaggtttac aggatgaata tacagaaaac tatgaagctt aggggtagag    46620
aggagtagtt gaatatatga aaagatacat cttttttgat gaaggactaa atttttaaaa    46680
atgaaaattg atctatgttt atgaaccatt agtaaaaata acaatagtat tttctggaac    46740
taagtaagct agtgtaaaat ttgtatgaaa aaattaatac atatgagtaa tcaggagaat    46800
tttaaaaaag agtgttgatt catatggcct aactccaaaa gataatcaaa tgtattatac    46860
aattttagta attataatgg tgtgatactg gcactagggg agagagatca gtgccacaga    46920
agggtggctc aggaaataga ctcaaataaa aatttgtaat gttatgatat tcctcgactg    46980
cgggaggaaa atagattact cagttacttg tgttggaaca actaactctt cagccatttg    47040
ggaaaagcaa agaaagctga atatttatct tactccttttt gccaaaacaa attacagatg   47100
gatgagattt aaagtctata atgaattggg tatatgtaca tattaaaagt ttcaactata    47160
attgttatta acgtaaatga caacggaaca ccttgttgga gggaaatttg gtaatatcta    47220
tcaaaattaa aatgccatgt tttctgatca gcaatttcat tctaagaatt tttaatgtag    47280
```

```
atatacttgc tcatgtacat aaagattatt agacatgaat gttcactgtg gcatgattcg    47340
taattaaaaa tgtggcaaca aactaaatgc ttacatggta atcattcatg ctgtttgcca    47400
gatattttta tttctccacc ttgtggtgat tctggcatag tatttagtag ttaggttgaa    47460
gcatgtgact aattttggtc agggagttgt aaatggaggg aatagctggt gagacatctt    47520
gcggaatact gtctcaggta ccatcgtacc tgcagtgttt gagatagtag ttgctccatc    47580
agtagaggtc cctgagggac tacaacaagc agagtcccct cctgacctgc aacacatatg    47640
tagcatgagc aataatggaa cttattattt ttgcacccta taaaattttg agaattgtta    47700
ctgcagctta atttaatctt tcctgacaat acaataccta tcaatagaga ctaatcagat    47760
aaattatacc atttccaaat tgtatcatcc tgcataaata ttaaaaaaca atgaggtgag    47820
attcctaatg tgctgctatg gaaaaatctt caatttteta tgtgtacgaa tgtatttccc    47880
aggtattcgt ttttccttc ctgtatgttg acacattatg cacactttg gatgaaatta     47940 atatatttcc accgctttat gtcctctccc tcacttttat cacccaattg tagcaaagta    48000
tatgtttgct tttatagctt tagctatata aaattttcta atagctaagt ttgtggttcc    48060
tggaattaag atatctgaat ttaaatctaa cactactacc tacagactat gcaccctgga    48120
caagtactta atgtcttggt tttgttatgt ataaaatgga gataataact gatttttcac    48180
ttagagttgt tgaatatttt ataagataat tcatgaaaaa gtgtcagtat aatgcttggc    48240
acatagtatg cgctcaataa atgttaatgt tattactatt agatttaaaa gtatcttttg    48300
acccctggct atagaagatg aggaaatcag agtatttgca cttctaatat ctcctgtttt    48360
cccacctact tttgttcaat aaattaactc cacattggca gggtagataa tatttatatt    48420
cagctttcta attatgcttt ctaagtttgt gtttatctta ctcctaccgt tatttggaag    48480
cagtcttcat ctcaagtcct tttgttactg tttttcact catcttttag ttgtctgaat     48540
ttctttagaa aagtttaatt ccctgaatat ttaatgttta tattttgttg ttgttttttgc   48600 ctttatattt ggactcctaa aaaaagtttt gttggttgta aaatattgtt ttttttttcct   48660 tgaagtgttt gtaggcattt cactgtgttc tagtactgaa tgtttagtg gagaagtctg     48720 aggccagctt catttgtttc ttggatattt ttgcccagtg ctgaaaggat ttttetctt     48780 gaaatccatc cactttatta gggtatatct caatgttagt cctgggatat ggtatcctca    48840
ttctagctat acattcaact tttttcctgg aaagttttct tgagttgcat ctttatatac    48900
atatacatac acgaatacat atacatggta aagatattaa ggataaagat aggtgctta    48960 taaataccaa tttgatataa ttttggcatg aaaaaaagcc tgtggtgcat tctgagtttg    49020
gaagtagaac tggatatact tacttattac tattgttttt aatacaaaaa tggagacagg    49080
gtctcactat gttgcccagg ctggtctcaa actccttgac tcaagcaatc ctgcctcgac    49140
ctcccaaagt gctgagatta caaatgtgag ccaccgtgac cagcctaaat atctaaattt    49200 ttctcttca ttattttagc tctcttcttt ggggctatca gtcatatgat gttggatctc     49260
ttttgcctta atcttctaat ttttcaaaga ctaatccaga gaccactatc tatcaccatg    49320
ccattactca tagacaaggg acatcattcc acacatttag cttatttgtc aaaatcagag    49380
atgggattta taaagaaaa agaataaagg gagaaaacaa aacacaaatt atctgggaat     49440
gcgagtctgt tttcctttct ttggctaatc tacttaccta gtagctagga aagaggccag    49500
catgagtatt tttccattga gctggctagc tcagtcattg gagaaaccat ttcaatattt    49560
atggattctc tgaaaaaaac ttggagagta aaaaagcata ggtggtagga tgctgccatc    49620
```

```
cttctgttgg catctccaga gtttcacttg aaaaacacct cctaagtaga cactgataaa   49680 ttgatttaa tccctatttg agcaccaatg caatacatta ctatttcaag atggagcatt    49740
agataactaa aggaaattct attgtgggct tgtaaatatc atgatagtca tacctatgta   49800
atacatatat gtatatataa atattaattt ttaaacattt acttagctat taaaaatcaa   49860
atgctcatat ttaaaattat tggtttatta atgcaccatc acatgttatc atgtgatact   49920
ctgaattctc tttttgcata gacaaatcag agattacctg ctgcaagtca ttagtcatca   49980
ttaacctgta ctgaaatggt tagagcctag gggagttcca ggtaaaagga ccagtaatga   50040
gtagaagctt gttagatgta gagatattga ggacagagat aggtgcttta taaatatcaa   50100
tttgatataa ttttagcata aaaataagcc tatgatgctc tttgagcttg ggagtagaag   50160
tggatatgta atttcaggg cgtagtataa aatggaaatg cacactcctt gtttgaaaat    50220
tattaacgat tttacaaggg tgacaacaga gcattgaagc aagtgctctg tgagcatgaa   50280
gccctgtgtg aaatacacac ctgtgaagct ggccttgcct gccaaacagg aatgctggta   50340
ctgttaatca aacagaaagt tcagaatgac aatctgactt ttttttgtag aagatactaa   50400
acttttggcc ttgaatatct gaatttaaga tactggtatc aagccaaaag aaatttgggc   50460
ttagaacttg aaagatttaa acttgtgctt tgacttgtgt gctcacagct ctctgtgtca   50520 caatttttt catctgtact tcgggacaac aatagtgtgt cgacatcaca aaggttttgg    50580
gaggattaag taggtgaata catatgaagt tcttaaaaga atgtctggca ctgagtgagt   50640
gctacctcgg ttttggcatc gttattgtgg tcattgctat tgttattatg acttgaagtc   50700
atattagtgt atgaaatccc atccatgaat agaagacaga aagaactttg ggcagggttt   50760
ggaggtaaaa gaagacattg taaggagat gggtaaagga atgatttaa agactgagaa     50820 taattagggg agtacgatgt catggaaatt aagggatgat aagcaccaat taagttgtta   50880
ttggactttt ttctttgaat ggttcaaatt cagaataata aggaaagaag tctgattata   50940
cgaaattaaa gggtagggtg actgtggagg tagtgggagt tgacttttct gctaataagt   51000
ttagaaataa aggaaaaatg gtagcttgag gaaagagagg agcgattaag ggaaagtctc   51060
tcgttaactc ttgtttttca tctctgagga cagcgcttag cccaaggcct gacctgtgat   51120
cattactctc tcaaggttta ttccatggac agagctatct catttcatgc ttataacaac   51180
cctacattat tagaattgtt ttagagatga ggaagctgag acacacacca aaccagcctt   51240
ccaatttcac tttgcacaac tttgaatttc tttatattc ttgaataaaa gttccacttt    51300
ttaacttacc acttcttagc agtcattgtc taactgagta attgttactt cattcattta   51360
atggttctca gattcgcata atttgaacct aaatttaatt ggcctccaag ctgatgtgct   51420
tacagaaaca gtgacaggaa acaaaaatgt caagggagac tatgtattat taagatgata   51480
aatgaaatga tgtccaagct gagcaattaa agtgtgaagt agaaggacac agggtgagaa   51540
actgatgctt ctcctcagcc tctataaaaa agatactgaa taaagataat tgagaggcat   51600
taggggacta gactgagaaa ggattggaaa tctgttcact gagagtacag aaatgaggaa   51660
gcttggaagg cagaagattt tggtcaaaga cgtctggctt gaagctattt cagctctttg   51720
gattatctgt ggtggaggcc atcacgtctt tggagtggag gtaccatgaa actagtgtct   51780
gcaaaacatc atctaaatga aagcaaaatt cctgagaagg atggcactat aatttttaaa   51840
agaaaagcta tgagttaagc attcatatca aggtagatgt ttggagtgta ttgcttgtgt   51900
gtgaaaaggc agagatgacc agaataagag ttagaggtat gctgcgtttt cttcttggtt   51960
gatgagtagg atggcctgga caaagaagtg acctctagta aaataccttc atagtgtcaa   52020
```

| | | | | | |
|---|---|---|---|---|---|
| atcatctgga | ggaaattcag | attaaagagg | ttggatgatg | tcgtaattaa | gatcctgggc | 52080 |
| ttttaaggtg | gacacattta | tattcaagtc | ccaggcccaa | tgcatattag | ctctgttact | 52140 |
| tgagctttta | tttctgcatc | tttaaagttt | ggcaaaccta | ttacatgaag | ctgttgaggg | 52200 |
| gataaatgaa | ataacgcatg | caaagcactt | gcagtaaaga | ctaattatca | atattttatt | 52260 |
| tgttaagagg | cagcattgcg | ttttactggt | caagtatgta | gactctgggg | tgaaacatat | 52320 |
| ttggtttggt | ttcatctctg | caatttatag | tttgtgtaga | ctttgagaat | agttctcaat | 52380 |
| cattctaacc | ctcagtgaat | tcatcttcta | atgggagtga | tatcagtatg | gatttcatga | 52440 |
| gattatgaaa | agaaaatgcc | tacaaagtat | ttattacaat | gcctggcaca | gaacaagctc | 52500 |
| tccttaattg | taaaaatgct | aactcttatt | cttcataata | aataaaagta | attaatgtta | 52560 |
| tagaaaacaa | aatcaaggat | actgatttat | atttggatta | cttgatttat | attttgtcag | 52620 |
| tctataactg | gtcttaacta | aggtaagtat | taagatctca | tttttaacag | cgagtattct | 52680 |
| tttgatttta | gttcattgga | aatcctggga | ttcagaaatg | tggattaaaa | gtaatttctt | 52740 |
| ctattgtaca | ttttcctgat | gcattagaga | tgttatccct | ggaaggtgct | atggattcag | 52800 |
| tgcttcacac | actgcagatg | tatccagatg | accaaggtca | gtacaatttg | aattcaggat | 52860 |
| ttagaataga | tttttgtagg | gcattagctg | gtgactggat | gtctttaaat | attttttcttc | 52920 |
| agttttgaga | tttaaaacaa | ttcttttttt | ttattttcct | agaaattcag | tgtctgggtt | 52980 |
| taagtcttat | aggatacttg | attacaaaga | agaatgtgtt | cataggaact | ggacatctgc | 53040 |
| tggcaaaaat | tctggtttcc | agcttatacc | gatttaagga | tgttgctgaa | atacagacta | 53100 |
| aagtatgtgc | attatcttgg | aaagaatttg | gaacttgtg | cgaatttcac | ttttggagca | 53160 |
| gtttgtgtaa | ttcccacttt | gcatgaatgg | ggtattctag | ttaatggaaa | accatttatc | 53220 |
| cttttgtagt | attttaatta | tacaagcaaa | gaaaattgga | ttgaatctct | aaagatccag | 53280 |
| tgtttcatta | tgaaatctct | aaagtcagca | tggttattca | ccatttatct | tgcccataaa | 53340 |
| agttcagaga | atgtgctaag | aaatcccagc | tagctgagtt | tattcgctta | gattttagat | 53400 |
| aaatagaatt | tataaatatt | ccaaagtttg | tcactctctg | ggttttattg | caggttgctt | 53460 |
| acctttagta | attttgcttg | ttgatttttt | tccttgcagt | gaaaaaatgt | ttttaacatt | 53520 |
| tttcatcaag | caaaatttaa | aacatgatat | ataataactg | tctttgtaag | gaattcaaga | 53580 |
| tactggccta | gagttagttc | acgggagatt | aagaataaat | ttgttttgtt | ttgtttttta | 53640 |
| attgtagcaa | aacaaatagt | ttttcttcaa | gagtttctgc | cttggttgtg | gagtttgcaa | 53700 |
| cttttcataaa | ctacaaagga | atttttttttt | ttttttttgga | gacagggtct | cactctgtca | 53760 |
| cccaggctgg | agtgtagtgg | cagatttcag | ctcactacaa | cagctgcttc | ccgagctcaa | 53820 |
| gtgattctct | tgcctcagcc | tcctgagtag | ctcagactac | aggcatgcac | tcccatgcct | 53880 |
| ggctaatttt | tgtatttttt | gtagagatga | ggtttcacca | tatttcccag | gctggtctca | 53940 |
| aactccctgg | tctcaagcaa | tctgtcctgc | tcagcctccc | aaagtgctgg | gattacaggt | 54000 |
| gtgagccaag | gtgcccagct | gactcaggaa | atatttttttg | taactggcag | cattgaccag | 54060 |
| gaataaaaat | acctggtctc | taatctttgc | acagacatta | tcagtaaatg | agagaatatg | 54120 |
| tgtaaagttt | tttaaaaaat | tataaagtta | tgaacataca | aaattcttag | attaataaca | 54180 |
| acaatgtgtt | ttataactgc | ttttcataat | gtgcctcagg | ctaggctgat | taaaccaaga | 54240 |
| taggattgat | taaagtaat | cttagggaaa | gggaaggatt | ttgtgccggt | atggaactct | 54300 |
| cagttactct | ggattaattc | atctaggcat | aaattttaga | atctctatag | tagagtttat | 54360 |

```
gaactaaatc tggcctgcca acatatttta tttgtccagt tcagggtttt gctttgtttt  54420
ttgagacaga gtctcactct gttgcccagg ctgtagtgca gtggcgcagt ctcagctcac  54480
atcaccctcc gcctcctggg ttcaagcaat tctcctgcct cagcctccct agtagctagg  54540
actacaagta tgcaccacca tgctcagcta atgtttgtat ttttagctga gatgggttt   54600 cgccgtgttg gccaggctgg tctcaaactc ctgacctcaa gtgattcact cacctcggac  54660
tcccaaagtg ttgggattac aggcatgagc cactgcaccc ggccttcagt tcagtgttta  54720
aaagttttta attcgaatga cgtactttct gcacatttgc atggcctgct ctgctgtagc  54780
attcacttgt tttcagagac ctctgctcta gaggcaggtg gatcacctgt ccctcagaca  54840
tacataaatt aaggctactt tgcttatcaa atattagtat tcgtagatac tcagcatcat  54900
aagagttcga agtaataatt ttaatattta gatgacgtaa gttaatttaa aattttttg   54960 agatggggtc tcactctatg gcccaggcta gagtgcagtg gcacaatctc ggttcactgc  55020
aacctctgcc tcctgggccc atcctcctgg gtgggctcaa gtgatccacc tcagcctcct  55080
gagtagctgg gactacaggt gcatgcacgg gtaattttaa atatttttt ataggcacaa   55140 gattttgcca tattgtgcag gctggtcttg aattcctggg ctcaagcaat cccacagtgc  55200
tgagattaca ggtgtgagcc atggtgtcta gccaattta ttaatatgta atattagagg   55260
taataaaaca ttaaaagtt aagatgatcc ttggtggctt tacccaacct aaataatact   55320
aaagtcaaaa gcccaatctt tcattaaaac atcacatgag tgaagaggac agactctggg  55380
gatgtgctta aggtggttct aaaaaagtaa cggtgttctt tataaataac ttattattag  55440
aatgtaatcc tcagagtgcc ctcagcgctt ctcaactaca ctcaacataa atgaaatcta  55500
ggagtccaca ctagcctttc tgagataaac atttcggaag acagcgcaaa agctggggg   55560 atatgctagg ctctctagag aacctactgt tcaatattat aatacaaatt tttactctat  55620
tgacctgttt ggatgtgtag ttctgctgat ccaaccgctt taatcctgtt taatatctgg  55680
gtttcatcct ataactatgg ctttagacaa gcatctttga aaaccaaatt tgagggtatt  55740
agttcttttt cctgctttgc tactgaatgg tttgttaact agcatttat tctctgtgcc   55800 tgctatattt cttagtcatg agagagagag ggagtattta tttacaggat aaatacttta  55860
aagcaccaac ccaatatatc tatagttaaa tgaacatcct aggtattgtt tcatatacaa  55920
actctctctg ctttatactg tttattcatt ttgcctgtaa ttgcttattt tattatttt   55980 tttcttatac ttttagggat ttcagacaat cttagcaatc ctcaaattgt cagcatcttt  56040
ttctaagctg ctggtgcatc attcatttga cttagtaata ttccatcaaa tgtcttccaa  56100
tatcatggaa caaaggatc aacaggtaca gtgttttca cttgcatcct aaatgttatg     56160
tatttatctg actctaattc tcatttccac tcttttagt ttctaaacct ctgttgcaag   56220
tgttttgcaa aagtagctat ggatgattac ttaaaaatg tgatgctaga gagagcgtgt   56280
gatcagaata acagcatcat ggttgaatgc ttgcttctat tgggagcaga tgccaatcaa  56340
gcaaaggagg gatcttcttt aatttgtcag gtaaatattc aaggcctcac ttttgtcttt  56400
gctcagtatt cttatagaat gtaagagccc tgccattgtg tatctcttac ttatatcata  56460
ttattcttca ctacagaaat ttaccagttt attgcaattg tttgtgtctt gtagtagatt  56520
tatagaattc cagaagtaat agggtccttt aggtgttatc cagtctaatc tttcatttca  56580
tctgtttact tatcttgtta agttgataaa taacttttca aatgtgtccc ttagtaggca  56640
tctctacaac ttagtctcca gatacactcc acataacaca tagttctaat gttttgataa  56700
ttttttaacc attttttcc atggttttag tttcttgcc tagaaagttc tcccctgagg    56760
```

```
gctaccacac atggctatgc aggctgtgga tggcacactt ttgtcggtgc cattcacagt   56820
gacatgagtt gctgttggcc aaagttgtgt aacactggtc tttctttcct tctctcttcc   56880
ctcctgaacc atgtaaacat atatctatct gattgttctg ctctcccttc aaaatataat   56940
tcaaattatc tttctttaaa gccctcccca tacctccaaa cctccaaaca aaattaagat   57000
ttacttcttt tgtcagtcta tgaaaatata tacatatctc ttgtatactt ggtgagttgt   57060
gtgaaaataa cagtgtacag tgttcatctt tgtatcattc agaatatcga gctcattgct   57120
ttacatatgg tgtgtattca ataaatacta ggttcattgc ttatatttca gatttgtatt   57180
atttgtataa gtgttagagt ttatactagc attcaggtag cactatgtct attttctaga   57240
aatttaatat ttctaacaaa gcaattatgt agtgatttaa tacacattat taaataatca   57300
ataaagtact atgtttgcca atagtttact ttttaaacct tactgtattt aatatcccta   57360
ctgtatttaa tatcccactt gcctatggat tgaaatcaat ttgttgactg ttaagattaa   57420
gttaatacta attagtaatc aacataaaaa gaaaagaat ttgtaaccca ttttcatgca   57480
ttacgtttat gaattaaaat cacataaaca atctaattat ttaaatttag tcaaatttct   57540
tttaagcaag caacaattaa aatagttgct ccgctttact aaagataatt aaattttttcc   57600 atcaataatt taatacattt ttactgtgca tcttttgcat gcagattatt gcattaattt   57660
taattgaaaa taccgaagaa ctaaaaagaa acttcccctt ctaagtccac attaaggaaa   57720
caacatacct aaaagcacct gatacaactg tactacattc cccacaggaa atcatttcta   57780
ctattctttc aatttatcca aatctttcta cccaacagga ttttacttt attcctcttt   57840 ccatattctt ttggacttca tatgcttagt tttatctttt cttttaaaa cgaaatctta   57900 aatccaagga ttatgtatta ggtttaaaga atttatccca gttgtcagag gttatttata   57960
tctagcaaac aataactgct gattaaatct tgtggatgag tttgtcgtat gtaccttatt   58020
tgtgccagag caaaataagg taatcaggac tatttattca tttaccaaga ggttacatat   58080
tgaaggacta tctagagcaa gggtggagtt tgttagact ttctgcagag aatttgataa   58140
tggaatgtac atgattggta gagaagaata tggaagttta atactgggta tgcaaatgca   58200
tggataaaaa cctcaaggta aaactcatca aatcacagtg gaaaaagtat agtgaagtct   58260
gaataaaaat aataagaggc tgggcatggt ggctcacatc tgtaatccca cactttggg   58320 atgttgaggt gggaggatca cttgagccag gagttcgaga ccaacttgag aaacatagtg   58380
agactccatt tctacaaaac aaaccaacaa gcaaaaaacc atgtatgatg gcacacacat   58440
gtagtcctag cttcatgcag ggtggctcat gcctgtaatc ccagggcttt gggaagtcaa   58500
ggcgggagga tcatttgagc ccaggagttc aagaccagcc tgggcaacat agttagaccc   58560
ccatgtctac aaaaagtcaa aaaattagct gggtatggtg gtacctgctt atagtcccag   58620
ctacttggga gtctgaggtg ggaggatgac ttgagcctgg gaggttgagg ctgcagttag   58680
ctgagattgc accattgcac tccagcctag gcaacagagc cagaccctgt taaaataaaa   58740
taaaataaaa taaaataaaa taaaataaaa taatataata aggctgaggt gggaggatca   58800
cttgagccta ggaggtcaag gctgcaggag ctaagattgt gccactgtac agcagccttg   58860
gtgacagagg gagactctgt ctcaaaacca accggtcggg tgcggtggct cacgcctgta   58920
atcccagcac tttgggaggc cgaggtgggt ggatcatgag gtcaggagat cgagaccatc   58980
ctggctaacc cggtgaaacc ttgtttctac taaaaaaata caaaaaatta gccaggcgtg   59040
gtggcaggtg cctgtagtcc cagctacttg ggaggctgag gcaggagaat ggcgtgaacc   59100
```

```
tggaaggcgg agcttgcagt gagcctagat cgcgccactg cactgcagcc tgggcgacag    59160
agtgagactc cgtctcaaaa aaaaaaaaaa caaaaaacga accaaccaac caaccaacaa    59220
aacaaacaaa caaaaaacca acaaaaccaa acacttctat catgctcatt accacctggg    59280
cactgctcca aatactttac acaatttaat ccttacgaca acctacgaaa aggtccagta    59340
ggttctaatg ttattcccat tgtgcaagtg agaagctgag gcactgaggg tttaaataac    59400
ttgcctaaga acaagctcct ggtaacagtg tgaaatctgc ctccacagtg cctgctttaa    59460
tttcttggct acacagcaga ttcatggtag tggtggtagt ggtgttcatt ttctctaaaa    59520
taacagtttg aataatttgg ttttgataat gcactgcatt tattataaat tagatgatca    59580
gagaaagatt gcagggataa gaaattatgc ttttgataat ctttagttat attcttaatt    59640
ttcttcatta ttatttaaat gtaaaaataa atatctgtga gcagtagtat tttcctgtca    59700
tgaagctgaa attactttca taaatatgtg tgaatattct aaagagaatg actctgtagg    59760
atttaaagaa attaattctt attttgctg gcatttattt attttatcag attcactttc     59820
tcatatatgt ctctcttcat ggcaccatat gcctaaagtc agcttggata gtttggatcc    59880
tccaaggaaa attccttcca caaacatgtg cagcacacag tgctagataa ttaatagaga    59940
atataaaatg ggtttcctgt ttcaagatgg tttgtaggtc tgtatgtgta gggcattgac    60000
aagagagtaa aacataaatc acctagtac aaagtaagga gtgaatggca tatcttagag    60060
aaaaaaaagt tactgggcta aagagaagg catttgtgag tttttccctc cctccccgct    60120
tcccttccct tcccttccct tcccttccct tcccttccct tcccttccct tcccttccct    60180
tcccttccct tcccttctct tccctccct ccccttctct tccctccct ccctcccct     60240 ccctccct cccttctcct ttctcttccc cttcccctc ctcttccct tccccttctc       60300 cttccttcct tccttcctc ctcttccacc tgccttcctt ttaattttgc tatgagccct    60360
taaagaggat tttagtaatt tgctacttaa attaaatata tttgctagat gttgtgctag    60420
gcttcaggaa tacaagttgg attgcagtaa tgtaaagccc tttgcattct agcaagaaaa    60480
cagatgggta tgtatgtttg ctcagtgcta cattaaatga aatggatggg agccgggagg    60540
agaaatggtg tgtttggcct gagaggttag tagcaaggac ttctctgcaa gaaagtttga    60600
agccaattct tcaagaatga acaccttttt gctgggtgaa aagtagagga aggcatttgg    60660
ggtaatagaa atagcataaa aggtaatgag gtttgaaaaa ttacatgctg tgtttggaag    60720
aatgtcctgg agcagcagcg ttttagaagg ttttttaaaga cgatggtgac ttgatcagag    60780
ctctgtagtg ctttgaggat gggttgaagg tgggcgtact tggagactgg tgggcattta    60840
attggtgcct tccaaccaca taaatgaatg tcccctcaaa tcccttggaa acactttaat    60900
tctagaaaat tcaaaaattg tccccaacat cttttttcctc tgagttggta ccctggatct    60960
ttgggtcttc ttttctttcc ttttttgatg ttttattttg ggtaatgaaa gtcacacagg    61020
ttttgaagcc agcagatttg gcttcaaatc caagtctcag ttgcttgcta gctgtaaggg    61080
acaaattata tatcttttct aaatactcat ctataaaatg ggagtaataa ttgctatggc    61140
ataggatttt tttaaaaaaa agattagaaa tcatgtgtgt acagaattta gcacagtaac    61200
tgatggatat tatttctatt acctgttatc ttggtcttct agttgatagc tccttgctag    61260
cgtctagctc ctttccatag ctcttcctga gtagggccag catgcagtgc cacagcttgc    61320
taaggcttct cctggattgc tgagttgttc tagttttgt ggcacctcac atgctaaccc    61380
accctgaaca catgctctga aaacataaca tttagaggaa ggttgaagac tgagagacaa    61440
ggtatatctt tgaggaaatt cagatgcttg tcttgaggag ctcaggaaag ctagacacga    61500
```

```
gtaatgactg tcgtttgtgt gtggcattaa taaattttac aatagctatg tccccattta    61560
gttattctat gtcacaaata aaggcaggac agtagtattt actgtgttaa ggtactggtt    61620
tcccaggtat cttacagtga aagacagaa gctcagaaag tgtaagcaat gtgcatattt      61680
ggtggagtct ggatgtaaac agagatcttg atgccaagcc tgtggagctt tgtctccata    61740
taatgttgtc tctttcataa taactgactg tcatgtggca gattattcat gctattctga    61800
cattgatggc attaatatca tcttattttc ccaatctatt caaggatcag ttttgcctta    61860
ttttattttg tttcattcca aattggagat gtagagaaaa atcacatgaa gtttgatttg    61920
ccagtctcct aaaaggaaga aaaatgtaga ttttaatat acttaatttt ttttcttaa       61980 taggtatgtg agaaagagag cagtcccaaa ttggtggaac tcttactgaa tagtggatct    62040
cgtgaacaag atgtacgaaa agcgttgacg ataagcattg ggaaaggtga cagccagatc    62100
atcagcttgc tcttaaggag gctggccctg gatgtggcca acaatagcat ttgccttgga    62160 ggatttttgta taggaaaagt tgaaccttct tggcttggtc ctttatttcc agataagact    62220
tctaatttaa ggaaacaaac aagtaagtaa caaggagaat attttttaca attcttattt     62280
ttaatagtat tttttttaagt cactagtctt ttagtggtta ttcatgccag tttgagggac   62340
cttaagccaa agatattgca aaggtttgga ttttttttttt ttttggctat gaaatacttc   62400
aaaatgacat ttaagttctt tatgagatag caaatagtta tttataaaaa tagagcaaaa    62460
tagtggaagc ttttttgaagg ggtactttt aatatatatt ttttattatt aaagtaagat    62520
atccctgttt ttaaaggaaa tataaaatta taaaaaagaa aataaaaata acttatttta   62580
tctcttataa gtaattaata tggatatttt tcctaacttt ttatatgctt acatgtacct    62640
atgcattcaa atgtatgtaa aagcatacac acatatttat ttggcatttt taacttagaa    62700
tatactttat atttcaattg ataatgcatt ttctttatac tttcaagctc atgtgtattt    62760
tgtacatatt atgtgtattg atggtaagtt accatcttct gacactattt ttatctttttg  62820 agctctctca tttgttcaca ctaaatgtgt ttttagcgtg aaagctccca gctttccctg    62880
tgttaactta gtcccatgcc catctccttc cccatggtca tcaaactcca tgaatcaaca    62940
ccttaaggac catcttgcaa gtaacatgtt tgcttctctc atttttatga tgcactcact    63000
agcaaaacac cagttttggt cagtctacca gtctactttt tccctcagtt tcaccaagaa    63060
aactgagtgc tgctagagaa aagtacccat ccatgcaatt tggtgccttt atacatcaag    63120
gtttccaacc gctcagtagg ctccaaaagt tccaatcagg ctgaattttc ctcggtttct    63180
caaacacttc gtgtaccctt acttccagtc tttttccagt gttactctct ctctacctag    63240
ctctaaattc tctcttcacc tggctgtctc ttcattcttc ctgtctcagt gctatcacca    63300
gtctggaagg ttctcttaca tgaccctata gcactttatt tctcacatat actaccattc    63360
accacattat ataatttaat ttttcatttt tataatctac tttttggtaa attgttagta    63420
ccatgaagtc aatgtcaatt ttgttcatgg ttgtaacctt accattgata ctagtgtttt    63480
gcacatagta gattatcatt tagaattaag tattcaatat tggcaaaaaa taaaaattgt   63540
gtaatacatt atgttgataa gcatgtgtgg aaacatgctt catatattga tatgaattta    63600
aattgtcctc ttttgaggac aatttggcaa tatctactaa tattttaat atatgtacat   63660 acttttttga cctcacaatg tactgttagg aatctatgat acagacattc tcaatgtgca    63720
caaaaattat gtacaaaaat gcacattaaa acattgttta taatagcaaa agagtaggaa    63780
aaaaacctaa gtattcccca aaaggaacta ttcaaataaa taatggtaca tacatgttgt    63840
```

```
ggaatgcttt gcaatcattg aggaaaaaaa aacgtggagc aaatttaatg tcctgataaa    63900
gattacatta ctccgtggca aaaaaaaggg cacagacagt gttttttacta tgctaatgtt    63960 gatgaaaatg caactggaat atgatagtta taaaagtttg aatatgaaat aaaaccctcc    64020
agaaatgggt tccctggttg tctctgggtc tttggaaatt actgagacat ggttagatcc    64080
catgtttcat tacttaaact agtcttatgc caaaaacctg cttactttaa tcttcaatat    64140
ccgatggaga ggaattgtgg gcccattgga gagggacaga gggagattta tcattcacta    64200
tattctcttt gttctgtctg gagtttttac cattgacaca tcttacccag ttaaaaaaac    64260
atagaattgt catttgatta attggagggt ataaccatga tttcactggc agctggtctg    64320
agtaaagaac actttgggtc atagctttca aacatttttc aggtagtatt tgcctaagtg    64380
acatatttgt gtgtgagctc atcctaccgg gcttcgggat aatttcccat atcataacat    64440
attactctgg aaaaaggaac catttgggta tatgggtata gtgtaagcca tagtatcagt    64500
tgccttcttg gggtttatca tatgggtcca ccacatattt acagtaggaa tagatgtaga    64560
tacatgagca tacttcactc tgctactata attattgcta ttcctactgt tgtcaaagtc    64620
ttttagctga ttatctacac ttcacagggg taatatcaaa tgatcccca ccatgctctg    64680 agccccaggg tttattttcc tttttacagt aggaggccta accagcattg tattagccaa    64740
ctcatcactg atattgtac tacatgatac agcagtatca tgtagtaata tttgaagtca    64800
ttacagtagt aatatttgaa gaaatcttcc tggctgtatg tagaacaatg aggactcagc    64860
caacttattc ttcatagtag agctaataca taatgtaatg aagttgtgag aagaatgtta    64920
actttgaaat tccatcaggt ttcccaatag tcataatgaa tcactcagca aactttataa    64980
aaataacaag atcctttatt tagcagttta tgtgttctat gcattgtgct aaacatttta    65040
tatgcatcat ttcaattact cttttttcatc accatatact gtatttatta tcatcttcat    65100
tttccaggtg aggacactga tacccaggga gctcatataa ctcacaaatg gcatttctat    65160
gacttgaaca caggcctgtc tggcttcaaa gcctaggcct tttcctgaat aaagttagtt    65220
ccatagagat tcagttttgc tgtctacatg aaagcattgt gtacatggtt atgtttttt    65280 aaaaaatata tgatctgcca cctgttaatt attcaggatc actagtgtaa ggtgactttg    65340
aaaggaaaaa tagaaatatt ctccagaagc atagcaatac gtaagaactt tggtcctatg    65400
tatgtttatt tttgcataat tgttgatttc taagttgctg gtgtatctct tattttcaga    65460
tatagcatct acactagcaa gaatggtgat cagatatcag atgaaaagtg ctgtggaaga    65520
aggaacagcc tcaggcagcg atggaaattt ttctgaagat gtgctgtcta aatttgatga    65580
atggaccttt attcctgact cttctatgga cagtgtgttt gctcaaagtg atgacctgga    65640
tagtgaaggt atttattata aaaaaaacc ctttatgctt tatatttaca cactgacatt    65700
gaacaatagg acccaagaca aaaacctgac ctaaatcatc tggaaaaact tgagtagaaa    65760
tgtgtttatt atcgcaaaca gttaagttta ctaattttgg ttaaagtgat gggtcaagga    65820
agtgtgtctc tgtgcttcta aatgttatac taattggtta atggttaata ttccaggaaa    65880
caaactctga ctagactgga acgagattcc acgctctgtc attgactaga tcctttcgtg    65940
gcttgtgtaa gcccttaac cttgttaaag gtagtaatgt cgactttgca gggttataca    66000
taataattag aaaaaatgta tgtaaaatgt ctgcaacaat gcttggcaaa caggaagcgc    66060
ttaataaaaa aggttttat ctttactata gcttaaaaca atattaatat tttaatagct    66120
cacttgagat aacttttaa aaaattaata tggtgaaata taatgacag atgattaggg    66180 ctgatgtatt tagcattagc agtttggtaa aaatggagtg aggggctttc ttattaatat    66240
```

```
agtatgattg aaaacactgg gtgatagaat aaggatatt  gagagggcaa aaaatgagag   66300
ttgttccaaa atattgtgtc tcaagtcaaa ccattttaa  aaatcaagtg tagtgattta   66360
tatacatata taatttatat aaaataaaat gcattcactt taagtatata ttttcatgcg   66420
ctttgaaaat taacatattc atgtggtcat tgtcgctatt aagttatgca atattttcat   66480
tatccaaaaa agtttcttca tgcctcttca ctgaaaacat ccccttcccc tggccccccct  66540 gacccttagc aatcatttgc ttcctgacaa tgtagattaa tgttttctct agttttatat   66600
acataggatc atacagtgag tactcttttg tgtctgtttt ccaaaatgat tgtactatgt   66660
tctaccccca ccagcagtac atgagcattc tggttgctct acatccttgt cagtacttgg   66720
tattttcaag ttacttttag ctgttctagt ggaggtttaa ttcatttaga tgtaattttc   66780
atttccctga tgactaatta tgtagaggat gttttcatgt tcttattggc cattcttatt   66840
tttgtgtgaa gtgttgaagt attttgcttt taattgggtt gtcttattat ataagagttc   66900
tttgtatatt ctagatagaa gttgtgacag gtatatgtat tgcatatttt tttcccagtc   66960
atagcttgtc ttttcatttt actaattcta tttttaacaa aacagaggtt ttaaatcttg   67020
gtgaaatgca gttttccagt ttttttcttt tatggtttgt gcttttttgta tcccacttaa  67080 gaaacctttt cttagcctaa atttgtgaat attttctccc atattttctc ttagaagtgt   67140
taaaatctca gctttggcat ttaggtctaa aacattttaa gttgattttt gtgtgtggtg   67200
tgtcaatgaa gagttgacat ttatttcttt ctgtatggat atccagttgt tccaacatta   67260
cttgttgaaa atattatata attcctcatt gaattaatgg aagctttgtt ctctttaatt   67320
gactatttag gtatggttct attttagcat tatttattct gtgccactga tttataccctt  67380 attcttatgc caataccaca ctgtcttgat tactctagct taatagcagt tcttgaaaatc  67440 agatagtgta agtcctctgg tgttcttttta aaaaaaattg ttcttattat tctaggttct  67500
ttgcatttcc atataaattt ttaatcaact aactttatgc tgggattttt attgtaatta   67560
agtccatatt tagattttat atagaattta tttataaatt aaatcatatt acctatgatt   67620
ttaatgtaat ctataatata taattaatac ataaataata atttatatag attatatcta   67680
taaattaatt tgagggaact aatatattaa taatgagtct tttgacatat taatgtgata   67740
tatagttcaa ttagtctttt aaaatttcta acagtgtgtt gtattggatg ttttctgata   67800
ctattataga tggtattgta tttgaattct aatttccagt agttcactgt tgatatatag   67860
aaacataatt catttatttg tacatgaatt ttgtatcctg taaacttact aagctcactt   67920
acgtgttcca gtaccttatt atagattcta caggattttc tttgttcaca attataccat   67980
ttggtaataa agacagattt gcttttctctt ttctaatatt tatgtcttct ttttttttct  68040
tgtcctattg cactggctag gacctccagt actatgttga atagaattgg tcagactggg   68100
catcattccc tggtttccaa acttagagga aaaacataca gtctctaatc actaattatg   68160
acattatctg tagttttttca tagatgccct tcatcaaatt gaagaagctt cttcctagtc   68220 attttttggag agccttttttt tatcattaat aggtgttgaa aaatgctctt cagcatctgc  68280
tgaggtattc atattttttca ccttttatttt gttaatatgg tcaaatacac tgactgattt  68340
tctaatgtta aaccaacttg cattcctgga gtaaatctca cttggttatg gtacattatc   68400
ctttttatat agtattaaat tttgttttct aaattttgtt aagaattttg catctgtgag   68460
agatattagt ctgtagtttt atacttcctt gtaattatgg gagtaatgct ggcctcttga   68520
aatgaattgg gaagtgtttc ccattccaca atttttctgga agaatttgtg taaaggtatt   68580
```

```
ttcttcttaa atgtctgata gacttcacca gcaaaggcca tctaggtttt aaattttttgt    68640 gaggaggaga tttagaatta tgaatttaat aactttgata gatgtatgat tattttaatt    68700 ttctttact tcttaagtca gttttagtaa tgtgtaactt tcaaggaata tgcccatttc    68760 ataaagttg ccaaatttat ttgtttaatg ttacttatag caattattta attatcctgt    68820
tagtgattta attatcctgt taatctcttc aaagaatcag attttttgtta tattgatttt    68880 ctctattgtt tgtgttactt tctcacggac ttttgttctt atctttattg ttccctttc    68940 cttacttatt tttattttaa ttgactcttt ttatagattc ttaatttgga agcttagaac    69000
actggttttt agaaccttct tatttttgtaa cagaaacatt tatttaaggc tgtatatgtc    69060
cttataaata tcactttcac tgcatcccaa tattttgatg tgtcctcttt ctattcattt    69120
aaaaaaattt aatttcccaa atgtccaaca atgatagact ggattaagaa aatgtggcac    69180
atgtacacca tggaatacta tgcagccata aaaaatgatg agttcatgtc ctttgtaggg    69240
acatggatga agctggaaac catcgttctc agcaaactat tgcaaggaca aaaaaccaaa    69300
caccgcatgt tctcactcat aggtgggaat tgaacaatga aaacacttgg acacaggaag    69360
gggaacatca cacaccaggg cctgttgtgg ggtgggggga agggggaggg atagcattag    69420
gagatacacc taatgtaaat gaggagttaa tgggtgcagc acaccagcat ggcacatgta    69480
tacatatgta acaaacctgc atgttgtgca tgtgtaccct agaacttaaa gtataataaa    69540
atatatatat atatataataa atttaatttc ctttgtgact tctttgattc acgagttatt    69600
tagaaggctg tcatttattt tccaaatatt tggagatttt ctggataact ttctggttat    69660
tggtttcagt ttgactttt tgtgctcaga taacctactc tgatgatttc tatccttta    69720 tatttattga aacatgcttt atggattatc atatggtctg tcttggtgat gtgccatgtg    69780
caactgaaaa gaagtatat tcagctgtta ttgggtcaaa tcataggcc aaattgtttg    69840 gtaggatttc tcaagttttc tgtgacttca ctgacttttc tttctattta ttgtatttga    69900
tagagaaata ttgaagttgt aattgaggat ttgttggttg cctttttcagt tttatctgtt    69960 tatgctttgt atattttgaa gctctgttgt ttgttgtgca aacattaagg actatataac    70020
aaaggactat atataaaaat aatttttttaa ataaagtaac cactttatat taatctaagt    70080
ttgcagttag tatcattttc ttcctctgga agaattccct tttacatttc tagcgcagat    70140
cttccagaaa cccatatgca gattactgga gcacttttc cataactgcc ccagaactcc    70200
cagctatctc agtctccata aatgttgatc tctatctcct catctcagga aagccatgag    70260
actgtttaaa tttcttctta tgtatatggc ccttaatttg tctctaagca gaaggccaga    70320
gtgatcatag ggctcacata atttgtttcc cttctttcgg gtattacata gtcctatgct    70380
gtctgttgcc cagtgtctgt atccagtcat ttaatatatt tatccagttt tcttgttgtt    70440
tatgtgagta ggttaagttc acatttgtta ctctatcatg cctgaaagaa ctctcttcaa    70500 gtattttca agaaaacatt agaaatttta acataaaata attataaaat gcactatgct    70560
gcttgtacaa ataatgtgct aatagacatt tcacacacat ataaagtggg ataattatga    70620
taatttaata atcttttataa ttatgtaatt gttactaaat tataaattat atttttattaa    70680 aattcttaag cattaaaata atttaaacta tagaattaat taaacttttag caatgaacca    70740 ggcaggaact gtttatatca ggatttatac tgaatattat aagggtggta tttggatata    70800 cagatttat aatttggttt tgacataaaa tgaattcttt cttttttctaa gataaagagt    70860 agggggaattt aaaatcataa ttaatttttc acaaatgcat tcacattatt tatctttaat    70920 atgattttt tattgatctt tgttttcttg taaatttatt attttgaaag tactgccttt    70980
```

```
tccttatttt ataaaacaat tattgccagc caaatttatt gtgtttattt taataccatt    71040
ccataaaaga aaccatgaaa catgaaattc aaatagaaat ttattaaaaa ttgctgactg    71100
ttaaataatt tgtgtgatta caacatttaa agcaagattt gaaaaattta taagaaaaat    71160
tcagggagtt aatccactct ctttcctatg ctgctagacc ctattccagc ggtctccata    71220
aaaaaaattc agagaaacag aaagcagtaa cagtgatcag attgcataca aactttctgc    71280
acacacatat atttgttata acttatgtaa ccgttgattg atttggcttt ttcctgctgg    71340
actatgagct cctctgagga atagatttat tttttttctg catatcagta tcccgtgctt    71400
acccagtgtc tagtctgtaa cagccattct ataaatattt atgggtgaag aaaaatgttg    71460 ttgaatttttt aaagtgaaaa accaacatgg cttatcatct ctattttaaa gattttacaa    71520
agggaatgga ctgtgaaatt tccattaata aaaataggtc taatcttcca tgattgaact    71580
atgatagaag gatcttatga ttgagtaagc ttttttgtatt caccttcatg ttatttttatc    71640 attttcaaaa taggaagtga aggctcattt cttgtgaaaa agaaatctaa ttcaattagt    71700
gtaggagaat tttaccgaga tgccgtatta cagcgttgct caccaaattt gcaaagacat    71760
tccaattcct tggtaagtta aattgtgcaa ttgtgattat gttgtgtttt gctgctgaca    71820
ttctcttgat aactaaaatt tatgccaaag ctaggaacaa ttggtaggga tttccctgat    71880
gtatgaaaac tataattttg agattttat atatgtaata gatatgaaaa catattagat    71940
gtaaattatg ctcaattcac atttgtagtc ttttgagtat gcagggtatg aatttttttgg    72000 ggcacatata tatatatata tatacttaca gtacacttca agatggtttt cttctttctt    72060
ttcagaactc catgtctgaa aagagcccag gctagacctc tacctaatgg tgtgggttgg    72120
tcccatgaac actttagcta gaaatctgat agtgatttct aagaaaccag acagaagtct    72180
gaaggacact gaacaagatg gagtagcata atataattca ttgttcatct atctatctat    72240
catctatcta tctatctatc tatctatcta tctatctatc tatctatcat ctatctatca    72300
atcatctatc tatttttggtg tattgaaagt catttaattt tttagatacc tttattatta    72360
tttcaacctc ttgtctgttt tggaactatg gaaggactat ggcatatttg catgaggagt    72420
ctgataattc tagttgagga aattgggagc caccttattc tcaggttcac tttgaaagac    72480
ctgttctaac ctattctcca attttgatta tagctgagta ctaaaaatat gagggttgtt    72540
ttgtgttaat tctagatctt aagatgggtg aaatgaatga ctgtagttga atcggttaaa    72600
ttagctgtca gtctttatat gctctttcga atttatatat aaatttagtt ataaaaagta    72660
gtttggttaa tgagaaatta tatggatata gcttttcac tcaacctttc tgttttcag    72720 tttccttata tttaaaacaa aggagaaaga gtagatgctt tctaaggtca tttgagcact    72780
gaactggagt tttcttttat cctcataatt gggttcttag tttttacttg cctatttttt    72840
cccataatta taaataccat taaccctatt aaaatttcat ggttccttcc ttataaaaat    72900
gtcctcttct ccaataaatg acagcaattt tattataaat tattttttaa taggggccca    72960
tttttgatca tgaagattta ctgaagcgaa aaagaaaaat attatcttca gatgattcac    73020
tcagtaagta tttggatgta atcataagta aatagatatt ttgggcagaa tgcagtgttt    73080
ggttgaattt cctccaatta ttcaaatatt cttggtgcca gtttcatctt acataatctt    73140
catatatatt tacctaatga ttccttccat aagctataga aaatgaaac atacatttaa    73200 aaatttacct ttcttgaata ttatagaaca cattagtctt tttttttaca agttttctga    73260
aatgtaaata acacctccac caaggccact cttcatcctc tcctccagtt ttctttcttt    73320
```

```
cttttttttt tcacaccact tacaccacct gattaaatgc ttttattta ctgttcatct    73380 ctgccactgg aatgtaaact ccatagttg gttttctact gaatcttcag tgccttgaag    73440
aaagcctgat tgctaggagg tgctcactaa acttttacta catgaattta aattatttgc    73500
ttatatttcc attgtttgtt tgttttgac aaaagggtca tcaaaacttc aatcccatat    73560
gaggcattca gacagcattt cttctctggc ttctgagaga gaatatatta catcactaga    73620
cctttcagca aatgaactaa gagatattga tgccctaagc cagaaatgct gtataagtgt    73680
tcatttggag catcttgaaa agctggagct tcaccagaat gcactcacga gctttccaca    73740
acagctatgt gaagtaaatt taatttatcc ttgtaacttt caagacattt gaagagcttt    73800
tgtatttata tctaatttgc ataattaagt cgtttaaaag aacattctac ttttgtgtca    73860
ctgggtgata agtcccccgt gcctctggtt tttgcacaca tatcttagtc tgtgtgatgt    73920
tcaggagcat ctttgagggc aggcaatgga aacagatctg attagaaagg aattccaggt    73980
tctgtacgga gtacatgtta aagtctgtca agtgtatatt gattatactt taatcattta    74040
attcaagtaa gacaacttca acaatttaaa ttagattagg taaactagaa ttagacctgg    74100
tttggtagta ctggctctga ctcagctacc aactgtgtga caatatgaac atgtcactcc    74160
gcctgctcta atccttcatt ttctcatctg tgaaatagag attcaactaa atgattactg    74220 aaagttttt tttcagttta aaataatgtg taacttaaag attttttct ttttggtcaa    74280 agttcctgtc ttgtaagaat taaagtataa catagtttgt tgataggata gctctctgaa    74340
aattgacttt gctcaccatt tgtatgtact acagatcaaa atagttttga aagccaaaga    74400
agatatcata aaagttaaaa ttattttaat gcaaatgttt aaattgttaa attctcaagg    74460
ctgggcatgg tgactcatgc ctataatccc agcactttgg gaggctgagg cgggtggatc    74520
tttttgagtt caggagttca agaccagctt aagcatcagc aaaatcctgt ctctaccaaa    74580
aatatgaaaa attagccagg tgtggtgggg tgcacctgtg gtcccagcta cttgggatgc    74640
tgaggtggga ggattgcctg atcctgggag gcagaggttg cagtgagcca agatcgcacc    74700
actgtactct agcctgggca acagagtgag accctgtctc aaaaaaaaaa aagtcttgtt    74760
gcaaatgcat ttccccctttt ttaagcctaa aaaattaatc ataattttga gatgttttaa    74820
aggcaacatt acataaattt taagtatatt taagggatgt ttttctcta aagttttat    74880 atctggagac agagagaaga aagaaaggtg acccactcct ccagccatgc cctaatgtct    74940
aaaatgtgtc tttctctctt ctccacttct ttgccttgct aaatacttca agccacccag    75000
ggctcaattt aactgtcact tcatcactct ctgcttctct tccttttcc ttctaccctc    75060 cagccaacct acccacctag cctccatgtc cataacacct gatgctttcc acctaattct    75120
cattcggtca tccaatttga tttaaaatac ctttgccccc actagactgt gaactctttg    75180
aggacaggac ttgtttcagg cttgtttctg tctattccca gtgcctagtg agatctgaca    75240
tatggtagaa gtttagtact tactgaattg atttgtggag gaataaatgt ctgaacttg    75300 gtaatccttc aattaatatt tgttaaatga gcaagcaaaa taattttggg atttagtcta    75360
gttaaaacaa agagaattgg aagagactgt gacaaggtga gacatgccgg cattcaatga    75420
ctggacaagc tcagaaccctt ctcttaggga aatttcaaaa tgcaccatt agatggcact    75480 ttgtttgttt gtttgttatt gtcaaagggt ctcatctatg ttccttttat aggaacattt    75540
cctgattaaa ccttgggaat aattttaaaa tctttacttc agaataagtt aatgagggtc    75600
tgaaacaaaa gcaggaattt tgaaacaact tctgggggcta agagtggtta ataagcctct    75660
ataatgatat caaactctag agtttctcgt gtggataaat atattgataa ataaagaaga    75720
```

```
ccatagagaa gtgattgatt ttggtatttt agctctttga gagtattacg tacctaagtt   75780
ttaaaaaatt gacataatgt gtaagtaggg gtttgctatt atcattataa aattagaaat   75840
tgcttaaaaa tagaaagtag aaatttgaaa caaaaagttt cgtaaaaaac aggaggttct   75900
aaaatgaaac acattataag taactatttt tatagttaaa tcttaaatat atcaaaatat   75960
gtaaaatttc tgacagcatt taaaacatat tcccaggatt atattgtact ttttgttaaa   76020
tcattaattc aaatatttgt tgaggcgtat tctgcttcca ttttgctctt tctgaaaata   76080
atttacaaaa aagctgaagg aagctttcaa ctctattttt gtgaacctgc tttttacaat   76140
ctacctgttg taattttcct ggttttaccc atgctacaag cagagacgat tgggccaatt   76200
agtatactga aattctgttg tggattgtgt tttcaacttt ttgaaaattc ttgatggttc   76260
tagttaccag aggtgtgtaa ggcagaaata ttagctagac ttaagttcct cagatggttc   76320
actttagaat tttaaactat tgtctttcca gactctgaag agtttgacac atttggactt   76380
gcacagtaat aaatttacat catttccttc ttatttgttg aaaatgagtt gtattgctaa   76440
tcttgatgtc tctcgaaatg acattggacc ctcagtggtt ttagatccta cagtgaaatg   76500
tccaactctg aaacagttta acctgtcata taaccagctg tcttttgtac ctgagaacct   76560
cactgatgtg gtagagaaac tggagcagct cattttagaa gggtaagaaa gagctcatta   76620
aaaataaaag ggttgcctaa atatgctgat gttaacaaaa tatgctgaca tttttatagc   76680
aatgagtttt aacaacatgg tgaaactcca tctctactaa aaatacaaaa attagcccag   76740
cgtggtggtg cgcaccttat aatcccagct actcagaggc tgaggcatga gaatcgcttg   76800
aacccaggag gcggaggtcg cagtgagccg agatcgtgcc attgcactcc agcctgggtg   76860
acagaggcga gactctgtct caaagaaata tatatatata tatatataat atatgtatta   76920
taatatataa tacatatatt atatatattt attatatata atacctatat attatatata   76980
tactatatat aatacttatt atatatatac tatatataat acttattata tatataataa   77040
aagaccgagg caatgaatat tacaacttttt atcaactgac ttacatttttt acaactaatt   77100 tttaaattaa tgagtcctct ttgatgctgt tctttgaaag caaattgttt ttgatatttt   77160
ttctttaaag catatgaatt tatgcaattt aatcattatc ttgtctcttg tgactagaaa   77220
taaaatatca gggatatgct ccccccttgag actgaaggaa ctgaagattt taaaccttag   77280
taagaaccac atttcatccc tatcagagaa cttttcttgag gcttgtccta aagtggagag   77340
tttcagtgcc agaatgaatt ttcttggtaa gtgttctgtg tgggtctcct ccttaccagg   77400
ccctctaagt tgtacaagat gagtcatata tggacccttt agttgtggat ttaaaagtgg   77460
catttcagtt taaatattat gctggattta aaaataaaa ttagcaggtt ggcaataaaa   77520
caaaatgcta taaaactatg aaagacatg aagaaacat aaatgcatat tggtaagtga   77580
aagaagccaa tctgaaaagg ctacatacta ttcgttccca actataagac attctggaag   77640
agacaaaatt atgaggacat taaaaagatc aatggttgtc aggggttagg ggagggagag   77700
atgaatagat aaaggacaga ggattttttag ggcagtgaaa ctgttttgta tactatagag   77760
ggggatatgt gccatggtac acttgtcaaa acccatagaa tgtgcagtat aaagaatgaa   77820
ccctgatgta aactatggac tttgagtgat aatggtgtgt caaatattgg ctcattgatt   77880
ggaacaactg tgccaaacta atgcaaattg ttaataatag gggaaaatgt gtgtggggtg   77940
gtggtggtgg tgagggaaga agggatttat tgaaagtctc tggactgtgt gctcaatttt   78000
cctgtgtatc taaagctgcc ctaaaaatag tctataattt aaaaaaatta tcacattttt   78060
```

```
attgtcagag gttaaaatga tagttacttg gcctactgtg tagtaccctg tggttccctt    78120
tagtcttaaa ctaaacatgc acatggctgc ctgagctggg taaggcatcc tgatactgag    78180
atattgtttt tcatactgaa gtttcttcag caacttttg tatgataaat atgattactc    78240
tttgctgttg ttagaaataa aattaatcat ttaatggttt tcaaattagt gaagttaatg    78300
tatattcatt cagctcttgt gctttgcaag acattataat aatgcaaatt attatcatca    78360
cttttattaa aagttgtaga atcccctgcc ttctcttagc atatgaaata atagaggaaa    78420
ttatgttcat ttgtatccta aatgaacatt ttaattttaa ggaacaaaat acttttatga    78480
caataaacag gaattcccca tattttatct tccttcatag agaatactca catcttgcca    78540
cccatgtgtt tattctatac ctgactcagt aaaataattt ttaattctat ttaatagcag    78600
aatatggctt aactacttat taatagtatt ttaatttgtc agagcttttca gaaactaata    78660
atgatcaaag ccatcttaat ttggatagta ttttcctcct tttccgcgcc ctcccttcct    78720
cctaccctcc tgaatattgg ccactttcca accatgatct tgaaactggg gatagagttg    78780
ttgactcact cactagtaag caaagcaaac tcggtctctg tccttaagga acttgtgatt    78840
aagttcagag cacagacaaa cattaagtaa tgatggcata aataaatgta attttatatt    78900
gtggtgcctt ctgtggaaaa gtttcaggat gctctgtggt acctcagggg aatctgattc    78960
agactgtgga gtcaggaaag catttctgtg cctgtgacat ttaagttggg tctggaaaga    79020
ggagcatcca aaaggacctt gaagcttgtg tatggtcagt gtgtcatctc agctgaatct    79080
cacaatgatc ctaatggtca tacctaggac aggtatgacc tctgcccaat tgaggaaatt    79140
gaagccgtga gattttttgt gtgatgctta caggtgcata caattaatta tcttgttgtg    79200
aaagtttgaa tggaccccag ttcaaaatct gtttgctttg cactacacaa tcttaatagt    79260
ttgagaagtg gtcttacatt tgagaagatg ccccatggag gtgacatctg agcaggacca    79320
ctaaccatta aaaataatc ccatgtaaat ggtgaaaccc tgtctctact aaaaatacaa    79380
aaattagctg ggtgtggtgg cgtgtgacta taatcccagc tactcgggag gctgaggcag    79440
aagaatcgct tgaaccaggg agtcagaggt tgcagtgagt ggagatcagg ccacagcact    79500
ccagcctggc gacagagcaa gactccgtca atcaatcaat caaacaatca ataaatccca    79560
tgtaaaataa agttttagtt ctgtggcctt atgagtgttt tccatacagc atatgaaact    79620
caagactctg aagtcttaag tggagaatca tttcgattca tttattttgc gaataggtga    79680
ggtataatag ctatctttct gcttctcagg aagacagctt ctaggagtgt cctggaacat    79740
tttgacccctt gaagattgtc tagataaaga ataacccata ttttaacct tgaaaatgct    79800
aataactaat tcctcaatcc gttttcctag aaacggtaga tttgtagatc tctcaagtgt    79860
cttagtgttc atctgatcta gctacactct tttacagata agaaaagaga ctgtgtgatt    79920
ttctgtttcc caaattgtgt ttcacagaat tttatttctt ggaggtacct catactgcat    79980
ttccttctta acaattcata aagtaggcca ggcacggtgg ctcatgcctg taatcccagc    80040
actttgggag gccgggcgg gcagatcaca aggtcaggag atggagacca tcctggctaa    80100
catggtgaaa ccccatctct actaaaaata cagaaaatta gctggacatg atggcacctg    80160
cctgtaatcc cagctactca ggaggctgag gcaggagaat ctcttgaacc tgggaggcgg    80220
agattgcatt gagctgagat cacgctactg cactccagcc tgggcaacag agcgagactc    80280
tgtctcaaat aacaataata ataataaat aataaaaat aaaaaatca taaaatatac    80340
cagagtattg agaactcaga tattttactt tattttactg aatgtttccc aatctcttaa    80400
gattatatga tcgaagaata cttttattaa ataacaccca ttattattcc atagaacact    80460
```

```
ctttatgagc tagtaccata aagaattttt gtccttataa tatactgtat tttagtaaag    80520
tgttcatagt tgttttgcta tagttattta agagtaattc tagttaatct atatggtata    80580
taataacatc acacataatt tgaaatgaat attctaggaa tttttacttt gtacaaatgt    80640
tgggtagaca aatttatatt taaatagctg tttagcttcc aggttaaaag gttctggtaa    80700
gtatagcata ttattttatt gtttagtgga agtattaagg ctattacctt attttaaaa     80760 gtggattttt aaaaattgtc agtgtgagaa tggaaatcaa attaagtgac acactattgg    80820
tagctgttct tattttgaa tttaatggaa atctggttaa aatgattaaa atgtttatct     80880 cattttttt cttttagctg ctatgccttt cttgcctcct tctatgacaa tcctaaaatt     80940
atctcagaac aaattttcct gtattccaga agcaatttta aatcttccac agtaagttta    81000
ttgttatttt aattttaaaa gcacattagc tggaacagaa cctttagaaa catgatttcg    81060
atttagtcat atagaggtaa ttgatttcta aacctactca acttgatgtt tttgtatgta    81120
tgaatgattt tcactagata aaagacccaa ctcattactt aaaatggaaa ctttatatt     81180 tatttagtgg atcattgtgt aaaaacaact taagattgtt taattaattg ctgtattagt    81240
ataatgaaat gagattatac tggctatcac tttaactttt aaaattttaa ttgtttgtgg    81300
aacttgatat gttgccaaaa taccctttaac tttcacatta tgcttaagtt atgtttgagt   81360
gaaattttgg gggaagatta ggcaagttta tgtagttcca ggttttttgag atattttggt   81420 taattcatga aaccagaagc ttcctgttaa ctttaaaattc aggcattaat tggatcttga   81480
gtgtgttgta atcttaaatg ctattctaat tatatcatac atgataaacc aaattcataa    81540
aaatatatgt gtaaatttat cttttccttt gttttcttgc tgtcagctat tccttcaaac    81600
actatggctt tttagaattg acactaaaat gctgcttgca tgatgctgca atgagctctt    81660
ctgtgagctt atatttaggc aaataataat tagaatttag ccatagagag tgttacacaa    81720
acctataata gctaaattac gtctagcttt agaatgtgtt taactgttct aactactcta    81780
cagcggttca tctctttaat cttcctaata atgccctacg atagccactg ttattatctc    81840
cacttcataa gagatgaagt aacttgccca gagtcatagt tcttaaacac tggtggttca    81900
acttcaggct ctcaaatcac atgcatactc atatgtcaat aatgctagtt ttgacgttac    81960
actttattct caccctgggg aaaattattt gtgatgttat ttcatgtatt ttggaaatac    82020
tcatttggtt tatgtctttt ctgtgtattg ttttagcttg cggtctttag atatgagcag    82080
caatgatatt cagtacctac caggtcccgc acactggaaa tctttgaact taagggaact    82140
cttatttagc cataatcaga tcagcatctt ggacttgagt gaaaaagcat atttatggtc    82200
tagagtagag aaactgcatc tttctcacaa taaactgaaa gaggtaagac gattattgcc    82260
acttaaaaaa tatactttat gatttgcatc attacaaatt atcatttaa gtgatattta     82320 gcttctaaat accaatttca tgaaactaga agcttcctgt taactataaa ttcctgtcaa    82380
ctataaatcc agatttccat taaatttaaa aataagaaca gctactaatg atgtgtcact    82440
taatttaatt tccattctca caccgacaat ttaaaaaaat ctactttttaa aaataaggta   82500 gtagccttaa tacttccact aaacaataaa acaatatgct atacttatca gaaccttta     82560 atctgaaagc taaacagcta gatataaatt tgtctaccca acatttgtac aaagtaaaaa    82620
ttattagaat attcatttca aattatgtgt gatgttatca tataacatat tatagattaa    82680
ctcaaattat tcttaactgt tacttaacta tgacaaaaca acttagaacg ctttgctaat    82740
acacaagata gtataaggat aaaaattctt tatagtacta gctcataaag agtgttctat    82800
```

```
ggaatagtag tggatgtcat ttaataacta taaattcaaa ataagcattg taaatatcaa    82860
taccattcaa ttttttttg tttttaaac aagttgtaag cctaccctat ggtaaatgga     82920
tatggtaaca cagcataatt tcctcaaaaa attacttttg tgatatactt ttaaaggatt    82980
atatgaatat atacataatt atagatgaat gtgatgctgt gtgtcattgt atcaccaaat    83040
ctctgtccaa tctgttaaca gactcttaaa taaaccattt ttctcaagtt gttactggcc    83100
tgtatactgt attacttgtt tttcagcttt ccttggtaca ttcttaaatt tctgcattcc    83160
gccaccatgc tatcacccta atggatcaac cttttttgtt ttgctccatt ctctctgttg    83220
taaatctgaa attgataatt tgtttgtctc agaaaatatt attttcaag ttctagcgta     83280 ttgcctacaa aaccaaaag aattaagtgt ctgacactgt gaggttcagc aaaactgtgc     83340
atatattttg ctacctgatt ttttgccagc aaatgagtgt tttctattat aaatatagta    83400
tatattgctt aaaaatttgg aacagaaaag aaattactcc aattaggatg ccacctaaag    83460
tataagcatg tagctgtact ttgagaacac taaattgcat gcaggtttgt agtgactagg    83520
tcttcttgcc tttactgaag gagcagaatg aagtcacaga taatggataa ccaaatccat    83580
tttgtggtaa gaacttcctt actttcaatg tcttgaagag atgaagtatg ttaccaaagg    83640
agattgggtt ttttaatatt acagatgagt gacatagatt gtttgggagt aagttttat    83700 atgtaagttt ttatgttttt aaacacatac tgcaacctta tgacaaacct ttggaaagtt    83760
ttaaaactct gttgaaaggt tgtgcaagct gctgatggaa tctgtgagcc tttcttgttt    83820
cttatcacgt ttttggcag agcacatttc ttccttccca ccaacaggtt ttgccctttt     83880
ttttcccatt aagattcctc ctgagattgg ctgtcttgaa atctgacat ctctggatgt     83940 cagttacaac ttggaactaa gatcctttcc caatgaaatg gggaaattaa gcaaaatatg    84000
ggatcttcct ttggatgaac tgcatcttaa ctttgatttt aaacatatag gatgtaaagc    84060
caaagacatc ataaggttag ataatttttt tctatttggt tttactaaat ttatttcaga    84120
ttttctactc tctgtgactt tgatggacat atattgttac tatttaggga aaaataaata    84180 gtaaatttg gcattaatat gctgtgtgtc atttgccttt catttaatga atgtgtttct     84240
gtggtgccac tgtagagatt tctcattctt cttagccaga ctaatgttga gagcggcttc    84300
tcctccttct gtttctttc agtggagtag actctaaaag aaaataagta ttgctatttg     84360
gtctctggtt accaattaca caatctaaag aaatacagca cagtataata acttctcaca    84420
ctgtatttca tatagcaact agttaacata tgcctcttac atcttaaagc attatagcta    84480
ctgacatcat gtgaaattac taacttctat tttgcccatt aggatgagta atctactcac    84540
cttgatcagt tttgaaagca ccaaaacttc tcaagtatca ctgtttctgg tctttacact    84600
ttaagcactt taaatatctt tggtaatgga ttttatcctc cttttttgttc cctttcagca    84660 catcggtctt attactttct cataaaatcc tttgctccct tttccacagt tactgtatta    84720
acgttgcaga cctcagctct gtcatcacct ctcaacttga ctgtaatatc caccaaggca    84780
gagaccatgg ctgtgttcac tcactattca aatcttggca cccaacacag tgcctggcat    84840
acaattaata gttgtttaat taccagtgat ttatacttac tcattctctt ctgcctaaaa    84900
tctcttaaat ttatatttaa cttcatctgt ttttatgagg aaggattttg ttttctgaac    84960
tcctgagctt gatttcattt taaggagtt tgttatcttt tgtgctaatt gtggctaccc      85020
ttcatcctac ccaattattt ttctctcttg aaactggaaa agatggtcat ataaaaattg    85080
gttcagttct tactaaacat ttagtagaac tagctttcag tgtattatac tgtattatct    85140
aactaaatat ttttaatatt taatattta a tttaatatat aactaaatat ttttaaacat    85200
```

-continued

```
gtttaacatt ttcagaaaag acagaaagac ctagagcaga ttagaaattg taggcatcat    85260 ttgcttttg  aagaaagaca ttttttcaaa tagtggtgca ttcttaagaa ataaatcaag    85320
aaaggtaatg ttgcttttg  gtcatatcat caggaatgtt ggtcagattc ttattagtta    85380
caggaatgaa ttgatcacta ctctgatgta aaattcactt atgatttagt cttttctct    85440 aatttgaaac tgtggcaaca ttttaacata tttcaaaata tatctttctc tatccattat    85500 attttgata  acactttgac tctactatta gtttaaaggt ggttttttag ctacctaaac    85560
acttctattt cattcaggtt ttacattaag atcattagga atgaaagcta acatctgctg    85620
atagtataat agtttatatt tatttatgat gttatgtgat ctcactatcc atatatacta    85680
ttatatgcat atgtgatata catgaatata tagctataca tcatatatac catatatgaa    85740
tatatacaca cacatatata atgtaactaa tatgaccta  ttatcaagct ttaacagtat    85800
acatatatct ctaccttgtt tctatgtcat atggactttg tgaaattttg aactttataa    85860 tttataggt  ttttctttc  ttttcttttc ttttttttt  ttttttgag  actgagtttc    85920 actcttgtca cccaggctgg agtgcagtgg cctgatcttg gctcactgca acctctgcct    85980
cttggcttca ggcgattctc ctgcctcaac ctcccaagta gctggaatta caggcacctg    86040
ccactgttcc cggctacttt ttggattttt aatagagacg gggtttcact atattggcca    86100
ggctggtctc aaactcctga cctcatgatc cgcccacctc ggcctcccaa aatgcaggga    86160
ttacaggtgc gagccaccgc acctggcgta taatttgtag ggttttcat  actatttaaa    86220 gacattagaa tatgtataca tgtatgtata tgtgtgtata tatagaggta tatatatatt    86280
gcatatcgta ttctaattag tattgcaaac atatttggc  cttttgatta tttctggtga    86340
tagtgtaaca tgtttctttt ggtgatttta ccaaacatta tcaactaccc taaaatctct    86400
agcaaaatat atgcattaac agtactctga aagacatgta cattattagt tatatgagat    86460
atgcactctt ctggatacta tattttagaa tagtgtgaca tgtaaagaa  ctcacctaaa    86520 tctcaagtat acttttaagc agtttattat tttatttta  tctttcaaat actaggtttc    86580
ttcaacagcg attaaaaaag gctgtgcctt ataaccgaat gaaacttatg attgtgggaa    86640
atactgggag tggtaaaacc accttattgc agcaattaat gaaaaccaag aaatcagatc    86700
ttggaatgca aagtgccaca gttggcatag atgtgaaaga ctggcctatc caaataagag    86760 acaaagaaa  gagagatctc gtcctaaatg tgtgggattt tgcaggtatt tctttctata    86820
gaattttaaa attcactttt accatttgtt tggaacaggg attcaaaaac tgagctttct    86880
gttctaatat ccagaaacct ggtagactgt atggaattat tccaaagccc ttcatttctc    86940
ctaattttac ccttgcctcc agaatggaga agaacatgga gggatatgtt aggaacaatt    87000
tggtgctagg tactttgatc ggttgctgac aaatatgcta aaagtggtca atcctagtaa    87060
aaacccagaa tagttctcta acatggtct  gttgtttttc tcttattagt atgctaaata    87120
ataaatagta ttattctccc agattttttt ttaaaaagg  attcttgcct gtcgtttgaa    87180
agattaaaaa aatttgtctc taatctttat ttaggtcgtg aggaattcta tagtactcat    87240 ccccattta  tgacgcagcg agcattgtac cttgctgtct atgacctcag caagggacag    87300
gctgaagttg atgccatgaa gccttggctc ttcaatataa aggtgatttg ttctgatcat    87360
ttgaaaatag aaaataattc atgtgtctgt gtgcgtgtgt gtgtgtgtgt gtaagttaat    87420
ttatttgggg caaacaattg cttcagtctc tttaaatact tcttaaaag  aagcactaaa    87480 attttgaatt gggaaacttt ccgagtaatg aagtcataac atgaaaattg tatgttccat    87540
```

```
gttggtgaat gttattggta acctgaaact cttttatgct gtaaaacttg aaaatatata   87600
tgttcaactg ttttttaatt atattatttc ttaaatgaaa tctaaatttt tctaatttaa   87660
aataagctat attaaagaaa agcaatctat atatatatat ctcatcaact ttgtactcag   87720
gggccattta gtgtgaaatt cttcagattg tatcctttaa gtggtcccag attattatgc   87780
tgttacatct ggaatctccc ttttgttgct tttctatctt ttcctttgtt gtcttgttgt   87840
cagctattcc ttcaaacact atggctttt agaatggaga ctaaactgct gcttgcatga    87900
tgctgcaatg aactcttctg tgcataaagt ccttaaaaag cttgtgtcag gacatttaac   87960
catgtaattg gctgcataca tgcttgtttt gtaatttggg tatttttaa tgtttctttt    88020 attaactttt ttacagctag ccaacgtgag caaatagtac agtggcagtc atatttgctt   88080
gagtggcttt tattctttca ttgtagactc caaattggtt gacttaaaaa cgaatttaga   88140
agattaaatt cacagataag gaagagaaaa tataaactat atgacgttaa tttgatataa   88200
tttgtgggtt tatgaaatgc ttatttatt taggagtgaa taactcatct taaggcatga    88260
agatgggaaa ggaaaactat accactaccg ttatatatgc cacctaaaag ggtgaagaat   88320
tgggttaaga aaggccaaaa atgacttttt aaaatgtcgt aaggttacat ttttttctta   88380
ggtttaagga aaaaaggaca gttgttcttt tcttcttctg aagtctgcta gtttctcttt   88440
tccattcaag tgaatgtcac ggaaagcaaa tatcaacagg aatgtgagca ggcccagttt   88500
gaaagcaaac acaagagggt tttgtgtctt tccctccagg ctcgcgcttc ttcttcccct   88560
gtgattctcg ttggcacaca tttggatgtt tctgatgaga agcaacgcaa agcctgcatg   88620
agtaaaatca ccaaggaact cctgaataag cgagggttcc ctgccatacg agattaccac   88680
tttgtgaatg ccaccgagga atctgatgct ttggcaaaac ttcggaaaac catcataaac   88740
gagagcctta atttcaaggt aacatggtag gctggtagaa aaatgtaatt tattgattct   88800
caactgccta gaaatgtcag aaattttgag aagtgagcaa ctcacttaaa attgtgggtt   88860 ttcttttcctt gttgctgtta gcattattaa agtccttttcc attttaaaat tatttatgcc   88920
agacttcatt tctaattcat agaaatggga acaaaaaata attagaggaa cctgagagaa   88980
actaagagac cgtttctggg atactgagaa aatgttctg agagagaatc tgagaaaatg     89040 ttttttgatgc cttttctgat tcaacttctt atagtggtga ttcaatcaca agggtaaagg   89100
tgaatactga ggtcttggga tcatctttct tctattattc tttaactgtt attttttccat  89160 ttcctcttttt cttttggaat tcctgttttta tggacatctt gatcttttgt gccactcatt  89220 catgaattt gtcactgtga ttcccattcc aattttttc cctccgtatt gtgaggcagc      89280
tgttttattt agtcatgaag accactaact tggttttcag cagtgtctca ctaattactt   89340
agttcataca aaatgggctt tttattttag gaattatgtt ttaaatgttt aaagttatct   89400
tctcgtaagc caaattttta taaaatgtaa ataaatcagt tatcagagag aacactttt    89460 tttttaaata cttggcagaa aaagaaatc ttcactgggt actacaggga gtgtggtgta    89520
aactgtactg aaaaatacc ttgatagttc catatgacaa acataatgat gaatttcact    89580
tagtctgtct tggcttagct caatagcact aatgatcaag atactggctg ataaatagag   89640
tcctatttgg cctgggcagt cccagcataa ttatgtaata gtgtcccact atattctcaa   89700
aagcattcca atttggatga taaattatat agtcaccttg gttataactc catgctggcc   89760
agttagctta gttctgttcc atttatatag attatgtgtg cttcactcca aaacctaatg   89820
agccatttgt aaaagtgatg gcttttgcgg tgcccaggga gagaattttgt atgtttgtat  89880 ccttcaacac acatttatta cagttattaa aaggttttat tgatgataga tggtaatgtc   89940
```

```
atgtaaaaat gacatattat ttatttgtag actttcctat tctcttgttg gacatgtaat    90000
tagaaactaa tatgacttaa agaaaaacaa atacacaaaa tttattcatc caattaatct    90060
cttaatccag gtgttttttt tttctgagac tatacccata cttcaataac tttgttgtta    90120
ctgagaatat tttgagtttc ccttttttgtc attgttgtca gagaatgtat catatcttta    90180
aaaagacttg ttggaggatg agtttgtttt gaaaaggcct gaatttagtt gatgcaaagt    90240
cacagataag atggttcatt aagctgtatt aatactgctt ttgtctaata gatatcatta    90300
ccaataagtc agactagttt ttcttttggc acttataaat caccttttgaa gacaactttt    90360 tacaaggaaa taaaacaaat gctttgagaa ataccagtat tattgaaaga aaagtatata    90420
ttgctaatgg atgcagcatt ctggcataat ggtttgaaaa ctcatttgat tgctttgtag    90480
aagaatgact ctttcagatg acccagggcc tgtgagcctg ccagaacttg aaaattcttt    90540
cttccctgag gtgcttcaac ctgaattcaa agagcagctt ttaatctatt agagatcatt    90600
ttttgtcctc tcatttattt ttcatatttg cctttgatct tagctcttct ctaatctttt    90660
tctgtctcaa ccttattaac aggtgtctgt gcagacactt ttaagttttg ttttttggct    90720
cagcctgtca gttaactgat aatcatgctg aaaggagaag caggacaaaa cagagttcaa    90780
tgctgacaat actcctttta atcttgtcca gcccattagc agagcaggca tctctgtggg    90840
ccttgagacg tagtcccgta aaactcatcc cgtttctact tgatttgctt tctttgagaa    90900
ctcttgttta tttttatatg gaggtttcct gccttggatt aaaacataaa cctcaatctg    90960
aagttcaatt tcatcttaat ttatgaacga ctaagagagg gaacatgaaa agtggaggtt    91020
agtgaaatta tctctaattc tctgggttaa gagatacatg aaaacagtct cttgagtaac    91080
catttgcagg taaatatgga agtaatggtt atggttgtct ctttaagttt ttagtcacaa    91140
gtagaaaaag accaagttaa ttttttttctg tgtgtgctga atttctattt gtagtaagtg    91200 taagaatttta agcagaaatt ctgattcgta ttttcagata aaaagaatat gtaatttcca    91260
taggtccaga aatagggaga gtttgccatc tggtggttct taacggcact ctggatatta    91320
ttaagagttg catttctatt taaaattata ttttaaaaaa cgtttggaag atactttttat   91380 tgtagaaact atcctcttag ggccattctt taaaaaaatc ttatttttata tatttctcat    91440 tttgttgata gtgattagat tctaagagca acagaacaat gatcatcctc tcctatcaga    91500
atcactgatg tttagatgat ttctcatttt cccaagttca aggttccatg aaaaacatag    91560
cttgagtggg attttatgtc tctgcgtttc actgttgata tatatgtcct cccaatataa    91620 catttttacaa ataaccaagc acaaaattta atatttacc ttgaatattt aaaatataat    91680
aatatccaaa agctcttgta atttgtactg atatcttata ctagcgtgtc tgtttcacat    91740
taagtttaat gtcttaggat ataaaaaatc ttttttatgg ttagtgatttt atcttgtttt    91800 ttttttccatg gaatttctgg atagcgagat aaatatttcc atactatttt atttgatatt    91860
tccaaatttg cctctgaatc aacaattttc ctattttaat ttcattgtac ttgttccttta   91920 caacctaaat agctttttat tatatttttga tttatttttaa aaatgtactt ctgaataata   91980
tatctgtttc tgtaaaaact gttagcactg aatttgccaa ccatttgaca aatacacaaa    92040
taaaatagat ttttacggct tgtcatttgt aatttcatag atccgagatc agcttgttgt    92100
tggacagctg attccagact gctatgtaga acttgaaaaa atcatttttat cggagcgtaa    92160 aaatgtgcca attgaatttc ccgtaattga ccggaaacga ttattacaac tagtgagaga    92220
aaatcagctg cagttagatg aaaatgagct tcctcacgca gttcactttc taaatgaatc    92280
```

```
aggtttgtgt ttttcgttcc ttattttcaa agctcagctg tagtaactta taaaagtgtt   92340
tctgaatctt ttatagaatt tacattcaaa gttgagagaa tatccatacg gttctttaat   92400
aggccactga ttttttctt tttggaagat catcatgtgt gttcatgaca aatcatgtat    92460
catgtcataa gaaaacaaat ttagaaatca cctaggagta aagcagtgga aagagtccct   92520
gagtgggagt taaaatattt gggttctaga acttgtcttt actattcagg agctgtggaa   92580
ccctgaatag tcaaatgaca ttcataatgt caaatgagtt tagtgcatgt gaaagttatt   92640
tttatattgc aaagggaat tattgttggc atggtctaac tgggacgctt ggagagtcaa    92700
tggctccctg agatgatgca gcttctgagt ggaagatcta gctctcttgc atcaaatatt   92760
gatctcaaag atgaaaattc tcaaagcaac ttcagtgcta attgtgtact tgatcatatt   92820
accttgctag aaatgtgtga gttgtttgat agtactagag taagtgactg ggaagctgct   92880
tttgatccct agattctgtt gtataaaaaa tagcttcccg tggtttatga tctgttcctt   92940
ttccccatcg ttcttaaggt atgctgagat atgctgtgtt tcttatctgt atttgaaaat   93000
aaaacatgtc tttgtagtgt gtattcagca agcgaaacag aaaattatga atttctactt   93060
atgtgtgaaa tatgctctgt aatgcatgtc agtgtctcaa atatgcttaa atatgatcat   93120
tttatgtagt ttaaaaatac tccattataa tattggaact ttagaccata ggatgcacag   93180
cttctagtcc cagctctgtc actagctatg ctgaaatttc ttcacctgca aaatgaggaa   93240
gttggactag attttttcta aagccccttg atatttgttc tagattccat gtttcactgt   93300
ttgatgactt tttactacag gagtccttct tcattttcaa gacccagcac tgcagttaag   93360
tgacttgtac tttgtggaac ccaagtggct ttgtaaaatc atggcacagg ttggtgtctt   93420
ttatttttgt ggcacggggg ttatggtcaa agcatagaac agatggcgcc cagagcattg   93480 agcatttag aatttgggtt tagttaaggc agaaactttt gtgaatttgg aaaactgtgg    93540
aacatttcac atagaagact acttgaagag cttcatggaa gaaggaaaga tgtcttgagt   93600
tcacttccat gacttggttt tcaagccaca tacagatgtt tgtatcactc tgccccatgc   93660
tgctttacta gatcctgatg atgtcattgg tttggttact gaattagtca attgaatgat   93720
ggctttgtgg aaatccttgg ggtaaacaca tataagaaaa ttaggttgct gagcctgtga   93780
aacctctatc tagataacat ggaggtgagt tttgacttaa gtgaaatgat ctgagcttta   93840
aatgcttacg attttgaaaa ctttggatgg ccttggttat agctattttt ttcttatatt   93900
tcacatggaa aatgattttt ttctccaaat gataatccat taccaatgag tttaattagt   93960
tataataatc catctctgta gctttgacat aaaagaccat ttgagcaaaa catactacct   94020
cagggctttt caaccccagc atgatgacat tttgggccag ataattcttt gttgcacatt   94080
gtaggatgtt agcagcattt ttggccttta tattcgagac gtaagtagta tcctctagct   94140
gtgacaagca aaaatgtatc cagacattgc taaatattgc ttggagaatg tgaaaaatta   94200
ccctagttga gaaacattaa gctactgatt tgttgatgag taaaatttat agttttgcat   94260
gtggctgccc gagttcctaa aattattata tatttttatg ttagaaatat ctcttccaat   94320
taaaccataa aggtaattaa attcactcag gcagccttga ataattgttc ctaaattcca   94380
tctaaggaaa aaaaggaagc tattgtgaag agagaactca gttgaggcta aatcctgtac   94440
catggaactc aagagcatat tgaaacattg caatcagcaa ttatttgcag tgtgtcagtt   94500
attactattt tggtaggtat ttttaaatta gattttcagc cttctgcaca tatgtcatgg   94560
ataatgtgat tttactcaat tattaaatga taatggagac agtagtgtga cccagagcac   94620
ttacttgagc atcagcttga cctacgtttc agtctcttta attacttatt agctctgtga   94680
```

```
aatttcttaa tgcattaagc ctttgtttac ttactttta aataaggaaa ataacaatta    94740
tcttctatat tgcctccctg gttcagtgta agtgaggggt aaatgttagc taattttata    94800
ttggatctat ttggcaattt aaagaatgtt aatcaggaaa ttttaaaaaa ttcagaacta    94860
taaagaggta cttacgtagt tttggaaagt gtgtcatgta tggggacaaa taaaaaagat    94920
gtgtaggtag ctgcatcctg tacagcaaag gaagttttaa atatatccag caattttgtt    94980
gtcctagctg gcgcacaata gttatcagga ggtaactcaa ctccacatag tcaaggaaaa    95040
gctaaagttg ctctctaaag tggtgtgttt ccatgtcact atggaacact tgaagttgca    95100
cacatgtgaa cattaggatg ggtatatctt atacagtaga ataaggaaga ggtttgcatc    95160
agaactcccc ttttaaaaaa atgcagattt tcactatgac tgcaataaaa ttcctgaaga    95220
ttctgtggag taattaagtt gaaactccat gaaagttctt ctcattagca tagttataaa    95280
tatgataatt taagtaaaaa ttaagttaat ttgagccact caaagttact tttaaagaca    95340
gatttaaaat gtcaataaaa tgataattta aatttccgat taacctaaaa aagaagtgcc    95400
atcattttta tttatgccaa taaattgaaa tataatgtca ttttatcact aaggtttaaa    95460
ggaaatgaaa tctctaaata atcaagtgaa accaagagca acttgtctga cagctattag    95520
caaaaataaa taggagtatt caccttcatg aatcaaggca agggccggaa taatttcatg    95580
gtgcagaagc tctaatgagc ccacccactc tatgcgcccc gagctgttag gtcactaaac    95640
ttattaaaaa aaggtaccat taaggcaggg agaagtttac aagactcatt taactgtatg    95700
ataaaagaga tatgaaagag acctattcaa ttaatcaggt ggaacattaa aaagcttaca    95760
tggcaattta accttgataa aaatacatgg gagaaataca aaggaatttg gaaaattctc    95820
tttccttgaa taaggcatca gttagctatt caggttatga ggttaaggaa atgttaggag    95880
ctcttttaaa ggtgataaag tcaagataat gttgcagatt ttattcttat gtaacaaacc    95940
ccctcgaaac ttggaggctt aaaatgtgaa caatttatca tttctcgttc ttctgtggct    96000
tgactgggct cagctgcgtg gttctgctcc acatggtatt ggcaagggtt attcacttgg    96060
cttcattcat taaactgagc tggaaagtgc aagaaaggta catgcatgtt tttggagtat    96120
tggtgcttct ccatgtggcc tatcatatgg ctaagttggg cttcctcgtg gcacggtgat    96180
cacagaataa ttagacatct ttcatggtgg ctggttacca agagaaatga agcagatttt    96240
ttctgtcctc ttaaaggcta ggccaaggac tggcaaaaat attaattctg ctacattcta    96300
gtaaccagag caaccacaaa cctagctcag attaaggggg aaggaaaaga gactctatat    96360
gaatagcacc tatgtatagg gatggaaatg atgtgtccat ctttggaaac ttccactata    96420
aatagtggta gcacgctata gatccactag gaaaatcaag cacaaactct ttaaaaaata    96480
agtgtatctt agtaaaatag attagaataa ctagataata atggctaaca tacatgaggt    96540
taatatgtgc ttttcaaaga ttagctcatg taattctcac agcaaccttt ccaaatggta    96600
ctttattagc ccctatgata cagatgaaga aattgattga cagagaggtt gaataattta    96660
tccaacggta cacattcagg aagaggtaga gttagaattt caaaccaagt agtttgactc    96720
cagggcctat gagtttatac attcataggg ctgatattca aatgagagaa gagaagtaat    96780
aaataaacat ataatatgtt gagtggtaca gagtgctaca aagaaaatat gaagtgcagt    96840
tggagatgaa ttgtcaaaaa aggtcttagc acttaaaaaa cactaaaaca gcaaacaatt    96900
ctctttacca cctaaactgt aagagcgatc tggaattgct ataagtacaa caacatggga    96960
gaagtcttaa acaacagttt ttattattta taggcccatt gcacactgtc attaaatacc    97020
```

```
aatatgttca atcaaccatg cattcattga ttcaataaat actgtacata caaaatagaa    97080
atacagaaat gggtaagaca agtccttggg cctaaggact ttataacctg gtatttcact    97140
caactacatg atagcataaa taatgtttgc ttctgtttaa gtattcctta aacattatag    97200
atctcccaaa gaaaattaaa tacaaacctc tttttaaagt gaatttgaca aagcaaaata    97260
aattggaata tatagataaa tatgctaaaa tttgtcatat gtactttgcg tactttacat    97320
gtgttatttc attctcaggg caatctaaga cagtcacttt tattatctca ttttatagag    97380
aagaaagctg tgcagtaaag aaatcaaata cctttcccaa ggttacagag ctagtagtag    97440
agcctggatt tgaatctggg ttctgactga ttttaactg ccatgacaag gatcaaagct    97500
caaagtgtga tctctgtgtt agaaacatcg gggttgctct ttaaaaagc cgattctcag    97560 gcctcaaccc agacctactg acccagacac tgcaagtaga atccatcaaa atgcagtagt    97620
tactttgaga atcatgaaac tctgctacac agtctgtctt cctattcatg gaagtcctct    97680
cctagtatat aaatgtgaag taatatttct atttcaaacc tgtattgata actgtctgga    97740
agataatttt cctgggaata tattattgat gagactgcaa aacagatgtg aggtattgga    97800
ttgatctttc cattgtagct agggaaatac tgatgttcat tgtttcagtg aagttcaatg    97860
atttcctatc cgaattaact cccttaattt aacaattttt ttttttttt tgagagtgaa    97920 tgcccctctg ggcttctagg ccacatggtt gctagagaaa ttaggtactg tgttgcactt    97980
gaaaacacta aaatctttct gactactttc actgagcaaa gagacataaa atgctttaaa    98040
tttgcaacat tcagaaaat aaattttagt gattatttat gactcgaatc tttcagattt    98100
tgacagtgaa agtggaaggt tgtccaaaac accctaaggg cattatttcg cgtagagatg    98160
tggaaaaatt tcttcaaaa aaaggaaat ttccaaagaa ctacatgtca cagtatttta    98220
agctcctaga aaaattccag attgctttgc caataggaga agaatatttg ctggttccaa    98280
gcaggtaaag aaaaccttaa aaaattaatt gctacatgga aattcactat ctattctttt    98340
aattgtcaaa ctaactgtag tctataatag atgtattaaa taaataaata tattttgctt    98400
ctagtgtaaa cctcctactg acatgtatca tttattttgg aataaaacat tgcatctgac    98460
actttaacaa tatagtaaat cacttacttt atgtgtatag ttactagttg gcttatcact    98520
gttgaaatta tttaagaaag gtaaatagtg gagattaatg tgtgtgtgtg tctgtgtttg    98580
tgtatgtgtg tgttcttaaa caacactgag agagtttatt aagcaagttc tgagaagata    98640
gtgagttttc aacagaattt taaaagcatt tatggcatca caatggatgc ctatgtttta    98700
gcctatacta tggaaatttt tcctactgct ctaagcaact gggaaattta taagtaata    98760 tgatgttgaa atgtgcaaat tacattgatt gatggatgca gccaattta aaaataaata    98820 tacactttt ttctaggaca tgtattttc aggatttata taagattaca tttgtctatg    98880
cataactaat tgtaataatt tatgtattag tgcacaggga ttaccgaaaa tatttcatgc    98940
atctacatct gagcatgcat ttgaattggt tattgaccac tgaattttg gtgtaggaaa    99000 aatatgtagt gaaacaatgt tacaaaaaga ttacaattgt ttggaatgat taccttcatt    99060
gactttaagc agtaaaatca tttgctcaac aaggttgggt gttttgtgag gctgtataac    99120
catagtgtcc ttttgccttt agtttgtctg accacaggcc tgtgatagag cttccccatt    99180
gtgagaactc tgaaattatc atccgactat atgaaatgcc ttattttcca atgggatttt    99240
ggtcaagatt aatcaatcga ttacttgaga tttcacctta catgctttca gggagaggta    99300
agtatctaat gaagacttat tagattttta gagactatta atttagactt attaattttt    99360
agagaaatta gggagatggc atatgaaaag taatatgcca ttttctcaga gtttacttgt    99420
```

```
ttggaaggca gctgaagaat tagaaaataa gctcataaaa ccttggagta ggcaatctaa    99480
agacacacaa gcacatataa cctcatctaa tttgtcagga agaaaattcc ttaggtgctc    99540
actcagatct tgactgtgat tacattgtag ggactgtaat tatctctttt ctgttgcaca    99600
gccactaaga catttacaaa aaagagcaa atccggtgtt tataatgcta actctttctt    99660
ctaaaataaa tagagacatt ttggtactcc aaagggaaaa tatcattttg gggattaaaa    99720
ttagctttac acaggtgtta ctggtttcca aaataaacct taccttgatt ggaattaatc    99780
aacatatagg tagttacatt gcattaaaaa gttcagaaag ttttgcgttt agcatgatca    99840
aaaacttctt tttaaaaatt atgaggattt atttatgatt ttctttcttc atctgtcgag    99900
catattaaac tgcttaacag catcaacctg aaatggatct taatgtgcag gggatttaac    99960 tcttttatt gtaaagttgt ggataaaata tttaatagat atggatgagg actcatatca   100020
gtaacaaccc aatactttat ttcaaaatga atagatctgt attacaatca cttgtgttgt   100080
gtgcagtaga ttttttccct ttaacttagg aagcagttaa taattaatgg ctccattttt   100140
tagaacgagc acttcgccca aacagaatgt attggcgaca aggcatttac ttaaattggt   100200
ctcctgaagc ttattgtctg gtaggatctg aagtcttaga caatcatcca gagagtttct   100260
taaaaattac agttccttct tgtagaaaag gtaaggaaat caatttgaat gttttcaatt   100320
gcaacactaa agaaatttaa acttaaaaaa aaaaaaaact ttaccttaaa gctttgcgac   100380
agtatgaggt ttagacaagg tgttgagctc tgttttgaat catgtaggct gtattctttt   100440
gggccaagtt gtggaccaca ttgattctct catggaagaa tggtttcctg ggttgctgga   100500
gattgatatt tgtggtgaag gagaaactct gttgaagaaa tgggcattat atagttttaa   100560
tgatggtgaa gaacatcaaa aaatcttact tgatgacttg atgaagaaag cagaggaagg   100620
tatgttttga tacaacttac aaatgctttt aagtgatcct tcaatactta tgaagtgact   100680
tttaataaat gtaaatattc ttatccataa gggatgagtt gaaaaatagt atattcaatt   100740
atagggacag ttcagaaaac tgaattatat ttattaccaa taaaatcttg tattctagat   100800
tcagaaaatg ttgatttgag ggtttgaatg ctggcttatt gagcaacata acctcatctg   100860
tgaaaccgga ataccaacca catctatctc atagaactgt tataaagatt caaatagaca   100920
atacatggac ctaatttacc aacatgtctg ccatataata acagctgcag cttcatgaat   100980
gtggcaaaag cagagagtag ataactttct agtcagatgt ctggtagtct gcagcagttc   101040
agaattctac aagtgaacgt aggaataagt ttttaaaatt ccaagtagat agatactaag   101100
tgaatcttta aaatgttctc aaatttccta gagaaatata ggattggtta gaaagggagg   101160
gattagaaat tatagaaaat attccattat tttttcacat caaaaccaca aatttatgta   101220
tctccttaaa tgttgttttt atttaaaaaa tgttttatta cttctcagga gatctcttag   101280
taaatccaga tcaaccaagg ctcaccattc caatatctca gattgcccct gacttgattt   101340
tggctgacct gcctagaaat attatgttga ataatgatga gttggaattt gaacaagctc   101400
cagagtttct cctaggtaat tcttttttgtt aatttgagaa taaaaattag gatgtaattt   101460
tctccttata atttagaaaa tagatttcat aattatattg tcatagattt tactgtcttc   101520
atatatttgt tataattttt gtatttggaa tgatatattt taaaggaata taatattaca   101580
gatctggaat ttgttttgca cataatcatg tagactagga tcaagatgag gatgagatta   101640
tcatggaagc agaaatattt atgaaatata tcttttgtatt tgccttaatt gccagggata   101700
tgggaggcaa ataagacagt tttcaggtga gttaagtgaa gcagccatat tttataaaat   101760
```

```
gacagaatag gtaaaggaag cacacctcag tgtagccata gcaggggttt tatgactcag   101820
tgtgacaatg ctgaattctc atagaaatat tcattaaaag ccttgaaatt aaagtcaaaa   101880
gtgttacatg gtgacatact caaatacttt ttttttttt  tttgatatgc tgaacaattt   101940
acatttcttg gttccgtgaa ttcaatcagt gattttcagt agagtatgat ggaaatcatt   102000
gaattcatgt agcatgttta ggtgctcatt gagaaaaggt gaagtcatgg taaccatgtt   102060
tcaatattct catttgtatc ttgacttcct gcacatggat ttttgggcct aaaagatgtt   102120
tttaaaacat gctcatacac ttcagaagat gaaaagtgta tgcattataa ctactttggg   102180
aaagaaacag tcaacatatg ttactgtatg tcattctgta gattacatgt gtggtttctc   102240
atgtctctca gaataaaagc taatgtcttt acaagacctg cgatgctgtg atctgtctgg   102300
ctcctcggtt atcatttta  aaaaagata  tactttgtac aaattttttt aattgacaag   102360
taaaaattgt atatatttat ggtgtacaac atgatgtttt gatatatgta tatgttgtgg   102420
aatggagaag tttagctatt taacatatac attatctcaa atatttatgt ggtgagaact   102480
attaaaatct actctcatag caatttacaa gtatacagta tgttattatt aactgtaggc   102540
tgacatactc aagttttaaa cattcctgag agtcattggg acaactatga aatgcattag   102600
attgatttaa tataaagcat ttgaagacaa ttttgacctt actttgttta gttttttgttg  102660
ttgttgtgtg tatacattta attttaatca aattaccccca gaaataatgc ctaagatctg   102720
tcagtcagga cataatatta ttagcaaaaa gttgtccaaa atttgagaca tgatatttaa   102780
agctaaataa actcctttat accctctta  ttggcattga ttgggaagtt taggttgaat   102840
ttaaatgctt tggaactcag gaagttaatg tattagtaat agtgggttaa cataaaatgc   102900
tgaattgtcc ttgctgaatc ctacatctta accccagact tcaaggtata caggaaagta   102960
ccagacatgg tgcatccttc ctctgaagaa atcccaaact gtcagacaca gatccctaaa   103020
atatttcttt ttcctgcatt aaaatgtgtt tcagatgaat ggacacgttt tgagtagtgt   103080
atgtggaaac gtcatttaca aagtctgttt agttggccag gtgtagtagc tcactcctgt   103140
aatcccagca ctttgggagg ccgaggtggg tgtatcacga ggtcaggagt tgaagaccag   103200
cctgaccaag atggtgaaac ctcatctcta ctaaaaatac aaaaaaatta actgggtgtg   103260
gtggtgggca tctgtaatct cagctactcg ggaggctgag gcagagaatt gcttgaacct   103320
gggaggcgga ggttgcagtg agccgaggtt gtgccactgc actccagcct aggcgacaga   103380
gcgtctcaaa acaaaacaaa acaaaaaaca aaaaagcaaa gtctgtttag ctacccatat   103440
aggaaaatgt ttgtgattac tctcccttct ctagacccat gtcccataaa tccataaatc   103500
ccatgttcat ttacagaaag cagtctagat aggagtttct cagtctttga gctgttgcca   103560
ttttggcttg gataactaac tctttcttat cgagggtcat cctgtgcact gcagaatgtt   103620
tggcagcatc tctgtctatc cactagatgt cagtagtatc tccccttccc tcagatgtga   103680
caatcaaaaa tgtctccgga tgttgccaaa gataaggggt ggggttgaat accagtgatt   103740
taaacaaatt aggtgtatcc ttctaaaaac attttacagg tagcgactcc agcatcttta   103800
tattagagta atctggagaa ggttatgcct ctctcaattt tccctctttc cattttatt   103860
tgtagggcag caatgcattc aggcttttgg taactctttt tcccaagata gcagtaacta   103920
ttatgcagtg agtaatacga cccaccttaa tagatatgaa tagacttgtt ttgtgaatat   103980
atttttaaaat ataatgtat gggattctgt tcatgcgtct gagaagccac agggtacatt   104040
tcctctttgt ggagctattt attttctgg  agagccaaga caggtatttc cacttcagtg   104100
gtgtgatttg aggggttagg aaaatttcct tgccttcaat tttctttcca acctagatgt   104160
```

```
cacaaataca taatagtagt ccttaacttt attttttgttt tcagtcacct gaaagacatg  104220
acaatccata ctccatatta atgcagcggc gattctcaaa tagagaaggg ctttaaaaaa  104280
ttagaaatct ctgccgggcg cagtggctca tgcctgtaat ctcaacactt tgggaggccg  104340
agatgggcgg atcatgaggt caggagatcg agaccatcct ggctaacacg gtgaaacccc  104400
atctctacta aaaatacaaa aaattagcca ggcgtggtgg tgtgggcggc tgtagtccca  104460
gctactcggg aggctgagtc aggaaaatgg catgaacctg ggaggcggag cttgcagtga  104520
gccgagatcg cgccactgca ctccagcccg ggcgacagag cgagactctg tctcaaaaaa  104580
aaaaagaaaa aaaaaagaa aaaaaaaca actagaagtc cctactccaa cttgaaattt  104640
ggatgtatct ccctagagta tgtttcttct ctatgctgca ttgcaatttt tctttgttgt  104700
tgatagttgt ccagattgag gggaggcaga acaagatgca tctatatgtt tccatctctc  104760
cgaccgattc tctcccttcc ccctctactt gctttctttc tcttttccct cttctgttta  104820
cccgattcta tttctgattc cagtatgtaa cagttccctc tgaagctctc tcaataccaa  104880
caatcctaac taatggtttt taaaagtcaa atattaagta ctggagggat agaatgagag  104940
aataccaaga ctgataagat gcaaataata cttttaacat atttacaatc taatagaaat  105000
acaagacatg ctcaaataag ttaattattt taatatactc tctctgagca taaaatataa  105060
ttatatatgc tcattataga catataaaaa ataaataggt agaggctttc catagatgtg  105120
taatttcacc acttgaaaat tactatattt ccttatagac tgttttgtgt gtattcactt  105180
atatccatca agtgactaca tttcaaggca ctatatgaga accataaata ttgtacaaac  105240
aggatttgct aaatgtcggt ggagagtaac agtccacggg gctgatcatg gtcagtttgt  105300
gaggcaggcc tccaaactcc ttggggattg agatgatgga gtagcagagc tcttcaaggg  105360
tatggaggcc tgaaggtaca aagcatgctc aggaaatttt ggctattgcg gtttgtctag  105420
agcacttgtt ctcaacctta cctgctcatt actaattcta ctaagtacag aattaaaaga  105480
agaaaaaaat ctaatgacca tttcctcctg ggactaatta gatcaaaatc tttgaaccca  105540
gacattagcg ttttaaaaag ctcctcagat gtactattca gccaggactg ggcagggaa  105600 agctactgaa ctccagccct tgagaatgaga agtagaacaa gaggagaact ttaaaaggat  105660
ttaggggcca ctatatgact atggagctga atttagattt gatttagtag gcaacgcgga  105720
ataatttgtt tctgaacagg agagtgacac aatcaaagtg gaatgatagg aaaattaatt  105780
ttgcaagaga gagagaatga gttggaagta aggaactcag aaggcctcct gggactcagc  105840
agaaagctct gaggccacca aatgggtgtg gtggtagtgg aaatggagaa gaagggaatg  105900
taaatgaggc tacacagtgg actgccactg ttagccgtgg ggttagacca cagcaagagt  105960
taaaataatt cttcaatttt aactccagaa gggcctcaaa aagacttttt gtcttgttat  106020
catcagctat atggaaggta gaataaaaac tagttaggag aaaaggtaat aaatgtggct  106080
tttgataggc tgtgattgag ttggaagggc ataccagtga aatcaccaac acaaagttgg  106140
aagtgtagga aagcacttag gaggtggcta taagtgaaaa tgtgaaaatt ctctacatta  106200
aagggataga tgaagtcaca gaagtggatg acataattga gcagggtatg tgtagaggga  106260
agacgggaag gttaaggaca aaatctttac atatatcttt cttggagtag aaggaagagg  106320
aaatgttaaa ggagatttga ttcaatgaaa caagtaggtc aggtttctat tcaaatttac  106380
aacagatata attacaacag atataattta tttagttttt ttcgcttgga cagcttaatt  106440
taagtgcttt gtatttttctt ttcaaaaggt gatggcagtt ttggatcagt ttaccgagca  106500
```

```
gcctatgaag gagaagaagt ggctgtgaag attttaata acatacatc actcaggctg    106560 ttaagacaag taagaaattc aataatataa ttatattaaa ttgcacatta ttaatctact   106620
ggaactctta ttttgcatac agttgtgaaa atgcaaaata atgaccacat ttctacttaa   106680
gtttaattat gcaatcctag tttgtctttt cgttgtggag tagaaagttt tgtgttattt   106740
ctcctgttga gaaacaaaac actgtatctg agaatcctta taatcgtgat acatagtgtg   106800
ttgtaaaact ttttgtaaga ctcacttaca ctcctctttt tactttagaa ccttgctgtt   106860
caaaatgtgc tccatggaca agcagccagg cattacctag gagattgtta gaaatgtaga   106920
aacttgggac ttttcagtgc catattattg ttcctgatac tccacagtag tcagactcct   106980
agctgcctcc acctgcttcc agaccttgaa gcctagcaag ctcctgactt cgccttctgt   107040
tttcttcaga gtatttatct tttactttc tggtctaggg agagaatgat ttttattttt    107100
attgaacatg acttctgtgt gttcagggtg aaagaagaag tttaatgcat gatctcacat   107160
tgctaatttg attgaaggtt agaaatctta aactaaaact ctcactgata agcttgcacc   107220
tctcttttct ggatttatcc actttaataa gaactgctat tgattacttg ctacaaagat   107280
ggagaaagtt agcatgctta tcctatttcc tactccctgt ccctgtccac ttcctaaaac   107340
ttaaaattgg ttgcattaat tttcctgata tagtaacaat tataacttgg aatgattttc    107400
aaaacttttg tttttttagt ataccaactc tagacagcat ggactgactc cttgctatgt   107460
gagatgagga aaattaacgc tattcttct ccttttccca tcaccttctc aagttcttta    107520
atttattcta ttatttttat gtagtgaaag tttataacat ttatattctg gtctgtactc   107580
ataattaaat tgttcacatt ttgtctatag tttggttctg agaacaaaac caataaatgc   107640
catttatata tttttttatt tgtacagaac caaaatattt ctacttctag ataaagaaat   107700
gcaaccttct gtcactaact tcttttacta atagaatagt aacattccaa atatcaaagt   107760
caaatggatt ctctattgtt atgtatttat catcaattta taaaaataaa ggcatatttt   107820
aatttggtca catttttacc ctgatttaaa aaaaaatttg ttttagaga tggagtctca    107880 ttaggttgac caggctggtc tggaactcct ggcctcaagt gatcctctca ccttaacctt   107940
ctgagtacca gtggtgattt attttatgta gcttttgag gttttctgat tatatacata    108000
tatttttaaa aaacgtactt caggaaaaga tatatatttt catcatgact tcaagtgttt   108060
ctaagttctt aatcatacag tttgtataac agaatctact ttcttcttga agacattcct   108120
cattcagcac atgacttact gctctaaaca ggagagatgg atttctaggc tgcttgtgca   108180
gtgattaatc tatgagttag tttcctcgcc ctctttgatt actctcaata tttcttggat   108240
tccatccatt ctcttggttg gattgtcctt agttttgtt gaagaatatc ttcgagtaat    108300 tttttaaga aaaggtgttt gtgaggtaaa tgttttcagt ccttacatgt taaaatatc     108360 ttagttttgc cctcccatgt ggtggatatg tcatcacact ttatttttta ggaatctagg   108420
cttgaaacaa ttttcttcaa aatttgaaga aaattccatt gatttttagt gcccactgtt   108480
gctaatgaaa agtctgcagt cagtcagatg tttgctccta tctaggatac ctttaatttc   108540
attttgaaaa ctgaaaattt gaccttttga atttcatttg ttttcagtgt tctgaacctt   108600
tacaagtatg tgtttgtgtg taggttgttt ttcattccat ctaattcatt attttgtgaa   108660
aaattgtctt ctgtgtattc tcttctatta tttattattt cctccctaac atttattaat   108720 cattttatt gacaactact atgtaccagg ttaggtgatg ggacatatga tatatatata    108780
gtagtaagct aaacccagtc aaggctctgc ttctctggag cctatatcta gttacttatg   108840
attcattatt gcttatcatt gctccaagag tatatgttag atgacaagcc ttttgggtct   108900
```

```
atcatccatg tttgagttcc ctcttcaagt tttatctata atttgtgtta cttacttgac    108960
tgtctcttac aggtttctaa tattttttag aattgcatca tctattattt agctttctgg    109020
tgaattttgt tttgataatc atattttcca tttccagcaa ttctttccat ccctctggt     109080 tgttcctttg tagccatgtt tttggataaa atgtccatag gtgtttctgt tcatgtcaat    109140
tagaattttt ttttgtatta cttgcattat tgcttttttc tctgaggtta tttgctctgt   109200
gggttcatct tgatctttct cttttatctt gtcagtttc caaattgagt agttttgggt    109260
gacttcgtat gaagtaagta ctctattgat tgttaaagaa ggactgtatt gattattaaa    109320
ggtaactaga atgggcattc ttcacattca tgtaggtttg cttgttcaag ttaccacttt    109380
ctgaacaaga aggttagacc atagactttt aagggctgca tactgcaaag ggatactctg    109440
ttctttaggt tacatgggca gggatcactg ctgagaccat acctgccaaa ggaaggcagg    109500
ctttgctctc tagatgctgg acttgaaatt gtttcccctc tgcttagtgc tgcattattt    109560
tttttgcttc ttaatctgct gcagagtatc tagatcaggg tgtccaatct tttggcttcc    109620
ctgggccgta ttggaagaag aattgccttg ggccatatat aaaatacact aacactaatg    109680
atagctgatg agcttaaaaa aattacaaaa aaaaaatctc ataatgtttt aagaaagttt    109740
atgaatttgg gttgggccac attcaaagcc atcctgggcc acatgcgacc tgtgggccac    109800
aagttggaca agcttgttct agatacttca gactctgttc tacatctctt catagatcaa    109860
taacttgcag caatgagttt atcagataaa ttatgttcac ttttcatcca taaaaaagt     109920 catgggaggt actcaccata ggattggttt aatccagtca ctctggccaa ttttctttaa    109980 aattcctttaa accttggtat attggtttaa ttccttcaga atggcttttc ccattgtgat   110040
aaactggttc caggcttcac gagtactat tccaagtaca gaaggaaaga gggtacctct     110100
tttgagtact tgtatttcaa aggaatcaaa tggcctacat aataacccat taaataaata    110160
gatgtctctc agccccagtg agtcatctgt gcttttctca acaagcacta tgttcagggc    110220
aatgctttgt gctaattggc tttaggcctt tgttaccaaa ctgatcactg tggccctgag    110280
ggtgctgtta cttagaatat tcccaccttt tctgagaggc tgatgttggg gtcacttccc    110340
cctgaactaa agtccagggg ctgcatgggt gagggttgag taactcagta ctctaaggag    110400
gaaaggaagg ggaatataca ctgttagtta acagtggtta ttcctgtatt ctctcttgtt    110460
tggattctac tggggatttc tttctttttt tgagtctttta ttgacattag gaatgagaga   110520
tagaaacagg gtgagagagg aagtaaaatt aaatgtgaat tcttccatct tataccagaa    110580
ctcaactgta ttttttggaat ctatatatcc ttacttttcc cttgatttat tacaaaaaat   110640
tcttagtggc tacactaagt aaattttgta accttttaaaa aatacatagt tataatattt   110700
taagtactct gagtaataga agatttcatg tgagtacaaa atatcctggg ggcattttaa    110760
ttattagtaa caacagtcac actgtagttc tagaaccaaa ttgaacattt tatatataga    110820
agcttatctg tgaatcaaat ctgacataat ctcttttaat gtgtaggtaa tttcttatat    110880
aaattgattt tttggccttg ctgtcagcat gcatttcaaa ttttacacca tgtgtttggg    110940
gagctatggt ggaaattagt acattaaaaa tgtctacaga gccaattagt gtataagcag    111000
ggaggcaaac taagggaatg gtggaagaaa ttaaaaaaaa aggggtgtgc ataatgtgct    111060
tcttctctta aaaaaaaaaa aagaaaaaga caacaacaaa aagaaagaaa aatgacattt    111120
gacggtcatt ctaccagtag tcatggggca gatctatatt atactgtact attacgctgt    111180
tttttctttg caattagtga gttgcttttc caggatagaa aatttggatt agacctctgt    111240
```

```
ctgtgcctat gaaaacaagc agagctaact taactccttc tcatcagttc taaccaactg   111300
acatgggcat taaaaaaaag attttatcta ctaagcaaat atgatcacag tctgaagctt   111360
tgttcttgga aaatcccctc tcagggtgtt cagcctttct tcttcagctt gcagaattct   111420
ccatgtttca gtttcctgat aaatcagtgg gcgccgctac tccacatctt tgaagctggt   111480
tgttaagaag cagtgcttct gcagcaatca cagtttaaag catgaatcaa tttaacatca   111540
cacaagctat acatttcaac agagttacag tttcagagta aagtgcaata tacagtataa   111600
agcgaatctg gaattcaagc ccaacaatgt cataaaagag gctgtgaagt ctcacatgat   111660
gtgggccaca gagagggttg ttgccattgg atcttagctc aaatactacc acatcttcgg   111720
agtggcctgc catgggccac ccttactaag gcaatccctc tgtccaagcc aaaatgatat   111780
ctcggacttt ttttgaattg cagagagatt gttgcagcca gggattgcct tagtaagggt   111840
ggcccatggc gggcctctct gaggatgtgg taatatttga gataagatct gaatggcaag   111900
acttcagcca tgtgaagggt ggagggattt ctagggaaag gggtcagcac aggcaaagac   111960
cctatgatgg gaagaagctg ggcacagctt gggattgaat gaatgccaat gtggctgaag   112020
ggtggtgatt gaagaggagg gggagacgag aaggtctgga aggcctgggg catgatcaga   112080
tcaggtgctg aggccgtgga agtagatggg attttcatct aagggaaatg ggaagtcatt   112140
agagagtttt caggagggga tgatatgtat tttttaaaa ttgagcatta tcctcggtaa    112200
acttttgtag tcgttaaacc agagattata agcaggtttt acctcatatg ccagttgcag   112260
ctgattagta gtggctatag agaatcctgg gctgagaagg atactgtggc taaccagaat   112320
tcagtagatg agtttgacgt ggcctgttag tatgactaca ctgtgtgcac tgtttctgca   112380
ttaaatgtct gataaaaaca gagccaaagg aaaaatagaa cttaaaaatt taattctgac   112440
agtacagttg acccttgaaa aacataaagg ttggggtgct gacccttgt gcagtcacaa    112500 atttgcatat aacttttgac ctccccaaaa aactgaacca ctgatagccc actgttgact   112560
ggaagcttta ctgataacat aaacacttga ttaacacatg ttttatatgt tatctgtatt   112620
atatactcca ttcttaccat aaagcaagct agagaaaaga gtattttatt taaaaaatca   112680
taatgaagag aaatatattt aatcttcgtt aagtagaagt ggatcattat aaaggtcttc   112740
accctcatca tcttcacatt gagtgggctg aggaggggga ggtagaggaa aggttggtct   112800
tgctgtctca agagtggcag aggtggaaga aaatttatgt atatgtggac tcatgcactt   112860
caatcccatg ttgtccatag gtcaactgta gtttcaaaac cagcttttta ttactgaaaa   112920
tacgggaaaa aaaactcaga gaagaaatgg aaagtttgct atgatccagt catacagaga   112980
aatccatgtt cagcctgttg atgcacttta agaaggaga tacgtgggta aaacctgatg    113040
ttgaattact cttacatgat tttggacttt tgcaggagct tgtggtgctt tgccacctcc   113100 accacccag tttgatatct ttgctggcag ctgggattcg tccccggatg ttggtgatgg    113160
agttagcctc caagggttcc ttggatcgcc tgcttcagca ggacaaagcc agcctcacta   113220
gaaccctaca gcacaggatt gcactccacg tagctgatgg tttgaggtaa gtaggtcatg   113280
ttgttttcta ttcagtgcat gacaagtgtg atccagactt gctctcaggt tctgagaaca   113340
cttcccagta acactgtgcc ccagtaacaa tttataaaca atttggatga aaactaccat   113400
ttccctgatc aaattttgta atttcagaaa ataagagtat ggaaaccatg cagaacctca   113460
tagcaagtag taatagactt tgaacccaca agttctgctc tagaacccat catcttaacc   113520
ctgtactgat ctgcccttcta taaaaatgta taagttaggc ttcacagtat caaagtaagt   113580
gtcaattaca tgattccaat gaggaaagat gagtccatac ttctcaaggg gactagagtg   113640
```

```
attcatgttg gattcttcgg catgaccatc tcacatgtct cagaggcaca cctaaccctg   113700
catccagagc aagctttgga gagggagcac actggagtgg aaaggctgtg gtctttgaag   113760
acaaaaggcc tgggattcat cactattcca cacatttagt aactgtgatt ttatatctct   113820
gattcccatt ttttaaatag tctgtgaacc atgactaata tttaatgcat aaaattatga   113880
tgacttctgt aataattgga gacattccag atgaaactct tgatgtcccc tctgccattg   113940
ctccccaacc ccagtcaccc tgttacacct gagagtcacc ttacattcct ttcttcctct   114000
ctcatttcac agctaatcct tcagcaaatc ttttcagctc tgccaccaaa atatatctta   114060
atgcttctaa caatttctct cactaacgtc taaatctgag ccagtatcat ctctcattgc   114120
ctactggtcc cctgcttcta cctctgtctc atgatagtcc cattcctcac ccagcctctg   114180
gagtgatttt tctaacatga aagttggatc aggacttgtt cctgttatta cccctcccct   114240
gccttatttc ttgggtacag tgctcagcca ctcccatccc tgaggttcct tgcagatacc   114300
agaggcttta tatctgctgt tgatttcact caggaatgtc tgactcccag atgtgctctc   114360
tacttattat aaaggattat ctgaatcttt ctgaatcctt tcatttagga ctctcagcag   114420
agaggatgtc cgcaacgacc cctttgtctct ccagccccta taggactatt gctgcctagg   114480
attctttatg ttttcatttt ttaaaaactt atttattgtc tgtcttgcca tcagaatcta   114540
agtaccatga agaagggac ttttcgtctt gtttgccatt gtatctctag ctcctaaaat   114600
agtaagcctt cagaattact gtgttgacag taggggaagg gggagaaagg aggaaagaag   114660
gaaaacagtg cctggggcat agaagccaag cagtgtatgc aactttcctt ctcttctttc   114720
tcttctgaaa tgctatgaat atgccttta ggtagtatcc agaaatgttc cttcctgaaa   114780
gggtccagaa actactgaaa actgtacaga ttatgaaatg aaacagggtg cagggatttg   114840
gatttgagtt gatgtttctg cttttgaaca ccaggggaa tcttgggtta cattaatcta   114900
ggtaaagtgc agaatagtct cctgtatttc agtgccctct ttccttcatt taactaactc   114960
taggttctag ttttttcccta attcttccac aaatccccaa agtgtttatt tataaagtga   115020
agaattgcta ttttttaaca ctgttcgaaa caccttatct ctaaaatgac ttattctagt   115080
tctctgaaac cttactttaa ataacaaatc cagcagtttc tgatgaagta aatgaaatgt   115140
cagcatattt taaataatt tgcctaattt gttcttagca taatgccaga aaagctttct   115200
ggattttgta tcacaaaagg ctagtagatt tcagtagcta tcaatcttct accagcacta   115260
agtatatttt aaaaactcag cattaaggtt tattttcca agtatgtttc agcacaggaa   115320
ataaaatcat gctcctttgg agtcccttaa atgctggagc tgtttagagt gacatacaag   115380
aactttcttc acgttacatg ctctctcttc ctccatcttg cttttaactg ttagcttact   115440
tctccaattc aatccacttc gtttgaactc tttatcataa ttctataaaa cttatgaaaa   115500
tacagtcaac tgcattttct gtatgtttct gtgtttcaat atcttcaaaa tggaatgtac   115560
tgccttggta catcacccac tatgaatctg ttatttctgt tatatccac agttgccagg   115620 ccaggatact tgtcccatcc aggccaaaca ccttcccccg aaagcaagta tgcatttgtc   115680
caccaggtcc ttgactctat tttacattat cttttagtc aattcattta tttttatgcc   115740
actcctgctg tcttggttca gtatgtccag ggaattatca gaatttcttt tctaaaataa   115800
aaatctgttt atgcttgcaa ttccttgaca gttctcaatt atctgcaaag tgcatccaaa   115860
cttcttggca tagcatcaaa gatctttctg tatgcctctt gcttcccttt gcggcccctg   115920 ccacccccact gcccacactg cattctagcc gtgatgacag gcttgaattt tcagttatgc   115980
```

```
tcatgtctgt ccatcattgt atttgttatt cctctctttc caccaagttg tctgcctaga  116040
gagctcattt tccttaagaa tttcttcaca aaccatctct actatgaagc tcaagtgtgt  116100
catgaagtgt tagcttctcc aacttgtgtt tcttgcagac actctgtgca agacattgac  116160
ttaggtgcta aagagggaaa gctagatatt atattgttct tgaggttgaa agcttacagt  116220
ctagtaggag agtcaacttt gctgtcttta cctcagtgtt tttctccctc tgtgcttccc  116280
tagcacgtgg tacttacata tttctggaat cttgattaaa cacctgtttg aggactgtct  116340
gagcacaatc cttctggatt gtgacaccct caagggagca gagatacaaa gatggctttg  116400
tatactaaat gactggccct catagatacc tagtacatat ttgtcaaata aatgaatgca  116460
ttctattttt ggaataattc tattcagaat cagataaagt ttactttaag ctatgaagaa  116520
agaagtctct tagcaactct tacaataatc acaatcaaag aatgactgtt taacttaata  116580
taaaccagtt tgttttaata aaatatttga caatagtcat ggttacacaa tgcataaatt  116640
atggctaaat tattatcagg aaggaaaaat ctttacttat tatttcaaaa gctattttgc  116700
tagtctatta aaagctatta gaactgcact tcttaagatt aaattctata attgaacatt  116760
ttaactaacc aagatattat ctctttgcca ctgacattat ttcaaattaa gcttaactat  116820 ttcttttag cctttggaaa gtattctgaa agagtctgtg ttctataaat atacttaaag  116880
aggcatgtct tataaaggat ttggatacta ttcaatgatg tatgacttgg ctttagcttt  116940
tttattctta atctctcagc ttttctcttc agcaggggaa gagtacctaa tggcctttca  117000
gtaatccctt ggtaaatttt tctttcaagc ccattactta ctgtgaaggt caacttcatt  117060
agtgtattta tcttattttt ttcagcccaa aataggtata ttgaaatgaa tgggcctaat  117120
gtcaaatgtc ccgactacat cctggaagag agagaatctt cagctgtatt agttgatgca  117180
gttaaataat atgtactctc caggccctca tacaattgaa agttcagggt atcgttgctg  117240
ctctgcttct aatccttcca gaagtgattg gtgctaggtg atggagtaac tattaattga  117300
tataatgtga gccaaaacca acagtcacga ataagcaaag gatttaaatt taactccatt  117360
aagtcttgtg agaaattatt ttcaacatag gttataacat acctgtgaca tcacatgaaa  117420
tgctgtagtc aatttgacat catggggcag agaagacaga gttggaaatc agaattttat  117480
agacatctaa tgtgataata acattagtag ctgagatgcg gtaagctctt tgaccatgtt  117540
tccagaatgg ataagacctg gttgagatga aaactttaca ctgttttttt atattaacta  117600
tcttttactc tttgcctgaa atgtccaact ctagttgctc gtgattgcgt gggtcagtct  117660
ccagaaggtt ggactttaat attacccgtc atcttttcca agacaaaatt gtattcattc  117720
taactcttag ccccaaattt tcttttttaa ccttaatatc taacatgatt aggtttatgg  117780
taaattatat actcaaacag aagaagagac taatagcaag caaaagtctt atattttcat  117840 ttgtttttcat ccaaaaagta gaaatatttt tccaaacatt gggaaacatt ttagtcagaa  117900
aaataaatat caatgataaa tagaatagag aaaaatttta aagctgagct aaacctctat  117960
gtggttttag gaaaatcaaa actattaaat aaatggcaag tacaacaaaa tcccatcaat  118020
tcttatttaa catacttaca ttttgaaata gttaaaatat tcatatgatc attgagagaa  118080
ttcagaattg cctttaagta attgttcaca tatacaaaag aaaagtctcc aaaaattggg  118140
tctttgcctg agatagattt gtcttaaaat tgaaatcatt cacttatcag atttgaccct  118200
tttttaaagc ataactttgc tgtgtaatat tagacttata tgttttgatt tccttctaca  118260
atatctctta actttaaggg acaaagtgag cacagaattt ttgatgcttg acatagtgga  118320
catttatatt taaggaaatt aggacaaaaa ttattataat gtaatcacat ttgaataaga  118380
```

```
tttcctgtgc attttctggc agatacctcc actcagccat gattatatac cgagacctga  118440
aaccccacaa tgtgctgctt ttcacactgt atcccaatgc tgccatcatt gcaaagattg  118500
ctgactacgg cattgctcag tactgctgta gaatggggat aaaaacatca gagggcacac  118560
caggtaggtg atcaggtctg tctcataatt ctatcttcag gatggataac cactgacctc  118620
agatgtgagt tcagaagagt caaaaggaaa acagagtcta tcacattgtg aacagaggtt  118680
tattttgtga aaaaatgcaa gcatcacatt gtgatttta tcattgtatt ttgtaggaaa  118740
aaaacaattg atgtaatttt tcagggcaaa aactgaataa aagaagaga atgtttgata  118800 tcaagttata tgtttaaag ttagatttgt agattcttta gatactctag aggtcataaa  118860
aagtaacagc aaaaacttta gtctaggtat tgttggcact tgtgaggcaa atcaaattca  118920
ggtccacaaa ttcttttca taattctgaa acccaaagaa ctctgaaaat cccaagattt  118980 tttaaaaat gactaatttg gtgtcaaaac ctaagcaagc tgacttgttg cttattacaa  119040
tctttatttc tcatgctcag tgtgaatatg catacatttt gctgcagaaa tatatacatg  119100
tttgagtaca gggggctggc cgtgacccta ctgagggttt ctgtacacat cactgtctac  119160
cctgtggaat cttacctccc tttcttagtt cccaatcctg aaaagcagtt atggggccag  119220
tgctctgtac agacatgttg tctcagacat cagtttgagc aggaagtaaa tcatttaggg  119280
gttggcattt gtttggagtg tggggaacac tctatcttta gggaaacttt atatagttag  119340
ttatttgtaa gtaaaattac aggtggctat acatcatctt gctgattgca actcaattaa  119400
atcaccgtgc ctggcacaga agaaaatatg ctacaggata tctcactagg gaaaaggttc  119460
tagttcgttt cctgcgcact caacttttgt acttagataa gcaaatggcc ccagattcca  119520
atgcctggtt ttatttttgc tccaaataca tatatactct tttgttttgg atagttacat  119580
tttagaagta gactgtgtat tctcataaac acttcaaagt gtatgttctg gctgagagtg  119640
tctctgtgtt gttcaataat aataagacta attatcattt tttgagtacc tgctgtgcgt  119700
caggcccagt gccacgtata ttagagacaa gatctcttat cctcatgcca gggctggaag  119760
ttagctatta gtttctcatt tgccaaatga gaaaactgag gctcagggag attatgtaac  119820
ttgcagaata tcactcagta attggccaag ataagaattc agtctaaatg agaaccagat  119880
ccagagatat ttggctttaa attctatagt ctctcctaaa ccatatgcaa ctctaacatg  119940
aagaagctta tttaatcttc actattaaaa aagtcaaaac aaaacaacag agccatgaat  120000
agcaaatatt gtcaatgaga ggtttggaaa aacagtctta aaggatgaaa ttccatagac  120060
ctgatatatt tccacctgga aaagtgggc atgggacagt gatttctct tgaaagatct  120120 gctcatttt gtcatgggac atgaaggtgg actggaccac tcagtttctt ctttctgcat  120180
ctcccaaccc agtctttctg ttcatggggt gaaaatctgt tgttgaagcc ttgtctgctt  120240
aattggacag tggatctctc gggtccctgt gggctgtgcg cttgtacttg agctctgctt  120300
cttcactctg tggtctaggc cagctagcag ccagctgagt tcaccttggt tcagactcat  120360
ggcctttcat tttcagtatc tgacttcctg gttttgctga aaacctgtct aaaatgtaat  120420
atccatctga ttcttcatac caagccacac aattcttcct gatccctttt aatctccaat  120480
attgaatggt ggtaacataa atatggagac agatcatgtc agaaacccag ggcctaatct  120540
tttcttttct gcctactctt ctcacaggct gcttagtact ttgtaagctt ttttttttt  120600 tctggctgta acctagattt tctctttatc attactctat ttattattgt tagagcactt  120660
ctgattatct cagccctaaa ctctgcctcc aattttaaat aacaataact cccactcctg  120720
```

```
ctaatactgc tactactact accatcacca aactttttct tccccaaagc agttctgttt    120780
gggaaggaaa cagttccctc tcatacaatt tcagttatct tcttgtcttt tccgtttaat    120840
gaatcttcct gttaatgtta catcttttaa catggaaact tctagagaaa caaaagacga    120900
tggatttgtt aaaccttttg ggtgtatttt tatactaact cttactgcag cgtgtgcatt    120960
atgagtgtag gtccattacg gctgtattag gagcagaacc ttccagagca tgagcgatgt    121020
gctgggcttg tgcttagctc tatccatgag ttaagtatct caatccttag gaccctctga    121080
catatgtgct attattattt ctagtctata gatacagaga ctaaagttta gagaatataa    121140
aaaaacattt acaaggtcct atgggacaaa aactgtagga caaaatgcaa acccaagcag    121200
cctgagagca gagctcctgg tccagcactg tgatagctgg ggacgcagag acagaaacaa    121260
tgcaattatt gacagggacc atggtgctgt gtctgtccac attttgaaga taattatggt    121320
ttggatattt tcacctttaa ataacttgga gagtttcaac attaactcag tcagatggat    121380
acatttatat catatcctgc tgggagtgac agttaattct gggtcctatg gcaattgcac    121440
ttttgactga gatgaatgct gactgatggc tttaacattt aactaatgcg atagtattta    121500
acacacccat ataaatacta tagtcttcgg gtaaataaaa tgttaccggc tggacataca    121560
tgaatatctg atggagatta tggaacatac tctactcata cttctctgaa agtaaaaaat    121620
aaaagatatg tttcagtaca caatgtgata tgtactcaga cttaattcat aaatttctct    121680
tatccttcat ccgtggatct tttcttatt tacttattgc gtttgttaaa atgcaggctt    121740
ctctgaaaaa ttattttaa aaatagtttt tagacaatga atcatatttt ctcaagtatt    121800
ttaacattgt aatcattatg ataattatcc aaggggaaat tatacttatt ttttattcat    121860
ttattcattc atttggcaac aatacattga acatttacta agcatcaaac tggctctacc    121920
acttaatagt ggcatgatgt tcatcaagaa attgttagtg caatcaagaa cactagaaat    121980
tcattggatg aatttaaaga agcttttaga agggtattat attataattg aggcacttta    122040
tgaatatata aataatatta tgttttcatg ctagagatca tgccaatgaa gatatttact    122100
ttgaaaagga gaagattaga agtttaaaag catttccata ttgaagtaaa tattcatttc    122160
catatcttca cagttatctt tctctgagtt ctctgactca ttgtgaaaaa aaatcccaac    122220
cttcttcaca gctctaccat cttcggattg ttgcctagag gggtaaaaac tattgtaaaa    122280
ggatgtgtgc actggatgag aatttagaat tagacgaaat gaccctaga gtcttttcct     122340 gctttaagag cctgtgattc caaattctaa cagtacattt atcaagaaaa aatatgctga    122400
acatttaaat agttttgaa tagtacctag atataataga tacctaataa atgtgctcaa     122460
tgaataataa ataactggtt aagatttaaa taagcctcca aaatctcttc cacattctaa    122520
gaagggaagc ataaaggttg ttaatgaact agtgactgtg tgggtagctc attatttta    122580 agtactcttg actttgctgt tcattatctg tgtggcctta ggaaaataca cacatttctg    122640
aaaggattat gtcgtttgta aaatagaaag tccttatctg tctaccacag atgattctta    122700
tgcaaatcaa atgaaatgtt caataaggtg tctgtaaaat agtagagaga gatgaattag    122760
gagctattgt gatttgttta cattatgtca caggtgcact ttattaggga tatgttttat    122820
cttaattaca caattctta acttagattt tgagaattat attatggtta taggaaaa       122880 tgccettatt ctaaggaaat gtataatata tttaggtctg aaacattgta tctgtaacaa    122940
tatagtatgt aaattatgct aattcacatg ataattatat gtaattatat taatatatta    123000
ctatgtatac aatatattta catgcatata tgtggggaaa tgttatcagt tagtgtagta    123060
ggggttatca tactcaaatt cgatgtctcc atccttccaa ctcttcatgc ttttccagca    123120
```

```
tggtgaggac tgctgagctc catcttttgc tggtagtctc tctgtcaaat agaactgttt  123180
ccaaattcag tcatttgctc cttgaaggct atgaattcat acttcgttat attttctgg   123240 ctgcatattt aaattacttt aacaatcata taagttcatt gtaaaaattt tggaaataaa  123300
aaggaagata aaatgcacag ataattttag caaatgaaat aataattata tgggatgta   123360 tttcttccta gattttaatt atgtacattc ccatcaactt tttattttga aaatgtttaa  123420
gcctaaagaa cagttgaaag agtagtacag gctgggtgca gtggctcctg cctgtaatcc  123480
caacactttg ggaggccgag gtgggtggat cacttgaggt caggagttca agaccagcct  123540
gaccaacatg gtgaaaccct gtcactacta aaaatacaaa aatcagctgg gcacggtggt  123600
gggcacctgt aatcccagct actcgggagg ctgaggcagg agaatcgctt gaacccagga  123660
ggcagaggtt gcagtaagcc aagatcacac ccctgcactc cagcctgggc aagagagtga  123720
gactccatct caaaaaaaaa aaaaaaaaa aaagaaaga aagagtagta caatatacat    123780
tcatactcat atacccgacg cataaattca ttgattattt acttttttgcc ctacttgttc 123840 tttcttgctc tctttgcgta tgaatgaatc attgaaatta agttgtagac atcatgccat  123900
atcacctctg aacagtgtgt atatttcttt agaataagga tgtttactta cataatcata  123960
ataccattat cacagctaag aaaattaatt cagttgattt tttccacata tttgataact   124020
ttctgtctat ccacgattat gtcttacata ttctttttaat ttatgtcata gcatatcatc 124080
ttagaaagtg atccctaagt tactgcatgg tatacattgt ttaaccatttt cccttttgtga 124140 ttggatgtct ttaggttgat tatattttta ttattatcac aaatgttgaa atcactcttt  124200
ttttctgaag aatttaaaag taattatatct gtcttatgga ataaaatatt tatttcccct 124260
taaaagaatt tcaggcatga acccaagaga gaaggctttt tttttttgttt tagttgttgt 124320 ttttatttt attttttat ttttgggtag aaggagcaga gagacaagtt caggaaataa    124380
tgagagtgtt agaattttgt tcaggttaaa gtgagttgga gtgaagttta gaaatctcct  124440
ttctactcat ctctcctgtt tttaaaacac tgtcctggaa atagttaata ttaggaacga  124500
gaaaaatggt ataggttttc ctagtacact ttatttctta attatgaaat tctacttaat  124560
aacttaccat tgaatgttta tccttattat cattcaaggt aatttttattg aagattgaag 124620 atatttataa taaagattga aggattttat tgtcctgtgt ggtcaacctt gggggtgag   124680 atgttatgag acaggacaat taattgactt gatcaaggta ccttgttata aaataacac   124740 agcctggttt agaacatctc ttcctgactc tcttatttgg catatagcct aagtgtatgc  124800
ctccttggat gtatgagccc tgatgttggt catatttatt attttatctg cttactttca  124860
gggtttcgtg cacctgaagt tgccagagga aatgtcattt ataaccaaca ggctgatgtt  124920
tattcatttg gtttactact ctatgacatt ttgacaactg gaggtagaat agtagagggt   124980
ttgaagtttc caaatgagtt tgatgaatta gaaatacaag gaaaattacc tggtaagttc  125040
tgttttctct acaatgaaga ttttttttct taatatcagc agcttcattt ttatttaatt  125100
gtagttgtat gcttaattcc ttaaacagat gatcattttt tttgtttagt gcataaatat  125160
tcttaaatct tgtgatatat taataaaaat caccctgaaaa aggtagcagt tttaggcttt 125220
ttaaaaaatc cgcaattaat attggtgtag ttaatattat atttagaaac atagagaagg  125280
aaattgctgt tagaactcca catttggtga ttttttaattt tcataaagaa ttactgtgta 125340
ctcattatcc tggaatgttt tcgttttctt ggagtgaaat aatttacatg caggaatgga  125400
agactgaatg atctataata ataattttttc ataagaatcg gtaaatgtgt atttaatgtt  125460
```

```
atcaaagctc atttggaatg gttgtctcat gctttcaaga aattagagga ctttgtaatt  125520
cattccttaa ccattacttt agttctcacc acaaaataac attttaagtt tatttagctc  125580
tttctcatat tttctgcttt ccctttcatt taaaaaatac ttttgagtgt acacaatgtg  125640
ccatgtacag gaaatagagc tttatctttt ttgggtataa cttcaagatc atggcaaaag  125700
aaaacttatt attaattgga taaaccttag atataatcta ggttatttcc cttattttac  125760
tagttttcta gtgaaaatat tcaggtctct gctgggtaca gtggcttacg cctgtaatcc  125820
cagcactttg ggaggcccag gcaggcagat cacttgaggc caggagctgg agaccagcct  125880
ggccaacatg gtgaaaccct gtctctacta aaaatacaaa aagtagctgg gcatggtggc  125940
atgtgcgtgt agtcccagct accaaggagg ctgaggcacg agaatagctt gaacctggga  126000
ggttgcagtg agccgagatt gcgccactgc actccagcct aagcaacaaa gtgagactcc  126060
atcttaaaaa aaaaaattca gttctgtgtt ctgcatcaac cagaataagc tacgcctctt  126120
ataaaaaaca aatgtgcaca aaccatctgt gaggacataa ggattaaatg cttgcttact  126180
ttgagtatta aaataaaaag tagaagcttt attatatgag taaaagtgtt tccaaagtct  126240
atttgaaatg caggtacaga atgaaaatct gttattttat taaatcgtta tttgggtctc  126300
ttttttattcc ataaaaaaaa aatcttttcc acatctctta gtggagatca agttaacaaa  126360
attagcttta attttgtgac aagtaaattt acataaatat aggattatgg agataatatt  126420
tttctttgca atgtctggac cttttataaa cattgagagg aaatataacc attcttactt  126480
atttagtatg ctagcatgat gttttttaat gttttagatc cagttaaaga atatggttgt  126540
gccccatggc ctatggttga gaaattaatt aaacagtgtt tgaaagaaaa tcctcaagaa  126600
aggcctactt ctgcccaggt attcttaaag ttttgttaat attttgtaca gaacatcatt  126660
tgcatatatg catatatata taatcttcaa atatatatac ttaaacacat aaacacacag  126720
agacagaatt aaaaatagtt ataaggcaaa cctcctataa ttttcaccat cccaggcaca  126780
aaaaaaggac attgccaaaa cctcacatgc tcccatatgc ctgtctcctc ttctcttctt  126840
tgaaatgcct gcccattatt ttgcccattt ttctgttgac tcttttgcct acaaatcaaa  126900
tcagaaaaaa atttttatat ataacatact aatcctttct tggttttata tgttgcaatt  126960
tcttttttcga gctggtggct tgcttttttaa atttcttgta gggtgcccgt taatgaatgg  127020
aatttcttaa ttttaatata tataaattta acaattcttc ttttttcttc ttttcctggt  127080
tattcctatt tggtcctgtt gtagagccca tctttctttt agagctacaa aaatatttac  127140
ctgcaatttc ttcaaacatt ttaaaagttt gcttttgaca agattttaat ccattggaat  127200
tgacattttt atctgtatcc cattccttt tttaatgtgg aagactaatt ttttcaggtt  127260
gatttactaa atggcttctc ccctttttgtc ccatagatct gatgtgtcca ttttgtaatt  127320
tattaaagat aatgtgcata tccacgtgta cactgtcttc cactgatcaa ctcatttatt  127380
ttcctccag tattaccctg tcttaattcc tgtagcttta taatgatctc ctctccctat  127440
ttatttttct catccaggaa tattttaacc agtcttaggc ttagcttttc tatataaaat  127500
ttagaatcat gctgtcaaat cttatgaaaa accacattgt cgtttggatt ggtcttggat  127560
tgaatatgtt gacaatctgg agatgatatc cttatgatat taagtctttg tattctttt  127620
cttatttatt tatttattta gaggcagggt ctcactctgt cacccaggct ggagtgctgg  127680
agtgcagtgg caggatcaca gctcaatgca gctttgacct cctgggctca agtgatcctg  127740
tcgcctcagt ctccatcagc caattgtgtg ccaccagacc tggttaactt ttcctttaat  127800
ttttttgtag agaaagggtc tcactctgtt gcccaggctg gtcttgaact cctggcctca  127860
```

```
agcaatcctc ccgcctaggc ctcccaaagt gcatgagcaa ctgcacctgg ccaagtcttc    127920
ctattctgga atggcatgaa ttctctctgt ttacttaggt cttctcaagc gtctttcaat    127980
aaagttttgt aatgctacat acaggtcttg catatctttt gctggatttt cttgctgcaa    128040
attgctttaa atgcagttca tggcttgaga tttgttttt  aactgcccag ttaacgtaaa    128100
tctggtctat gaattgtatt dacaacaagc ttgtgagtag caattttca  gcaaccttt     128160 gctccctctc cccgctccct gcacagtccc agaacaactt ccttatata  ccaatgaagg    128220 tggaaatgtg gacaggttga tttctccttc ttgtttatgc tgaatatgca gtcctttggg    128280
gtcccagctt tataggtaca gtcccttac  taagactgtc tatcttggga aggccctaga    128340
ctccaacttc tctcccatgg gccccacaaa gcatccaaga gtatacattt atattatctc    128400
actttgtctt ggcagacaaa tgtcttcagg gcaagtctgg ctttaggggt ccactgacct    128460
ctctggtttc tgtctctcac tgtgatttcg gcctgataat tccttatggt gtcagatctt    128520
caatgttttt aatacattgt ttttaaaaaa atcatttagc attttaaatt gttttagtt    128580 ggaagatttg cccaagtaac cttgtccacc atattatctg aaagagaact cttgtcatgt    128640
tttacactga tacacatttt aataaatgtg ggttatcttt atgttgtgag ctcttgattt    128700
ggtattataa ttaattggaa aagttttaac tttaagtatt ctgatcaaaa tagtcaagta    128760
caactataat gactttatca aatattacat aattttcctt ctacttggtt tacttgtttt    128820
ttaatttagg ttaccatcaa tgttagtcac atgaactttt atatttatgt ccacagtaaa    128880 aattttttcat agcttgttgt ttttctttct tgttttttca ttttcaatta tacttcacct    128940
atacttaaca gaatacttaa caaatatgta tatatatgac aatattaaaa agcttagaca    129000
tacttatttt atgtttaaaa tataacatat actaggcaag acaggaaaac tcatcacttt    129060
tatgaaatga ggcacagaca gagtaatggg ctttcttggt gtctcctgag tggcgggcag    129120
gtggccatgt cacagctcta atcccagttt cctgacttct ggttctgttt tcttacggtg    129180
ccttcacact gtctctccag atcaaaaaca gaatctagag atgacttcta aattttgtta    129240
ccaaagactg aaattcctgt tcctttcaac tactagaagc tcaactaaat tgttggccca    129300 aggttttc  tctcactggc ggtggctctg caatatagaa ttgcatgcag agtacctcct    129360
gactccgcta aaatcctgtt taattgaccc ttgagatttt cttttcaagt taaaaaaaat    129420
actacacata ccaaagagta tcaagcacag tttaaaaata catatttgtc ttttcatgta    129480
attttatttg tagtttagat tactaatctt ggtgatctag ttgggttcca gtttaacagt    129540
tttaggtttt gcttgacaga gctataacac ttcagtctat atttgatttt tcaagggaaa    129600
tgagttaact cgataagtac tgttttgtta tctttaaact ttctcaggtc tttgacattt    129660
tgaattcagc tgaattagtc tgtctgacga gacgcatttt attacctaaa aacgtaattg    129720
ttgaatgcat ggttgctaca catcacaaca gcaggaatgc aagcatttgg ctgggctgtg    129780
ggcacaccga cagaggacag ctctcatttc ttgacttaaa tactgaagga tacacttctg    129840
aggtaaatcc aaatgctctt taaatctttc ataatttaaa gcatatacca tttggaaagt    129900
tacttaggaa taaattaaat aagagccaat gtaggattat tattcaatta gccttctgtt    129960
agaacaagag tattcaagag caaatgtgtt ttgctttaga atcacagcat atgtcttagc    130020
tcagggtccc tagaaacaga gcctgagatg ggttatcttg cacaagtgat ttaaggaaag    130080
agaatcttag agaagtag  aggaagccag aaagggcaga ggaaaagct  cagcagaaat    130140 gtggtttctg aagaggtcca gcctcagtct ctgcccacaa ggagctctgg aatatgaata    130200
```

```
ggagcacaga attttcccac tgccaggcaa gggagccagt ctttcattct cacatattgt    130260
tcagtcattg gctgcaatct gctgggaggt ggggtagtg taactttcaa ggcatttctg    130320
ggcaagctgc ctcctgtcat ctgagggtat tctgtgataa atagcacatc tctgaactat    130380
agtagccaac actcagggta gctggggatg gcgtacctga tggataaagg agatctggac    130440
atggctccta aaagtggatc aatacattgt gttggcaaat ataagataag tttctagact    130500
tcaaagacaa cctagtattt tgactgctgc ctgaagataa atattgtgcc tcaacattag    130560
ttctgaggtt aaacaatctt ttttttttaa ttgatcattc ttgggtgttt ctcgcagagg    130620
gggatttggc agggtcatag gacaataatg gagggaaggt cagcagataa acaagtgaac    130680
aaaggtctct ggttttccta ggcagaggac cctgcggcct tccgtagtgt tgtgtccct    130740 gggtacttga gattagggag tagtgatgac tcttaacgag catgctgcct tcaagcatct    130800
gtttaacaaa gcacatcttg caccgccctt aatccattta accctgagtg gacacagcac    130860
atgtttcaga gagcaccggg ttgggggcaa ggtcatagat caacagcatc ccaaggcaga    130920
agaatttttc ttagtacaga acaaaatgga gtctcctatg tctacttctt tctacacaga    130980
cacagcaaca atctgatttc tgtatctttt ccccacattt cccccttttc tactcgacaa    131040
aaccgccaac gtcatcatgg cctgttctca atgagctgct gggtacacct cccagacggg    131100
gtggcagccg ggcagagggg ctcctcactt cccagaaggg gcggccgggc agaggcgccc    131160
cccacctccc agacggggcg gcggccgggc ggggctgcc ccccacctcc cggatggggt    131220
ggctgcccag cggagacgct cctcacttcc cagacggggc ggctgctggg cggaggggct    131280
cctcacttct ccgacggggc ggctgctggg cggaggggct cctcacttct cagacggggc    131340
agctgccagg caaggggct cctcacttct cagacggggc ggctgccggg cagagggact    131400
cctcacttct cagacagggc ggccaggcag agatgctcct cacctcccag acagggttgc    131460
ggccgggcat aggctctcct cacatcccag acggggcggc agggcagagg cgctccccac    131520
atctcagaca atgggcggcc gggcagagcc gctcatcact tcctagacgg gatgcggcc    131580 gggaagaggc gctcctcatt tcccagactg gcagccggg cagaggggc tcctcacatc    131640 ccagacgatg ggcggccagg cagagacgct cctcacttcc cagacgggt ggcggccggg    131700 cagaggctgc aatctcggca ctttgggagg ccaaggcagg cggctgggag gtggaggttg    131760
taggtagcca agatcacgcc actgcactcc agcctgggca actttgagca ctgagtgaac    131820
gagactccgt ctgcaatccc ggcacctcgg gaggccgagg ctggcagatc actcgcggtt    131880
aggagctgga gaccagcccg gccaacacag cgaaacccg tctccaccaa aaaaatatga    131940
aaaccagtca ggcgtggcgg cgcacgcctg caatggcagg cactctgcag gctgaggcag    132000
gagaatcagg cagggaggtt gcagtgagcc gagatggcag cagtacagcc cagcttcggc    132060
tcggcatcag agggagacgg tggaaagaga gggagaggga gaccatgggg agaggagac    132120 ggagagggag agggagagga acaatcttct tatatggttt gaaggaatga gaattcacac    132180
tgaaaaataa tttttaattt tagtttcaga tgtcatcttg ataggcaaaa cttgtctgcc    132240
aattaactca tttattgctg aaaattaaat aaaattggca ttgttttaa agtaatgca    132300 agaaagcaaa aagagttatg ttgataacag aatcctttat tctgtacaag ttctagttgc    132360
ttaagcttaa atcaaatcct gctaagtata ttttctttc ttaacaggaa gttgctgata    132420
gtagaatatt gtgcttagcc ttggtgcatc ttcctgttga aaggaaagc tggattgtgt    132480 ctgggacaca gtctggtact ctcctggtca tcaataccga agatgggaaa aagagacata    132540
ccctagaaaa gatgactgat tctgtcactt gtttgtattg caattccttt tccaagcaaa    132600
```

```
ggtatggtag tgaatttgat caatggggaa attacagatc ttttaaacga ctgaattgtg   132660
tgcataattg ttattgcatc agcaaagatt gttcattttt agcctatttt cattggtttg   132720
catatattaa agggaattgt ggaaggtcac agagatattt gttgttttc tgaatacaga    132780 tctagctgag acatttataa aataagtcaa ccatttattc aggcctacca gccctgctcc   132840
tggtattacc tcaactgtgg ctctatctct ttacttctcc tcagatcaat gaatctttgt   132900
agggcctctt caaggataaa ttctcattca ttcattcttt gaaaaaaaaa aaatatatat   132960
atatatatat atgaaaccca ttgtgtgcca ggcttaaaca taccagttat ctaactacca   133020
aattaagaaa aaaattaaat aaatgaatta ataaattctt aataggtgaa aatgacttag   133080
ctcttatcaa ttgcagggtt cttgtcccaa agaaatatat ctacatagca aaatttcagg   133140
tgtgagttgt aggttggtga ctgtaatatt tggggcagga tgatttccag gaggcattaa   133200
gattataccc tatatatttc tctggtttaa gttagtattg gaaaaaaagt actagaaaaa   133260
tgtgaagcct gttttttgta cctgaaatat caactccact ggcagtttcg gagttgaaat   133320
tatttgaata tggtcaaaga aaaatttcaa tggatggaat tgggcaagga cgactttatt   133380
caagcctatc acagcagggg agagagatca gactgaacta aactccactg aaacaaaagg   133440
tgggagagtt ttaagcgcag gggtgagcta atggaaacgt actggagcac cttgttggaa   133500
ggaagtggga gcagttgtca atgtgattag gccatctgtg tttgctaatt gtcccttatt   133560
gaaggtaggc tcctactctc ccacagacac tggggaattc cttccttcct tccatccctc   133620
cctccctccc tccctccctt ccttccttcc ttcttctttt ttttttttt gaaggagttt    133680 tgctcttgtt gcccaagctg gagtgcaatg gcatgatctt ggctcactgc aacttccacc   133740
tcctaagttc aagcgattct ctagcctcag cctcctgagt agctgggatt acaggcgtgc   133800
accaccaaac ctggctaatt ttttacattt ttagtagaaa cgggatttca ccatgttagc   133860
cagactgatc tcaatctcct gacctcaggt gatctgccca ccgcagcctc ccaaagtgct   133920
gggattacaa gtgtgagcca ccacgccagg cctctgtctt gataattaca tttcaaagga   133980
atggctccca ggtccttgga aaagacattc ttggggtata aaactgggaa gagtctggga   134040 aaagggcag agaaagaatt tataattcca agtcttctaa agtaaatact ctaagaaaag    134100
ggaggttagg aatttatagt tgagaagtct atctaaagtt taataaagtg gaggagaaca   134160
ttaaggccat tttagtcaac atacatgttc tttttgtaac aatttcaaca tttttccttt   134220
tagcaaacaa aaaaatttc ttttggttgg aaccgctgat ggcaagttag caattttga    134280 agataagact gttaaggtaa atgttgaatg cattctacat ctaaatttat tttaagtctt   134340 ttgtttata tatatctcac acccctctta tgggattata aactccctga gagcaagaat    134400
cataaattat gctgtatttg tattgcttca taaaatcttg aacacagtag atcctctgaa   134460
aatacttgct gattgactgt atattttata tgaatgaact aagaataaaa tgataaatga   134520
catctgattg ataatattgg gaatggaaat aattcaattt gtacataact gaggcagata   134580
attccttata aatatattgt ggaaaaaaaa caaaaatata cttaagtttt aaatatggct   134640
tgccattaac ttttcttaa gcattgaaga atcatttaa ttttcttttc ttcagattcc     134700
tatttagtca ttaaagcatt catttctcta tccatctatt catctttggt tccatctatt   134760
cactcaactt cctacccgtt cattctccta ttgccaaaaa gcttattatc tgatgagaga   134820
cagggaagta gagtataacc cttaggttat ttcttttgta atttttacat gggaaaaaga   134880
atagattgaa tgtaacaata atatttcgaa tatgacctaa attttttttat gtataatatt   134940
```

```
tgtacatatt tatggggtac atgtgatatg ttgttacatg catagaatgt gtaatgatca    135000
agtcagggta tttaggatat ccatcaccat gagcatttat ttctctgtgc tgagaacatt    135060
tcaagtctcc tagttatttt gaaatgtttt taactgtagt cactttattg tactattgaa    135120
cattagaact tattcctcct atctaactgt atgtttgtac ccgttaacca gcctcccttc    135180
atcctcccct tctcccacac acccatatcc tcccaagcct ctggtaacta tcattctact    135240
ctctacctcc atgagatcaa cttttttagc tcccacatat gagtgagtac atgtgatatt    135300
tgtctttctg tgcttggctt atttcactta acataatgac ctccagttcc atccatgttg    135360
ctgtatatga catgatttca ttcctttta tggtcaaata gtattccgtt atgtaaatac     135420
acacattttc tttatgcatt cattcattca tgggtgctta ggttgattcc acttttttt     135480 ttagctattg tgaatagtgc tgcgataaac atggggatat aggaatccct ttgatatact    135540
gattcccttt cctttagatt agtatcagta gtaacattgt tggattgtat ggtagttcta    135600
tttttaattt ttttgagaaa tcaccatttt gttttccgta gtggctatag caatttacat    135660
acacaccaat agcatatggg cattcgtttt tttccgcatc cttgccagca tgttatttt     135720 tgtctttttt ataatagcca ttctaattgg gtgaagaaga tttcattgtg gttttcattt    135780 gcattttac tgatgattag ttaatgttga gcatttttt tcatatatcc attggccatt      135840
actatgtctt cttttgcaaa tgtctattta gatcctttgc caacttttg ttttgtttta     135900 agacagggtc ttgctttctt acccaggctg gctcacagtg gcatgatcat agcttgttgc    135960
agccttgacc ttctgcactc aagtgatcct ccaacatcag cttcacgagt agctgggact    136020
acaggcgtgt gctaccatac ctggctgttt attttttgta gagatgcggc tccactatgt    136080
tgtccagact gatctcaaac tcctgggctc aagcaatcct cctgcctcat cttctcaaag    136140
tgctgggatt acaggcatga gccaccatac ccagcccttt gcctactttt aaatggagtt    136200
cttttttttt tttcctgttg aattgctttt tcgagtttct tgtgtattct ggatgaatag    136260
tttgcaaata tttcctcaca tttaatggat cctctctata ttgttgatag tttcctttgc    136320
tgtgcagaag cttttagtt tattatagtc ccatttgtct aattttgttt ttgttgcctg     136380
tgcttttggg atcttaacca taaactcttt gtctagacca atgttctgaa atgtttcccc    136440
tgtttccttt taatagtttc atagcttctg gtcttacatt taagtcttta atccatcttg    136500
agttgaattt tgtaaatggt gagagagtgg ggcctacttt catccttctg catactgata    136560
tccagctttt ccagcacaat ttattgaagg tggtattctt tctcccatgt atgctttgg     136620 tgcctttgtt gaaaattagt tggctttaaa tatgtgggtt tatttctggg tcctctacat    136680
tggtctacct acctgtgttt ttgccaatac tgtgctgttt tggttactct agccttgtaa    136740
tatattttca agtcaggtag tgtgatgcct ccagctttgt tctttttgct caggattgtt    136800
ttggctattt tggctctttt tcggttccac tcaagtttta gaatttttt tttctatttc     136860 tgtgagaaat atcattggag ctttcatggg aatttcattg aatctgtaga ttgctttggg    136920
tagtatggtc atttaacaa tattaattct tccagtctgt gagcatgaat atctttccat      136980
ttgtttgtgt cctcttcaat ttctttcatg ttttcaggt ttccttatag agatcgttca     137040
tcatctttgt taaatttact cctaggtatt ttattaattt tttgtagcta cttcaaatgg    137100
gattgctttc ttgattttc agctactttg ttgttgttgt tgtatagata tgctactgat     137160
ttctgtatgt tgattttgaa tccttttacta tactcattta tcagaactaa gagttttttt   137220
taatggaatc tttaggtttt tgagttttaa ttttaatatc tctaatcatt taagatggaa    137280
agtagttttt tgaaagcaca gatttttatgg agttttgttc tgtggatact caatttgctg   137340
```

```
agtgtgtttt cttttttttt tggcaaagct taaaggagct gctcctttga agatactaaa   137400
tataggaaat gtcagtactc cattgatgtg tttgagtgaa tccacaaatt caacggaaag   137460
aaatgtaatg tggggaggat gtggcacaaa gattttctcc ttttctaatg atttcaccat   137520
tcagaaactc attgagacaa gaacaagcca actgtaagtt attttttatc tgtacaagta   137580
atttatcatt atactttgt tttttcctta taatcattaa taatactgtt gataattcat   137640
aaggaagatc ttttaaaatg cataatttat tttctatcat aaaattaaac tttcattata   137700
aaaaattttg aaaattccag aaagcagaag ggtatttta agaagtcact caacctaatc   137760
acttttaggg ataaaatatg taaactcatt gtaatcttag tagtatttat caatctaaat   137820
tttttaacaa ttttttattat ctgtgtttca aattagacat gaaattggaa gacaatcaac   137880
tttgtatttc accaaattca cggactatac atatgcaatt tgggtaactt ccattaagta   137940
ttgattgtag gaaagataga cagcaagtat tcttgcttgt ccaaagttgt ttctagattt   138000
gataattata cagatgtcta ctcacagcca agttagtgat accagtttca aacaagaata   138060
aaataaaata ttaatataaa cctctttcaa gtttgctttt tttcagtggt attttaatca   138120
aatctttgca gttggttctt atttatcaca ttcctcagtg ataagcagta taggattgtg   138180
gataagagca taaatcatag ttcagatatt gctttgccat ctattggttt tgtgaacttg   138240
ggcaataacc tttcacatct tcagtcatct cttacctgag gattgtaata ttctctatct   138300
caaagagata tttggaggag taaataagaa tgttaatata tggatcttaa ttaacataat   138360
gaccagcacc tggtaagctg tcaataaaca ttagctatta ttattattat tagctttgag   138420
tcacaaatcc ctaccttagg gaatatcctg gtttcccatt atccatcaaa tttcccaaga   138480
ttggcacttg ggagtaatct ttgactcctt tgttttttgc tccctttatc cacttgaccc   138540
tcctaattgt catttgaatc tttgtacttc tcactgttct cagtgctggt accatgggcc   138600
agactgccat ccattatctg tggccacatt aacaagagca tccagttctc accctctgat   138660
tatactctct tcaacatatt ttcagcattg cagacagagg gacctttcta aaatgtacat   138720
caatctgatg caattttcct gcttaaaacc cttcagtggt atcccattgt cctttatatg   138780
aagtccaaat tccttaagac agcctactgg gcccttcata attcagtgct tgcttacctg   138840
tctagattca tattttgcaa gcttttttgcc atctgtgctt tacccaaact gaaattgact   138900
cagatctcta agacaacctg ttattacctt tcacccccaa cctttgaatg tggtcttctc   138960
cttacctgga tgactattat gcccctgcc tatttcagtc caagcaccac ttgctctgag   139020
tggcaggtta ggtgactttg tgcttccatt gcatctaatg ttttccttca cagtagctat   139080
aattgtattt gttaaagtag tttctcaata ccactaaatc tactggcttt caacattggc   139140
tgtgcattta gaaaccacta ggtagctgaa aataatatga tacctgggcc ctacctcaga   139200
ccaattaaat cagaccagtt aagcctggga tggggatcag attttttttt tcaggttctc   139260
aagtgattct aaagtatatt tgaggttaag atatactgcg gagtgcagtg tattataagt   139320
tcccatgaat gaggattttt atttctgtct ttacatattt atttactagt atgtggttaa   139380
catttggatc aactcattct cattctgtaa tacccacatt ttaaaaaatg aatgtaaaaa   139440
tgtcttttat tattttattt tttcaaattt aattttgat tccaggaata catgtgcagg   139500
tttgttacaa agtatagtg cgtgatgctg aggtttggaa tacaactgaa ctcacaaccc   139560
agaaagtggg catagtgctt gataggtagt ttttcatctt tgctccccctt cctgtaattt   139620 ccacttttaa cccaattata caagcctgaa aacctttaaa aagaagggc ctccagttta   139680
```

```
tttttttatt tcatagcaca ttttatggga ttatggatat cagttaactc tttaaagttc   139740
catataagat ttggagcata gatgctttac tagagagcat ccataaagat caagctctca   139800
aagatgctca tctcccaaaa gagattggga cctagatgca taaacactta aatataaata   139860
tttgctctct tctgaacaag tatctcctgt ggccttggtc tctacccac aaaacagaca    139920 tcacatcact aatcaggggt tgcctcatca tcagtaccct catcatcatc agtacacacc   139980
gactgagagg catgttgggt aatgaaagat gactgccttt gaagccggaa gactccatag   140040
gacttttgga gttctaggtc tgcaacatgt ttttagtcct aggtcggcaa gcatgatgtt   140100
agtcatagga ccttgagcaa attatttagc atttgtacat gtttctttct actattaaaa   140160
acattgagat ttatcatatt ttatgttttt ttattaagga tcaagcaaga taacacacaa   140220
aagtatttta taaatacgg aaattccatg caaaactttg tcctaattgg aactattttc     140280
tattaaatac agcaaatatc caagaaggaa ttacctaaag cgtagtggct ctctgacaac   140340
acatcatatt tttacctcct tttccagaat agaaagaaaa gggggaggaa aaaaaatctt   140400
cctactctag gatatactaa tgattgttaa atctttatgg tattttcatg ttatctatct   140460
gatttaaatg caattttgac tatttttaca tattcctcgt tgttcattca tactgtagtg   140520
ccttcttcta ttccccccact taacagactg cttgattata tcagaggtgc ttatctgtgc   140580
aactgtttac tggacgaggg gtatgtagaa aatacattgt cctcatcctt atgaaattac   140640
actcataatc tagtgtgagg gatgcactaa taaagacaat tttatattta ataaggtcta   140700
taatatgaca gtgacaccag tggggaaaag ggactggttg gtctattttg ataggtcagg   140760
gaagaaatcc agaggagccg acatttaagt tcatcctcaa aggccaagta ggagtttgcc   140820
atgctgatgt ggcccaaggt agccaatctg tttgtgaaat atgtacaatg ccagatgtct   140880
taggttgaaa gggaaatatt ttaaggtgtt cgtaattttt ctttatgttt aaagggaa     140940 aatggcaaat attttacttt ctgtttatgt ttggatgatg tggattttg ttttctataa    141000 tttgactggc ttaactgcaa agatatccct tgctttaaaa tttgaagaca ctgcaactaa   141060
attttatttc agcattttat attttataac tctaggtata aaaggctaac acttaatttt   141120
ctgagcattc atgaaacaaa gttttgcaag aacattcaaa agttacagat ataatatttc   141180
cttcagaaat ttagatatag tacaaaattc tacaaagagc cacatagaat tgaaactaaa   141240
agtaagacca aagtaaacat tggacataat ctttatttta ttatcacaag aaattaatat    141300
aaagtaacca aaagtaagta aagtaccaaa gcatgttata tattcaattc agaatggtta   141360
gggaagaata tgaaataatt gcaatagtct agcttgttta gttttcaaaa tagtgttttt   141420
acattaagaa ctaatataag gttgtattac acgtagaaat tttaagaaga aaacaaatag   141480
tgatgacttt ctattttttt ttctctgtag gttttcttat gcagctttca gtgattccaa   141540
catcataaca gtggtggtag acactgctct ctatattgct aagcaaaata gccctgttgt    141600
ggaagtgtgg gataagaaaa ctgaaaaact ctgtggacta atagactgcg tgcactttt    141660 aaggtaaatt ctgtggtttt taattttatt cccaaaagaa ttatctttgc acttcatgtg   141720
tcacagagga aggattttc ttcctttctg cctctgaata gagaattttt ttaaaatgca    141780
gaaaaaaatt tgtaatgctt ctcagcacca tcttttcaga tcaagaaaat tttgtcttca   141840
gaacataaaa gaataggcac ataatgtgca tagttttctc atggtattac aaagaatgtt   141900
ctcgaatgaa aatactacat tattgaaaat gagcatattg gagtctctgc tagctttgac   141960
atagttctgt cacagtgtca aatatactat ttataattaa attatgggcc ccaggattat   142020
ctgctctaaa gaaaaagagt cacaaaataa tagacaaata tgggggaaa tgcaatggac    142080
```

```
tgaccgaggc gctaaggagt ggggatcaag accccagaat gagagcatag tgcttagtct   142140
gatgcagcct gtgagtgaca aatccatagc aagcacattc tttctgtgct ggtgctgaga   142200
aacaggacca ttttcaagct tatttgctag ccactttata tttttatttt gttttgattt   142260
taccatatag atctatgata ctcttgagaa cattttagat tacacactat atctgtaaaa   142320
ggatacttca aagtttcctg tcttagattc atctgacagt ttttctatgg attgtgagaa   142380
gggctcacag tttatgttca gaagggccaa caggtctcct tgataaaggg ttccttactt   142440
cctgaagtac caaaacgatt aggattcttt tatttctgga cacttcattt ttgtcatgaa   142500
ttagactatt cactggttct gggaaaaaat tcagtggttt gtatcgatat cttttacatg   142560
tgaatgacta taatttatg ttcctttgta acattgagac ttcatgtaaa acttttgact   142620
ctaacttttt ttttcttta tcctgggcac atgtatgcta ttttttactga attagatagc   142680 tttggtattt ataaaaattg tatccctctt attcataatt tcctgaaaat gaagggctat   142740
tgttatcttt gataatttat gcttcaagta aagaagtgtg gctctttggc atctgtattt   142800
agcaaaattt gctttgtata attttaatga tgcataatgg tggtggtgtc atgttttaat   142860
aatttaaaat gttgtttatg ttatcatatg taaatagcat ttatctctta attggtggta   142920
aaattattaa tgtatacttt atggttctag ggaggtaatg gtaaagaaa caaggaatc    142980 aaaacacaaa atgtcttatt ctgggagagt gaaaaccctc tgccttcaga agaacactgc   143040
tctttggata ggaactggag gaggccatat tttactcctg gatcttcaa ctcgtcgact    143100 tatacgtgta atttacaact tttgtaattc ggtcagagtc atgatgacag cacagctagg   143160
caagtttctt tcctttagat attttcata ttctctaagt cttataaaat atgcctttat    143220
tttacgttta cattttctct gaactttcca gtgtcatatg gatggtcttg gagggtcaca   143280
cagtgaaaca taagactggt ataaattgtg aatagggtca ttacagaagt ggagggagta   143340
aatgctctca gtcccacaag agaagcagat tactgcagct gaacactcag tttgggtctt   143400
acttgctttt ttcctttta cctaaggcaa aaatgggaaa tacatggtat tgaatatatt    143460 ttacttttg agcaaagaaa ataaagaaaa tgtttgtttt aatcatagtc tagcctccca   143520
gcttgttaaa gaatctcatt tggtttttca ttctataaca aatctttttt cttgcagcaa   143580
tacatgctga actgcacaac ctacaaatat tgacaaatca tatttactc aaactttgtc    143640 ttttttttgct tctatttta tatttaaata tgataaaatt gtgatagcac ataaaatata   143700
ttttctgcat aaatatattt gcgtcttcct ttgataataa tttgttttag aaaataacaa   143760
taatagcata tatacaaaag tttacaaaaa cgacactatg gggtttaatt ctgaaaaaaa   143820
ctagaattta tgtaaccttta gcaaataatg aatgttttga acatggtgaa gaaaatatat   143880
tcattgcaag tatatgtgaa agaggaacat gtgttttct agcaccttca cctattttc     143940 atttatagac tttagagttg cacaggagtt acaattagat gctcttaatg actgtaaact   144000
attaagatac atgtccacac aagcagagca gtaggtctct caataggttg tctcagtagt   144060
cttattctac caaagttgtt gcattctcta gttgaattgt atgtactttg ggacccaaat   144120
agcttgctta taactgaagt tatagtggaa tgtctatggg ttatagtttg atttaaaat    144180 aaagatcaat tggaggatag cctacaaggt gctgcatgag ctggcttcac tgtacctctc   144240
ctgcctccat catctaccac attcctacca gatcttgctt gtctagatga acatccagtt   144300
cttctcaatt actatgctat attttgcctc agggatttgc acatgctgtt tatttctttg   144360
cttagttaac atagcttttt ttcatgctta tttaactcat atgctttgaa atgttagctc   144420
```

```
ctgtgtcaaa acctctgaga agccaacact gattaggtca aagttcccgc tttgggttcc   144480
cataacagct ttcttgcata gttttgatca tggtcatatt tttttttcat taatgctagt   144540
ctcttcacta gaatataaac tccaagacgg ttgggttagt gtgttttgt ttacccctt    144600 tttcccagga tctagcctag ggcctacata gaagactttt gatgcaaatt tgttgaataa   144660
attagtgaat gatttgaaaa gaaaatatga tattttgaca tagtatcagt atatccatcc   144720
atctaagtgt ccatctaaat actcatattt gtactaaata ctcatatttg taccttacca   144780
tatccaaaga acttttcaca cacattacct cgtttaacat tgtaactttg ggaagggtaa   144840
tgtataaata ctgagcctat tttatagaaa ggttaagctg ttttctcaga ctcacataat   144900
taagaattgc agcaaggagt ggatcacaga ttttgttatt ttttaaaaaa atgctggtct   144960
ttattcaata taattgaagg gtcacctaga aaatagaatt gtgaattcag ttccaaggta   145020
tttgtgtctt aaactatgaa caacttact ttttttcag gccagtttaa tatatagttt     145080
taacagaaaa cttacatatt tgttttttgt aaaggaagcc ttaaaaatgt catgctggta   145140
ttgggctaca accggaaaaa tactgaaggt acacaaaagc agaaaggtaa catttagaag   145200
gatactgttt tccaaacagg gcaatgatgt gaatgatggt aacatattat gtgtttcata   145260
aatttgtaga aaatattaca tatggtataa tcaggaattt taattggtag tttatagtgt   145320 aaagaacta gacataaatt ttcaaaatta caagtgatat gaagtgttaa atatttatat    145380
tttcagctga agtagaggtg tcaatcacta gctcaacctt aaacgaaatg tgaatatttt   145440
ttacaactta tctatatcta cataatgtct aattttgaac agtgtttgaa aaagctttta   145500
tttcttttag aatatgaaat gttaatttat taaatgttga tactctattt gaaatttaat   145560
agtttctata atgtattata aaacttttcc aagtatagtt tttataaat aataatttag    145620 tacattagtt atagctgtgt ttatatttac atttatctaa gtcaactaaa aatacatgag   145680
ccaaactgaa ataaaataag aatgttttat gatggatctt tgaaacatga tttcattttt   145740 ttcttttct agagatacaa tcttgcttga ccgtttggga catcaatctt ccacatgaag    145800
tgcaaaattt agaaaaacac attgaagtga gaaaagaatt agctgaaaaa atgagacgaa   145860
catctgttga gtaagagaga aataggaatt gtctttggat aggaaaatta ttctctcctc   145920
ttgtaaatat ttattttaaa aatgttcaca tggaaagggt actcacattt tttgaaatag   145980
ctcgtgtgta tgaaggaatg ttattatttt taatttaaat atatgtaaaa atacttacca   146040
gtaaatgtgt attttaaaga actatttaaa acacaatgtt atatttctta taaataccag   146100
ttactttcgt tcattaatta atgaaaataa atctgtgaag tacctaatt aagtactcat    146160 actaaaattt ataaggccga taattttttg ttttcttgtc tgtaatggag gtaaacttta   146220
ttttaaattc tgtgcttaag acaggactat tgcttgtcga tttttctaga aatctgcacg   146280
gtataatgaa aatattaaga cagtttccca tgtaatgtat tccttcttag attgcatcga   146340
aatgcactat catatatgct tgtaaatatt caaatgaatt tgcactaata aagtcctttg   146400
ttggtatgtg aattctcttt gttgctgttg caaacagtgc atcttacaca acttcactca   146460
attcaaaaga aaactccatt aaaagtacta atgaaaaaac atgacatact gtcaaagtcc   146520
tcatatctag gaaagacaca gaaactctct ttgtcacaga aactctctgt gtctttccta   146580
gacataatag agttgttttt caactctatg tttgaatgtg gatacctga atttgtata     146640 attagtgtaa atacagtgtt cagtccttca agtgatattt ttattttttt attcatacca   146700
ctagctactt gttttctaat ctgcttcatt ctaatgctta tattcatctt ttccctaaat   146760
ttgtgatgct gcagatccta catcattcag atagaaacct tttttttttt cagaattata   146820
```

```
gaattccaca gctcctacca agaccatgag gataaatatc taacactttt cagttgctga  146880
aggagaaagg agctttagtt atgatggata aaaatatctg ccaccctagg cttccaaatt  146940
atacttaaat tgtttacata gcttaccaca ataggagtat cagggccaaa tacctatgta  147000
ataatttgag gtcatttctg ctttaggaaa agtactttcg gtaaattctt tggccctgac  147060
cagtattcat tatttcagat aattccctgt gataggacaa ctagtacatt taatattctc  147120
agaacttatg gcattttact atgtgaaaac tttaaattta tttatattaa gggtaatcaa  147180
attcttaaag atgaaagatt ttctgtattt taaaggaagc tatgctttaa cttgttatgt  147240
aattaacaaa aaaatcatat ataatagagc tctttgttcc agtgttatct ctttcattgt  147300
tactttgtat ttgcaatttt ttttaccaaa gacaaattaa aaaaatgaat accatattta  147360
aatggaataa taaggttttt ttaaaaactt taaatgcttt taagcatgtt tatgaatttt  147420
taaactttgt gatagtgttt tgcttttcac atataggtct gttatccatc tcataggaaa  147480
ctttgtatta atttgtatat gggacattcc acaataagaa agtgcaacta aagttttttc  147540
cttgataact tatggaatat ttaaatttaa ttttctataa tacatatagt tgccaggatc  147600
ccaggacaaa atctgatggg catgatacat tctattttca agttctctta aaaagttttt  147660
gtaagtaaac ttgtttgctc ttgagtactg aaacaaaata taagacttta gagcaaatga  147720
catatacaaa aaaaaggcac agtcacttca actgttttct gattagaagc ctaaataaac  147780
ttgctaatta tgatcaaaat acaagcatat tatcgtaaca aaatattctt ttgggaaaat  147840
tttgaattaa gaaaagggag cctctttgac tctaattctg gtaggtactc tatcgattat  147900
gtgtgaacta tttcaactaa aacgcaactt atttttcatc aaggcagtga aatatattga  147960
tgaaacatag cagaattacc aaaaaaagat tgtcaatttt cctaagttaa atgtaaggat  148020
gcaaatgttc taatattgag gggagataaa attcaaaacc attgggactt tgcttcttta  148080
tccatcactt tgggtagctg aacacctaac ctggtaaatt gaatgttttt catgcaggct  148140
tatcagcaat tcagtaaaat agtaaactat gtcaactcgg gagaaactga catcctcatt  148200
ctccatgcta gccagtttct catccagggt gtcattgttt ctaataacaa ttcagaatct  148260
ggctgcttaa aggcacctac gtacgtggtt cttttctaatt tgtcaaggca tttggagtga  148320
tcctatcacc ctgatttcaa gcaaaagaca gggaggcacc tgacccaaag gcctgctgtc  148380
tgaacacact ctgaatgggt gagcagagat gtgctttaag atagaaccta aggtggttct  148440
ctctatgtgc tgccctcaca ctgctcttga tttctaccct tacctgggaa gtctctactt  148500
gatgtctgtc ttaggctaag aaaaagagaa gagaaaggga atgagtatta gcatctggat  148560 tctgggctg cttcttggcc tctgtgagaa tccactgttt cacagcaatc acagcctaga  148620
aaactagact ttatggagta aacaataggt atcattctga cctgggcttc accacaatca  148680
cccactgaac actcccaaga gaaggttgtt accatttatt tatgaaaata ccaaactatg  148740
tgatacatac tctattagaa gtattatgga aaaatagaga atatgtctac ctggccagag  148800
aatagaggat ctggatcaca aaaaaagtac aaatatttaa gcagagactt aggacaaatg  148860
ggcattcaac aatttaggac acatgggcat tctacaattt ccagagtgaa gtaaacattc  148920
taggcagata aatcacacat gtgctgtctt aggaatgtga gcttattttg aaagcatccc  148980
tatcaaatac gtgctaaaac ttgtgacaag ttcccattcc tagagtactt acaggataca  149040
cttaagtgac tgaagatgca agagaaatat atatttgtgt atggatatag cattttatca  149100
ttaattgaga gattataaag ctaatgagct tttctttgca gagggagtat tgttaggat  149160
```

| | |
|---|---:|
| gaaatgggga gagatgtttc aaacaccaag tttatcttat aggttaagaa atcctagaag | 149220 |
| gaatccatga ctttatgtat atatacaata tatgacaaga gatttcccca tctcattaca | 149280 |
| aaatgagcac aaagtaacta actcaaagct tttgctatta tgataaaagt ttaaaaggct | 149340 |
| agtacatagc agaaatgtga tttactataa cgggggtcca ggggataaaa tatttgcaag | 149400 |
| ctgattgtct catgttggca atgttttcat ttcctactac gttaggtaac acagatgaga | 149460 |
| ttgtacatca gagtaagaag gcaaccacta atagaagctg catgcgggca aaagactatt | 149520 |
| ctctgaccat aagcttagtt tagatggatc cttgctgcaa tcactaaatt cataaatctg | 149580 |
| tgctagtatt ggatcaggaa atctctgcac aagcagataa ataaaaactt tctgctttgg | 149640 |
| ctgaaataac tgcttttagg aaaagaaaga gtatatgctt attaatatag cttgggatgt | 149700 |
| ggacctcttt gacgagacta tacaattcaa ggtagacaaa gtatgcctaa aaataaatct | 149760 |
| aaaataaact tgtatattca atggaacat attctttaat aatgtcattt ttaagggctc | 149820 |
| tgcatttatt ccataaatgc tgccattatt gttcagtttt tcttaattac ctgcattcac | 149880 |
| tttagaaaac agaaaaaaaa aaaaaaaaa aaaaaacaga aacagttgca aaagaaagca | 149940 |
| gccagaaaga acatacattt agaattgaaa aagaccttgg tctaaattct agatttggca | 150000 |
| t | 150001 |

<210> SEQ ID NO 3
<211> LENGTH: 9239
<212> TYPE: DNA
<213> ORGANISM: Homo sapines

<400> SEQUENCE: 3

| | |
|---|---:|
| gcgctggctg cgggcggtga gctgagctcg ccccgggga gctgtggccg gcgcccctgc | 60 |
| cggttccctg agcagcggac gttcatgctg gagggcggc gggttggaag caggtgccac | 120 |
| catggctagt ggcagctgtc aggggtgcga agaggacgag gaaactctga gaagttgat | 180 |
| agtcaggctg aacaatgtcc aggaaggaaa acagatagaa acgctggtcc aaatcctgga | 240 |
| ggatctgctg gtgttcacgt actccgagca cgcctccaag ttatttcaag gcaaaaatat | 300 |
| ccatgtgcct ctgttgatcg tcttggactc ctatatgaga gtcgcgagtg tgcagcaggt | 360 |
| gggttggtca cttctgtgca aattaataga agtctgtcca ggtacaatgc aaagcttaat | 420 |
| gggaccccag gatgttggaa atgattggga agtccttggt gttcaccaat tgattcttaa | 480 |
| aatgctaaca gttcataatg ccagtgtaaa cttgtcagtg attggactga agaccttaga | 540 |
| tctcctccta acttcaggta aaatcacctt gctgatattg gatgaagaaa gtgatatttt | 600 |
| catgttaatt tttgatgcca tgcactcatt tccagccaat gatgaagtcc agaaacttgg | 660 |
| atgcaaagct ttacatgtgc tgtttgagag agtctcagag gagcaactga ctgaatttgt | 720 |
| tgagaacaaa gattatatga tattgttaag tgcgttaaca aattttaaag atgaagagga | 780 |
| aattgtgctt catgtgctgc attgtttaca ttccctagcg attccttgca ataatgtgga | 840 |
| agtcctcatg agtggcaatg tcaggtgtta taatattgtg gtggaagcta tgaaagcatt | 900 |
| ccctatgagt gaaagaattc aagaagtgag ttgctgtttg ctccataggc ttacattagg | 960 |
| taatttttc aatatcctgg tattaaacga agtccatgag tttgtggtga agctgtgca | 1020 |
| gcagtaccca gagaatgcag cattgcagat ctcagcgctc agctgtttgg ccctcctcac | 1080 |
| tgagactatt ttcttaaatc aagatttaga ggaaagaat gagaatcaag agaatgatga | 1140 |
| tgaggggaa aagataaat tgttttggct ggaagcctgt tacaaagcat taacgtggca | 1200 |
| tagaaagaac aagcacgtgc aggaggccgc atgctgggca ctaaataatc tccttatgta | 1260 |

```
ccaaaacagt ttacatgaga agattggaga tgaagatggc catttcccag ctcataggga    1320
agtgatgctc tccatgctga tgcattcttc atcaaaggaa gttttccagg catctgcgaa    1380
tgcattgtca actctcttag aacaaaatgt taatttcaga aaaatactgt tatcaaaagg    1440
aatacacctg aatgttttgg agttaatgca gaagcatata cattctcctg aagtggctga    1500
aagtggctgt aaaatgctaa atcatctttt tgaaggaagc aacacttccc tggatataat    1560
ggcagcagtg gtccccaaaa tactaacagt tatgaaacgt catgagacat cattaccagt    1620
gcagctggag gcgcttcgag ctattttaca ttttatagtg cctggcatgc cagaagaatc    1680
cagggaggat acagaatttc atcataagct aaatatggtt aaaaaacagt gtttcaagaa    1740
tgatattcac aaactggtcc tagcagcttt gaacaggttc attggaaatc tgggattca    1800
gaaatgtgga ttaaaagtaa tttcttctat tgtacatttt cctgatgcat tagagatgtt    1860
atccctggaa ggtgctatgg attcagtgct tcacacactg cagatgtatc cagatgacca    1920
agaaattcag tgtctgggtt taagtcttat aggatacttg attacaaaga agaatgtgtt    1980
cataggaact ggacatctgc tggcaaaaat tctggtttcc agcttatacc gatttaagga    2040
tgttgctgaa atacagacta aaggatttca gacaatctta gcaatcctca aattgtcagc    2100
atcttttcct aagctgctgg tgcatcattc atttgactta gtaatattcc atcaaatgtc    2160
ttccaatatc atggaacaaa aggatcaaca gtttctaaac ctctgttgca agtgttttgc    2220
aaaagtagct atggatgatt acttaaaaaa tgtgatgcta gagagagcgt gtgatcagaa    2280
taacagcatc atggttgaat gcttgcttct attgggagca gatgccaatc aagcaaagga    2340
gggatcttct ttaatttgtc aggtatgtga gaaagagagc agtcccaaat tggtggaact    2400
cttactgaat agtggatctc gtgaacaaga tgtacgaaaa gcgttgacga taagcattgg    2460
gaaaggtgac agccagatca tcagcttgct cttaaggagg ctggccctgg atgtggccaa    2520
caatagcatt tgccttggag gattttgtat aggaaaagtt gaaccttctt ggcttggtcc    2580
tttatttcca gataagactt ctaatttaag gaaacaaaca aatatagcat ctacactagc    2640
aagaatggtg atcagatatc agatgaaaag tgctgtggaa gaaggaacag cctcaggcag    2700
cgatggaaat ttttctgaag atgtgctgtc taaatttgat gaatggacct ttattcctga    2760
ctcttctatg gacagtgtgt ttgctcaaag tgatgacctg gatagtgaag gaagtgaagg    2820
ctcatttctt gtgaaaaaga aatctaattc aattagtgta ggagaatttt accgagatgc    2880
cgtattacag cgttgctcac caaatttgca aagacattcc aattccttgg ggcccatttt    2940
tgatcatgaa gatttactga agcgaaaaag aaaaatatta tcttcagatg attcactcag    3000
gtcatcaaaa cttcaatccc atatgaggca ttcagacagc atttcttctc tggcttctga    3060
gagagaatat attacatcac tagccctttc agcaaatgaa ctaagagata ttgatgccct    3120
aagccagaaa tgctgtataa gtgttcattt ggagcatctt gaaaagctgg agcttcacca    3180
gaatgcactc acgagctttc cacaacagct atgtgaaact ctgaagagtt tgacacattt    3240
ggacttgcac agtaataaat ttacatcatt tccttcttat ttgttgaaaa tgagttgtat    3300
tgctaatctt gatgtctctc gaaatgacat tggaccctca gtggttttag atcctacagt    3360
gaaatgtcca actctgaaac agtttaacct gtcatataac cagctgtctt ttgtacctga    3420
gaacctcact gatgtggtag agaaactgga gcagctcatt ttagaaggaa ataaaatatc    3480
agggatatgc tcccccttga gactgaagga actgaagatt ttaaacctta gtaagaacca    3540
catttcatcc ctatcagaga actttcttga ggcttgtcct aaagtggaga gtttcagtgc    3600
```

```
cagaatgaat tttcttgctg ctatgccttt cttgcctcct tctatgacaa tcctaaaatt    3660
atctcagaac aaattttcct gtattccaga agcaatttta aatcttccac acttgcggtc    3720
tttagatatg agcagcaatg atattcagta cctaccaggt cccgcacact ggaaatcttt    3780
gaacttaagg gaactcttat ttagccataa tcagatcagc atcttggact tgagtgaaaa    3840
agcatattta tggtctagag tagagaaact gcatctttct cacaataaac tgaaagagat    3900
tcctcctgag attggctgtc ttgaaaatct gacatctctg gatgtcagtt acaacttgga    3960
actaagatcc tttcccaatg aaatggggaa attaagcaaa atatgggatc ttcctttgga    4020
tgaactgcat cttaactttg attttaaaca taggatgt aaagccaaag acatcataag     4080
gtttcttcaa cagcgattaa aaaaggctgt gccttataac cgaatgaaac ttatgattgt    4140
gggaaatact gggagtggta aaccaccctt attgcagcaa ttaatgaaaa ccaagaaatc    4200
agatcttgga atgcaaagtg ccacagttgg catagatgtg aaagactggc ctatccaaat    4260
aagagacaaa agaaagagag atctcgtcct aaatgtgtgg gattttgcag gtcgtgagga    4320
attctatagt actcatcccc attttatgac gcagcgagca ttgtaccttg ctgtctatga    4380
cctcagcaag ggacaggctg aagttgatgc catgaagcct tggctcttca atataaaggc    4440
tcgcgcttct tcttcccctg tgattctcgt tggcacacat ttggatgttt ctgatgagaa    4500
gcaacgcaaa gcctgcatga gtaaaatcac caaggaactc ctgaataagc gagggttccc    4560
tgccatacga gattaccact tgtgaatgc caccgaggaa tctgatgctt tggcaaaact    4620
tcggaaaacc atcataaacg agagccttaa tttcaagatc cgagatcagc ttgttgttgg    4680
acagctgatt ccagactgct atgtagaact tgaaaaaatc attttatcgg agcgtaaaaa    4740
tgtgccaatt gaatttcccg taattgaccg gaaacgatta ttacaactag tgagagaaaa    4800
tcagctgcag ttagatgaaa atgagcttcc tcacgcagtt cactttctaa atgaatcagg    4860
agtccttctt cattttcaag acccagcact gcagttaagt gacttgtact ttgtggaacc    4920
caagtggctt tgtaaaatca tggcacagat tttgacagtg aaagtggaag ttgtccaaa     4980 acaccctaag ggcattattt cgcgtagaga tgtggaaaaa tttctttcaa aaaaaaggaa    5040
atttccaaag aactacatgt cacagtattt taagctccta gaaaaattcc agattgcttt    5100
gccaatagga gaagaatatt tgctggttcc aagcagtttg tctgaccaca ggcctgtgat    5160
agagcttccc cattgtgaga actctgaaat tatcatccga ctatatgaaa tgccttattt    5220
tccaatggga ttttggtcaa gattaatcaa tcgattactt gagatttcac cttacatgct    5280
ttcagggaga gaacgagcac ttcgcccaaa cagaatgtat tggcgacaag gcatttactt    5340
aaattggtct cctgaagctt attgtctggt aggatctgaa gtcttagaca atcatccaga    5400
gagtttctta aaaattacag ttccttcttg tagaaaaggc tgtattcttt tgggccaagt    5460
tgtggaccac attgattctc tcatggaaga atggtttcct gggttgctgg agattgatat    5520
ttgtggtgaa ggagaaactc tgttgaagaa atgggcatta tatagtttta atgatggtga    5580
agaacatcaa aaaatcttac ttgatgactt gatgaagaaa gcagaggaag gagatctctt    5640
agtaaatcca gatcaaccaa ggctcaccat tccaatatct cagattgccc ctgacttgat    5700
tttggctgac ctgcctagaa atattatgtt gaataatgat gagttggaat ttgaacaagc    5760
tccagagttt ctcctaggtg atggcagttt tggatcagtt taccgagcag cctatgaagg    5820
agaagaagtg gctgtgaaga ttttaataa acatacatca ctcaggctgt taagacaaga    5880
gcttgtggtg ctttgccacc tccaccaccc cagtttgata tctttgctgg cagctgggat    5940
tcgtccccgg atgttggtga tggagttagc ctccaagggt tccttggatc gcctgcttca    6000
```

```
gcaggacaaa gccagcctca ctagaaccct acagcacagg attgcactcc acgtagctga    6060
tggtttgaga tacctccact cagccatgat tatataccga gacctgaaac cccacaatgt    6120
gctgcttttc acactgtatc ccaatgctgc catcattgca aagattgctg actacggcat    6180
tgctcagtac tgctgtagaa tggggataaa aacatcagag ggcacaccag ggtttcgtgc    6240
acctgaagtt gccagaggaa atgtcattta taaccaacag gctgatgttt attcatttgg    6300
tttactactc tatgacattt tgacaactgg aggtagaata gtagagggtt tgaagtttcc    6360
aaatgagttt gatgaattag aaatacaagg aaaattacct gatccagtta aagaatatgg    6420
ttgtgcccca tggcctatgg ttgagaaatt aattaaacag tgtttgaaag aaaatcctca    6480
agaaaggcct acttctgccc aggtctttga cattttgaat tcagctgaat tagtctgtct    6540
gacgagacgc attttattac ctaaaaacgt aattgttgaa tgcatggttg ctacacatca    6600
caacagcagg aatgcaagca tttggctggg ctgtgggcac accgacagag gacagctctc    6660
atttcttgac ttaaatactg aaggatacac ttctgaggaa gttgctgata gtagaatatt    6720
gtgcttagcc ttggtgcatc ttcctgttga aaaggaaagc tggattgtgt ctgggacaca    6780
gtctggtact ctcctggtca tcaataccga agatgggaaa aagagacata ccctagaaaa    6840
gatgactgat tctgtcactt gtttgtattg caattccttt tccaagcaaa gcaaacaaaa    6900
aaattttctt ttggttggaa ccgctgatgg caagttagca attttgaag ataagactgt    6960 taagcttaaa ggagctgctc cttttgaagat actaaatata ggaaatgtca gtactccatt    7020
gatgtgtttg agtgaatcca caaattcaac ggaaagaaat gtaatgtggg gaggatgtgg    7080
cacaaagatt ttctcctttt ctaatgattt caccattcag aaactcattg agacaagaac    7140
aagccaactg ttttcttatg cagctttcag tgattccaac atcataacag tggtggtaga    7200
cactgctctc tatattgcta agcaaaatag ccctgttgtg gaagtgtggg ataagaaaac    7260
tgaaaaactc tgtggactaa tagactgcgt gcacttttta agggaggtaa tggtaaaaga    7320
aaacaaggaa tcaaaacaca aaatgtctta ttctgggaga gtgaaaaccc tctgccttca    7380
gaagaacact gctctcttgga taggaactgg aggaggccat attttactcc tggatctttc    7440
aactcgtcga cttatacgtg taatttacaa ctttttgtaat tcggtcagag tcatgatgac    7500
agcacagcta ggaagcctta aaaatgtcat gctggtattg ggctacaacc ggaaaaatac    7560
tgaaggtaca caaaagcaga aagagataca atcttgcttg accgtttggg acatcaatct    7620
tccacatgaa gtgcaaaatt tagaaaaaca cattgaagtg agaaaagaat tagctgaaaa    7680
aatgagacga acatctgttg agtaagagag aaataggaat tgtctttgga taggaaaatt    7740
attctctcct cttgtaaata tttattttaa aaatgttcac atggaaaggg tactcacatt    7800
ttttgaaata gctcgtgtgt atgaaggaat gttattattt ttaatttaaa tatatgtaaa    7860
aatacttacc agtaaatgtg tattttaaag aactatttaa aacacaatgt tatatttctt    7920
ataaatacca gttactttcg ttcattaatt aatgaaaata aatctgtgaa gtacctaatt    7980
taagtactca tactaaaatt tataaggccg ataattttt gttttcttgt ctgtaatgga    8040
ggtaaacttt attttaaatt ctgtgcttaa gacaggacta ttgcttgtcg atttttctag    8100
aaatctgcac ggtataatga aaatattaag acagtttccc atgtaatgta ttccttctta    8160
gattgcatcg aaatgcacta tcatatatgc ttgtaaatat tcaaatgaat ttgcactaat    8220
aaagtccttt gttggtatgt gaattctctt tgttgctgtt gcaacagtg catcttacac    8280 aacttcactc aattcaaaag aaaactccat taaaagtact aatgaaaaaa catgacatac    8340
```

-continued

| | |
|---|---|
| tgtcaaagtc ctcatatcta ggaaagacac agaaactctc tttgtcacag aaactctctg | 8400 |
| tgtctttcct agacataata gagttgtttt tcaactctat gtttgaatgt ggatacccctg | 8460 |
| aattttgtat aattagtgta aatacagtgt tcagtccttc aagtgatatt tttattttt | 8520 |
| tattcatacc actagctact tgttttctaa tctgcttcat tctaatgctt atattcatct | 8580 |
| tttccctaaa tttgtgatgc tgcagatcct acatcattca gatagaaacc tttttttttt | 8640 |
| tcagaattat agaattccac agctcctacc aagaccatga ggataaatat ctaacacttt | 8700 |
| tcagttgctg aaggagaaag gagctttagt tatgatggat aaaaatatct gccaccctag | 8760 |
| gcttccaaat tatacttaaa ttgtttacat agcttaccac aataggagta tcagggccaa | 8820 |
| atacctatgt aataatttga ggtcatttct gctttaggaa aagtactttc ggtaaattct | 8880 |
| ttggccctga ccagtattca ttatttcaga taattccctg tgataggaca actagtacat | 8940 |
| ttaatattct cagaacttat ggcattttac tatgtgaaaa ctttaaattt atttatatta | 9000 |
| agggtaatca aattcttaaa gatgaaagat tttctgtatt ttaaaggaag ctatgcttta | 9060 |
| acttgttatg taattaacaa aaaaatcata tataatagag ctctttgttc cagtgttatc | 9120 |
| tctttcattg ttactttgta tttgcaattt tttttaccaa agacaaatta aaaaaatgaa | 9180 |
| taccatattt aaatggaata ataaaggttt tttaaaaact ttaaaaaaaa aaaaaaaaa | 9239 |

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

```
<210> SEQ ID NO 11
<211> LENGTH: 19
<212> TYPE: DNA
<213> ORGANISM: Artificial sequence
<220> FEATURE:
<223> OTHER INFORMATION: Primer

<400> SEQUENCE: 11
ggcgagttat ccgcaccat                                                 19

<210> SEQ ID NO 12
<211> LENGTH: 24
<212> TYPE: DNA
<213> ORGANISM: Artificial sequence
<220> FEATURE:
<223> OTHER INFORMATION: Primer

<400> SEQUENCE: 12
ccaaaaccag catgacattc ttaa                                           24

<210> SEQ ID NO 13
<211> LENGTH: 23
<212> TYPE: DNA
<213> ORGANISM: Artificial sequence
<220> FEATURE:
<223> OTHER INFORMATION: Probe

<400> SEQUENCE: 13
tgagagccat ggccacagca caa                                            23

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
agtccaacta ttgacaggtt                                                20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
agtgcactag cagcttggag                                                20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
tccaggtggc tactgaggca                                                20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 17
cagccaagat caagtccgga                                               20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ccacacctct acgacagggc                                               20
```

METHODS FOR REDUCING LRRK2 EXPRESSION

SEQUENCE LISTING

The present application is being filed along with a Sequence Listing in electronic format. The Sequence Listing is provided as a file entitled BIOL0282USASEQ_ST25.txt, created on Jun. 19, 2018, which is 216 KB in size. The information in the electronic format of the sequence listing is incorporated herein by reference in its entirety.

FIELD

Provided are methods for reducing expression of LRRK2 mRNA, and optionally reducing expression of LRRK2 protein, in an animal. Such methods are useful to prevent or ameliorate at least one symptom of a neurodegenerative disease. Such symptoms include loss of motor function, aggregate formation, and neuron death. Such neurodegenerative diseases include Parkinson's Disease, including non-LRRK2 mediated Parkinson's Disease.

BACKGROUND

The leucine-rich repeat kinase 2 (LRRK2) gene encodes a protein called Dardarian. The LRRK2 gene is active in the brain and other tissues throughout the body. One segment of the dardarin protein is enriched with leucine and may be involved in signal transduction and cytoskeleton assembly. Other parts of the dardarin protein are also thought to be involved in protein-protein interactions. Additional studies indicate that dardarin has an enzyme function known as kinase activity, including phosphorylation and GTPase activity.

Genomewide association studies have found an association between LRRK2 and Parkinson's Disease. Indeed, LRRK2 is the greatest known genetic contributor to Parkinson's disease. Nonetheless, Parkinson's disease has not been considered to be a genetic disease. The majority of Parkinson's disease cases are idiopathic. Approximately 10 percent of Parkinson's disease cases have been linked to a genetic cause. Mutations in the LRRK2 gene are the most common cause of Parkinson's disease in this relatively small group, representing one to two percent of total Parkinson's cases.

Currently there is a lack of acceptable options for treating neurodegenerative diseases such as Parkinson's Disease, including non-LRRK2 mediated Parkinson's Disease. It is therefore an object herein to provide methods for the treatment of such diseases.

SUMMARY OF THE INVENTION

Provided herein are methods for reducing expression of LRRK2 mRNA, and optionally reducing the amount of LRRK2 protein, in an animal. In certain embodiments, the animal has Parkinson's Disease. In certain embodiments, the animal has non-LRRK2 mediated Parkinson's Disease. In certain embodiments, compounds useful for reducing expression of LRRK2 mRNA are oligomeric compounds. In certain embodiments, the oligomeric compound comprises a modified oligonucleotide.

In certain embodiments, LRRK2 mRNA expression is reduced in a cell or tissues. In certain embodiments, the cell or tissue is in an animal. In certain embodiments, the animal has Parkinson's Disease. In certain embodiments, the animal has non-LRRK2 mediated Parkinson's Disease.

Also provided are methods useful for ameliorating at least one symptom of Parkinson's Disease. In certain embodiments, symptoms are loss of motor function, aggregate formation, and neuron death.

DETAILED DESCRIPTION OF THE INVENTION

It is to be understood that both the foregoing general description and the following detailed description are exemplary and explanatory only and are not restrictive. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Where permitted, all patents, applications, published applications and other publications and other data referred to throughout in the disclosure are incorporated by reference herein in their entirety.

Unless otherwise indicated, the following terms have the following meanings:

Definitions

"Administering" means providing a pharmaceutical agent to an animal. "Administered prior to the detection of the at least one symptom" is prophylactic administration and means providing the pharmaceutical agent to an animal before a symptom of Parkinson's disease is apparent through observation or clinical diagnosis.

"Animal" means a human or non-human animal.

"Antisense activity" means any detectable and/or measurable change attributable to the hybridization of an oligomeric compound to its target nucleic acid. In certain embodiments, antisense activity is a decrease in the amount or expression of a target nucleic acid or protein encoded by such target nucleic acid compared to target nucleic acid levels or target protein levels in the absence of the oligomeric compound. In certain embodiments, antisense activity is a change in splicing of a pre-mRNA nucleic acid target. In certain embodiments, antisense activity is an increase in the amount or expression of a target nucleic acid or protein encoded by such target nucleic acid compared to target nucleic acid levels or target protein levels in the absence of the oligomeric compound.

"Ameliorate" or "amelioration" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom. In certain embodiments, the symptom is loss of motor function, aggregate formation, or neuron death. In certain embodiments, amelioration of these symptoms results in improved motor function, reduced aggregate formation, and or preservation of neurons.

"Bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Complementary" in reference to an oligonucleotide means that at least 70% of the nucleobases of the oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases means nucleobases that are capable of forming hydrogen bonds with one another. Complementary nucleobase pairs include, but unless otherwise specific are not limited to, adenine (A) and thymine (T), adenine (A) and uracil (U), cytosine (C) and guanine (G), 5-methyl cytosine ($^m$C) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that oligonucleotides are complementary to another oligonucleotide or nucleic acid at each nucleoside of the oligonucleotide.

"Conjugate group" means a group of atoms that is directly or indirectly attached to an oligonucleotide. Conjugate groups include a conjugate moiety and a conjugate linker that attaches the conjugate moiety to the oligonucleotide.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Duplex" means two oligomeric compounds that are paired. In certain embodiments, the two oligomeric compounds are paired via hybridization of complementary nucleobases.

"Gapmer" means an oligomeric compound comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"Internucleoside linkage" means a group or bond that forms a covalent linkage between adjacent nucleosides in an oligonucleotide. As used herein "modified internucleoside linkage" means any internucleoside linkage other than a naturally occurring, phosphate internucleoside linkage ("phosphodiester internucleoside linkage"). Non-phosphate linkages are referred to herein as modified internucleoside linkages. "Phosphorothioate linkage" means a modified phosphate linkage in which one of the non-bridging oxygen atoms is replaced with a sulfur atom. A phosphorothioate internucleoside linkage is a modified internucleoside linkage.

"MOE" means methoxyethyl. "2'-MOE" means a —OCH$_2$CH$_2$OCH$_3$ group at the 2' position of a furanosyl ring.

"Non-bicyclic sugar moiety" means a modified sugar moiety that comprises a modification, such as a substitutent, that does not form a bridge between two atoms of the sugar to form a second ring.

"Non-LRRK2 mediated Parkinson's Disease" is a diagnosis of Parkinson's disease not associated with a causative LRRK2 genetic mutation. Causitive LRRK2 genetic mutations include G2019S, R1441C, R1441G, I2020T, and Y1699C. Diagnosis of Parkinson's disease may be accomplished by any method including evaluating an individual's medical history, observation of signs and symptoms, and standard clinical tests or assessments. Genetic testing for a mutation associated with LRRK2, such as G2019S, R1441C, R1441G, I2020T, and Y1699C, may reveal whether an individual has non-LRRK2 mediated Parkinson's disease. An individual having a diagnosis of Parkinson's disease, but without a causative LRRK2 mutation, has non-LRRK2 mediated Parkinson's disease. "Identifying an animal having non-LRRK2 mediated Parkinson's Disease" means identifying an animal having been diagnosed with Parkinson's Disease or predisposed to develop Parkinson's Disease without a causative LRRK2 mutation.

"Nucleobase" means an unmodified nucleobase or a modified nucleobase. As used herein "an "unmodified nucleobase" is adenine (A), thymine (T), cytosine (C), uracil (U), and guanine (G). As used herein, a "modified nucleobase" is a group of atoms other than unmodified A, T, C, U, or G capable of pairing with at least one unmodified nucleobase. A "5-methylcytosine" is a modified nucleobase. A universal base is a modified nucleobase that can pair with any one of the five unmodified nucleobases. As used herein, "nucleobase sequence" means the order of contiguous nucleobases in a nucleic acid or oligonucleotide independent of any sugar or internucleoside linkage modification.

"Nucleoside" means a compound comprising a nucleobase and a sugar moiety. The nucleobase and sugar moiety are each, independently, unmodified or modified. As used herein, "modified nucleoside" means a nucleoside comprising a modified nucleobase and/or a modified sugar moiety. Modified nucleosides include abasic nucleosides, which lack a nucleobase. "Linked nucleosides" are nucleosides that are connected in a continuous sequence (i.e. no additional nucleosides are present between those that are linked).

"Oligomeric compound" means a compound comprising an oligonucleotide and optionally one or more additional features, such as a conjugate group or terminal group.

"Oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

"Parkinson's Disease" is a progressive neurodegenerative disease that affects nerve cells in the brain, primarily the substantia nigra. "At least one symptom of Parkinson's disease" includes loss of motor function, aggregate formation, or neuron death.

"Reducing or inhibiting the expression or amount" refers to a reduction or blockade of the expression or amount relative to the expression or amount in an untreated or control sample and does not necessarily indicate a total elimination of expression or amount.

"Single-stranded" in reference to an oligomeric compound means such a compound that is not paired with a second oligomeric compound to form a duplex.

"Standard cell assay" means the assay described in Example 1 and reasonable variations thereof "Standard in vivo experiment" means the procedure described in Example 2 and reasonable variations thereof.

"Sugar moiety" means an unmodified sugar moiety or a modified sugar moiety. As used herein, "unmodified sugar moiety" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. As used herein, "modified sugar moiety" means a modified furanosyl sugar moiety or a sugar surrogate. As used herein, modified furanosyl sugar moiety means a furanosyl sugar comprising a non-hydrogen substituent in place of at least one hydrogen of an unmodified sugar moiety. Modified furanosyl sugar moieties include bicyclic sugars and non-bicyclic sugars. As used herein, "sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Therapeutically effective amount" means an amount of a pharmaceutical agent that provides a therapeutic benefit to an animal. For example, a therapeutically effective amount improves a symptom of a disease.

The present disclosure provides the following non-limiting numbered embodiments:

Embodiment 1

A method comprising administering to an animal having Parkinson's disease or non-LRRK2 mediated Parkinson's disease an oligomeric compound comprising a modified oligonucleotide, wherein the modified oligonucleotide consists of 12 to 30 linked nucleosides, and wherein the modified oligonucleotide has a nucleobase sequence that is complementary to a LRRK2 nucleic acid.

Embodiment 2

A method comprising identifying an animal having Parkinson's Disease or non-LRRK2 mediated Parkinson's disease and administering to the animal having Parkinson's Disease or non-LRRK2 mediated Parkinson's disease an oligomeric compound comprising a modified oligonucleotide, wherein the modified oligonucleotide has a nucleobase sequence that is complementary to the nucleobase sequence of a LRRK2 nucleic acid.

Embodiment 3

The method of embodiment 1 or 2, wherein the modified oligonucleotide has a nucleobase sequence that is at least 90% complementary to LRRK2.

Embodiment 4

The method of embodiment 1 or 2, wherein the modified oligonucleotide has a nucleobase sequence that is at least 95% complementary to LRRK2.

Embodiment 5

The method of embodiment 1 or 2, wherein the modified oligonucleotide has a nucleobase sequence that is 100% complementary to LRRK2.

Embodiment 6

The method of embodiments 1-5 wherein the administering results in amelioration of at least one symptom of Parkinson's Disease.

Embodiment 7

The method of any of embodiments 1-6 wherein the oligomeric compound is administered prior to the detection of the at least one symptom.

Embodiment 8

The method of embodiment 6 or 7, wherein the at least one symptom of Parkinson's disease is loss of motor function, aggregate formation, or neuron death.

Embodiment 9

The method of any of embodiments 6-8, wherein the amelioration is the slowing of progression of at least one symptom.

Embodiment 10

The method of any of embodiments 6-9, wherein the amelioration is the delay of onset of at least one symptom.

Embodiment 11

The method of any of embodiments 6-10, wherein the amelioration si the reduction of severity of at least one symptom.

Embodiment 12

The method of any of embodiments 6-11, wherein the amelioration is the reduction of frequency of at least one symptom.

Embodiment 13

The method of any of embodiments 1-12, wherein expression of LRRK2 mRNA is reduced in the animal.

Embodiment 14

The method of any of embodiments 1-13, wherein expression of LRRK2 protein is reduced in the animal.

Embodiment 15

The method of any of embodiments 1-14, wherein the animal is a human.

Embodiment 16

The method of any of embodiments 1-15, wherein the nucleobase sequence of LRRK2 nucleic acid is the complement of SEQ ID NO: 2 or SEQ ID NO: 3.

Embodiment 17

The method of any of embodiments 1-16, wherein the oligomeric compound is single-stranded.

Embodiment 18

The method of any of embodiment 1-17, wherein the modified oligonucleotide comprises at least one modified nucleoside.

Embodiment 19

The method of embodiment 18, wherein the modified oligonucleotide comprises at least one modified nucleoside comprising a modified sugar moiety.

Embodiment 20

The method of embodiment 19, wherein the modified oligonucleotide comprises at least one modified nucleoside comprising a bicyclic sugar moiety.

Embodiment 21

The method of embodiment 20, wherein the modified oligonucleotide comprises at least one modified nucleoside comprising a bicyclic sugar moiety having a 2'-4' bridge, wherein the 2-4' bridge is selected from —O—CH2-; —O—CH2-CH2; and —O—CH(CH3)-.

Embodiment 22

The method of any of embodiments 18-21, wherein the modified oligonucleotide comprises at least one modified nucleoside comprising a modified non-bicyclic sugar moiety.

Embodiment 23

The method of embodiment 22, wherein the modified oligonucleotide comprises at least one modified nucleoside comprising a non-bicyclic sugar moiety comprising a 2'-MOE or 2'-OMe.

Embodiment 24

The method of any of embodiments 18-23, wherein the modified oligonucleotide comprises at least one modified nucleoside comprising a sugar surrogate.

Embodiment 25

The method of embodiment 24, wherein the modified oligonucleotide comprises at least one modified nucleoside comprising a sugar surrogate selected from a morpholino, a PNA, a F-HNA, a THP, or a modified THP.

Embodiment 26

The method of any of embodiments 1-25, wherein the modified oligonucleotide has a sugar motif comprising:
a 5'-region consisting of 1-5 linked 5'-nucleosides;
a central region consisting of 6-10 linked central region nucleosides; and
a 3'-region consisting of 1-5 linked 3'-region nucleosides;
wherein each of the 5'-region nucleosides and each of the 3'-region nucleosides comprises a modified sugar moiety and each of the central region nucleosides comprises an unmodified DNA sugar moiety.

Embodiment 27

The method of any of embodiments 1-26, wherein the modified oligonucleotide comprises at least one modified internucleoside linkage.

Embodiment 28

The method of embodiment 27, wherein each internucleoside linkage of the modified oligonucleotide is a modified internucleoside linkage.

Embodiment 29

The method of embodiment 27 or 28, wherein at least one internucleoside linkage is a phosphorothioate internucleoside linkage.

Embodiment 30

The method of embodiment 27 or 29, wherein the modified oligonucleotide comprises at least one unmodified phosphodiester internucleoside linkage.

Embodiment 31

The method of embodiment 27, wherein each internucleoside linkage is either an unmodified phosphodiester internucleoside linkage or a phosphorothioate internucleoside linkage.

Embodiment 32

The method of embodiment 28, wherein each internucleoside linkage is a phosphorothioate internucleoside linkage.

Embodiment 33

The method of any of embodiments 1-32, wherein the modified oligonucleotide comprises at least one modified nucleobase.

Embodiment 34

The method of embodiment 33, wherein the modified nucleobase is a 5-methylcytosine.

Embodiment 35

The method of any of embodiments 1-34, wherein each nucleobase of each nucleoside of the modified oligonucleotide is either an unmodified nucleobase or is a 5-methylcytosine.

Embodiment 36

The method of any of embodiments 1-35 wherein the oligomeric compound comprises a conjugate group.

Embodiment 37

The method of any of embodiments 1-16 or 18-36, wherein the oligomeric compound is paired with a second oligomeric compound to form a duplex.

Embodiment 38

The method of any preceding embodiments, wherein the animal has Parkinson's disease.

Embodiment 39

The method of any of embodiments 1-37, wherein the animal has non-LRRK2 mediated Parkinson's disease.

Embodiment 40

The method of any of embodiments 1-37, wherein the animal has LRRK2 mediated Parkinson's disease.

Embodiment 41

The method of any of embodiments 1-40, wherein the administering is to the central nervous system.

Embodiment 42

The method of any of embodiments 1-41, wherein the administering is intrathecal administration or intracerebroventricular administration.

Embodiment 43

The method of any of embodiments 1-42, wherein the administering does not cause toxicity in the periphery.

I. Certain Oligonucleotides

In certain embodiments, provided herein are oligonucleotides, which consist of linked nucleosides. Oligonucleotides may be unmodified oligonucleotides (RNA or DNA) or may be modified oligonucleotides. Modified oligonucleotides comprise at least one modification relative to unmodified RNA or DNA. That is, modified oligonucleotides comprise at least one modified nucleoside (comprising a modified sugar moiety and/or a modified nucleobase) and/or at least one modified internucleoside linkage.

A. Certain Modified Nucleosides

Modified nucleosides comprise a modified sugar moiety or a modified nucleobase or both a modified sugar moiety and a modified nucleobase.

1. Certain Sugar Moieties

In certain embodiments, modified sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2'-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.).

In certain embodiments, a 2'-substituted nucleoside or 2'-non-bicyclic modified nucleoside comprises a sugar moiety comprising a non-bridging 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a non-bridging 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a non-bridging 2'-substituent group selected from: F, OCH$_3$, and OCH$_2$CH$_2$OCH$_3$.

Nucleosides comprising modified sugar moieties, such as non-bicyclic modified sugar moieties, may be referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_2$-2', 4'-(CH$_2$)$_3$-2', 4'-CH$_2$—O-2' ("LNA"), 4'-CH$_2$—S-2', (CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., J. Org. Chem., 2009, 74, 118-134), 4'-CH$_2$—C(=CH$_2$)-2' and analogs thereof (see e.g., Seth et al., U.S. Pat. No. 8,278,426), 4'-C(R$_a$R$_b$)—N(R)—O-2', 4'—C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g. Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., Nucleic Acids Research, 1997, 25(22), 4429-4443, Albaek et al., J. Org. Chem., 2006, 71, 7731-7740, Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 20017, 129, 8362-8379; Wengel et al., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

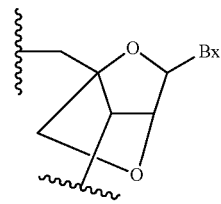

LNA (β-D-configuration)
bridge = 4'-CH$_2$——O-2'

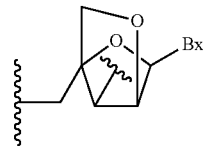

α-L-LNA (α-L-configuration)
bridge = 4'-CH$_2$——O-2'

α-L-methyleneoxy (4'-CH$_2$—O-2') or α-L-LNA bicyclic nucleosides have been incorporated into antisense oligonucleotides that showed antisense activity (Frieden et al., Nucleic Acids Research, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), manitol nucleic acid ("MNA") (see, e.g., Leumann, CJ. Bioorg. & Med. Chem. 2002, 10, 841-854), fluoro HNA:

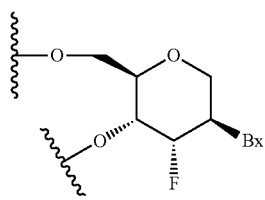

F-HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), and nucleosides comprising additional modified THP compounds having the formula:

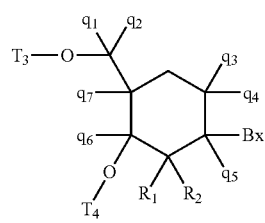

wherein, independently, for each of said modified THP nucleoside:

Bx is a nucleobase moiety;

$T_3$ and $T_4$ are each, independently, an internucleoside linking group linking the modified THP nucleoside to the remainder of an oligonucleotide or one of $T_3$ and $T_4$ is an internucleoside linking group linking the modified THP nucleoside to the remainder of an oligonucleotide and the other of $T_3$ and $T_4$ is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

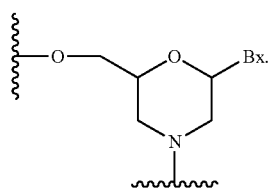

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides).

2. Certain Modified Nucleobases

In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (—C≡C—CH$_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering*, Kroschwitz, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443.

Publications that teach the preparation of certain of the above noted modified nucleobases as well as other modified nucleobases include without limitation, Manohara et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

3. Certain Modified Internucleoside Linkages

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P=O") (also referred to as unmodified or naturally occurring linkages), phosphotriesters, methylphosphonates, phosphoramidates, and phosphorothioates ("P=S"), and phosphorodithioates ("HS-P=S"). Representative non-phosphorus containing internucleoside linking groups include but are not limited to methylenemethylimino (—CH$_2$—N(CH$_3$)—O—CH$_2$—), thiodiester, thionocarbamate (—O—C(=O)(NH)—S—); siloxane (—O—SiH$_2$—O—); and N,N'-dimethylhydrazine (—CH$_2$—N(CH$_3$)—N(CH$_3$)—). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), methoxypropyl, and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

B. Certain Motifs

In certain embodiments, modified oligonucleotides comprise one or more modified nucleoside comprising a modified sugar moiety. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, each nucleoside of each wing of a gapmer is a modified nucleoside.

In certain embodiments, the gap of a gapmer comprises 7-12 nucleosides. In certain embodiments, each nucleoside of the gap of a gapmer is an unmodified 2'-deoxy nucleoside.

In certain embodiments, the gapmer is a deoxy gapmer. In embodiments, the nucleosides on the gap side of each wing/gap junction are unmodified 2'-deoxy nucleosides and the nucleosides on the wing sides of each wing/gap junction are modified nucleosides. In certain embodiments, each nucleoside of the gap is an unmodified 2'-deoxy nucleoside. In certain embodiments, each nucleoside of each wing of a gapmer is a modified nucleoside.

In certain embodiments, modified oligonucleotides comprise or consist of a region having a fully modified sugar motif. In such embodiments, each nucleoside of the fully modified region of the modified oligonucleotide comprises a modified sugar moiety. In certain embodiments, each nucleoside of the entire modified oligonucleotide comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, oligonucleotides comprise modified and/or unmodified internucleoside linkages arranged along the oligonucleotide or region thereof in a defined pattern or motif. In certain embodiments, each internucleoside linking group is a phosphate internucleoside linkage (P═O). In certain embodiments, each internucleoside linking group of a modified oligonucleotide is a phosphorothioate (P═S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

C. Certain Lengths

It is possible to increase or decrease the length of an oligonuclotides without eliminating activity. For example, in Woolf et al. (Proc. Natl. Acad. Sci. USA 89:7305-7309, 1992), a series of oligonucleotides 13-25 nucleobases in length were tested for their ability to induce cleavage of a target RNA in an oocyte injection model. Oligonucleotides 25 nucleobases in length with 8 or 11 mismatch bases near the ends of the oligonucleotides were able to direct specific cleavage of the target mRNA, albeit to a lesser extent than the oligonucleotides that contained no mismatches. Similarly, target specific cleavage was achieved using 13 nucleobase oligonucleotides, including those with 1 or 3 mismatches.

In certain embodiments, oligonucleotides (including modified oligonucleotides) can have any of a variety of ranges of lengths. In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides D. Certain Modified Oligonucleotides In certain embodiments, the above modifications (sugar, nucleobase, internucleoside linkage) are incorporated into a modified oligonucleotide. In certain embodiments, modified oligonucleotides are characterized by their modification motifs and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such sugar gapmer oligonucleotides may comprise one or more modified nucleobase independent of the gapmer pattern of the sugar modifications. Unless otherwise indicated, all modifications are independent of nucleobase sequence.

E. Nucleobase Sequence

In certain embodiments, oligonucleotides (unmodified or modified oligonucleotides) are further described by their nucleobase sequence. In certain embodiments oligonucleotides have a nucleobase sequence that is complementary to a second oligonucleotide or an identified reference nucleic acid, such as a target nucleic acid. In certain such embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 50%, at least 60%, at least 70%, at least 80%, at least 90%, at least 95%, or 100% complementary to the second oligonucleotide or nucleic acid, such as a target nucleic acid.

II. Certain Oligomeric Compounds

In certain embodiments, the invention provides oligomeric compounds, which consist of an oligonucleotide (modified or unmodified) and optionally one or more conjugate groups and/or terminal groups. Conjugate groups consist of one or more conjugate moiety and a conjugate linker which links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide. Certain conjugate groups and conjugate moieties have been described previously, for example: cholesterol moiety (Letsinger et al., *Proc. Natl. Acad. Sci. USA*, 1989, 86, 6553-6556), cholic acid (Manoharan et al., *Bioorg. Med. Chem. Lett.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Lett.*, 1993, 3, 2765-2770), a thiocholesterol (Oberhauser et al., *Nucl. Acids Res.*, 1992, 20, 533-538), an aliphatic chain, e.g., do-decan-diol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid a palmityl moiety (Mishra et al., *Biochim. Biophys. Acta*, 1995, 1264, 229-237), an octadecylamine or hexylamino-carbonyl-oxycholesterol moiety (Crooke et al., *J. Pharmacol. Exp. Ther.*, 1996, 277, 923-937), a tocopherol group (Nishina et al., *Molecular Therapy Nucleic Acids*, 2015, 4, e220; and Nishina et al., *Molecular Therapy*, 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, the conjugate linker is a single chemical bond (i.e., the conjugate moiety is attached directly to an oligonucleotide through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to parent compounds, such as the oligonucleotides provided herein. In general, a bifunctional linking moiety comprises at least two functional groups. One of the functional groups is selected to bind to a particular site on a parent compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, conjugate linkers comprise 2-5 linker-nucleosides. In certain embodiments, conjugate linkers comprise exactly 3 linker-nucleosides. In certain embodiments, conjugate linkers comprise the TCA motif. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such an oligomeric compound is more than 30. Alternatively, an oligomeric compound may comprise a modified oligonucleotide consisting of 8-30 nucleosides and no conjugate group. The total number of contiguous linked nucleosides in such an oligomeric compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the oligomeric compound has been taken up, it is desirable that the conjugate group be cleaved to release the unconjugated or parent oligonucleotide. Thus, certain conjugate linkers may comprise one or more cleavable moieties. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate linkage between an oligonucleotide and a conjugate moiety or conjugate group.

In certain embodiments, a cleavable moiety comprises or consists of one or more linker-nucleosides. In certain such embodiments, the one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is 2'-deoxy nucleoside that is attached to either the 3' or 5'-terminal nucleoside of an oligonucleotide by a phosphate internucleoside linkage and covalently attached to the remainder of the conjugate linker or conjugate moiety by a phosphate or phosphorothioate linkage. In certain such embodiments, the cleavable moiety is 2'-deoxyadenosine.

III. Duplexed Oligomeric Compounds

In certain embodiments, oligomeric compounds described herein comprise an oligonucleotide, having a nucleobase sequence complementary to that of a target nucleic acid. Oligomeric compounds are single-strands and in certain embodiments, oligomeric compounds are single-stranded. In certain embodiments, a single-stranded oligomeric compound comprises or consists of a modified oligonucleotide and optionally a conjugate group. In certain embodiments, an oligomeric compound is paired with a second oligomeric compound to form a duplex. Such duplexed oligomeric compounds comprise a first oligomeric compound having a region complementary to a target nucleic acid and a second oligomeric compound having a region complementary to the first oligomeric compound. In certain embodiments, the first oligomeric compound of a duplexed oligomeric compound comprises or consists of (1) a modified or unmodified oligonucleotide and optionally a conjugate group and (2) a second modified or unmodified oligonucleotide and optionally a conjugate group. Either or both oligomeric compounds of a duplexed oligomeric compound may comprise a conjugate group. The oligonucleotides of duplexed oligomeric compounds may include non-complementary overhanging nucleosides.

IV. Antisense Activity

In certain embodiments, oligomeric compounds are capable of hybridizing to a target nucleic acid, resulting in at least one antisense activity. In certain embodiments, oligomeric compounds selectively affect one or more target nucleic acid. Such selective oligomeric compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in significant undesired antisense activity.

In certain antisense activities, hybridization of an oligomeric compound to a target nucleic acid results in recruitment of a protein that cleaves the target nucleic acid. For example, certain oligomeric compounds result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, described herein are oligomeric compounds that are sufficiently "DNA-like" to elicit RNase H activity. In certain embodiments, one or more non-DNA-like nucleoside in the gap of a gapmer is tolerated.

In certain antisense activities, an oligomeric compound or a portion of an oligomeric compound is loaded into an RNA-induced silencing complex (RISC), ultimately resulting in cleavage of the target nucleic acid. For example, certain oligomeric compounds result in cleavage of the target nucleic acid by Argonaute. Oligomeric compounds that are loaded into RISC are RNAi compounds. RNAi compounds may be double-stranded (siRNA) or single-stranded (ssRNA).

In certain embodiments, hybridization of an oligomeric compound to a target nucleic acid does not result in recruitment of a protein that cleaves that target nucleic acid. In certain embodiments, hybridization of the oligomeric compound to the target nucleic acid results in alteration of splicing of the target nucleic acid. In certain embodiments, hybridization of an oligomeric compound to a target nucleic acid results in inhibition of a binding interaction between the target nucleic acid and a protein or other nucleic acid. In certain embodiments, hybridization of an oligomeric compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

V. Certain Target Nucleic Acids

In certain embodiments, oligomeric compounds comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target nucleic acid is a non-coding RNA associated with splicing of other pre-mRNAs. In certain embodiments, the target nucleic acid is a nuclear-retained non-coding RNA.

In certain embodiments, oligonucleotides described herein are complementary to a target nucleic acid comprising a single-nucleotide polymorphism (SNP). In certain such embodiments, the oligonucleotide is capable of modulating expression of one allele of the SNP-containing target nucleic acid to a greater or lesser extent than it modulates another allele. In certain embodiments, an oligonucleotide hybridizes to a (SNP)-containing target nucleic acid at the single-nucleotide polymorphism site.

In certain embodiments, oligonucleotides are at least partially complementary to more than one target nucleic acid. For example, oligonucleotides described herein may mimic microRNAs, which typically bind to multiple targets.

A. Complementarity/Mismatches to the Target Nucleic Acid

It is possible to introduce mismatch bases without eliminating activity. For example, Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo. Maher and Dolnick (Nuc. Acid. Res. 16:3341-3358, 1988) tested a series of tandem 14 nucleobase oligonucleotides, and a 28 and 42 nucleobase oligonucleotides comprised of the sequence of two or three of the tandem oligonucleotides, respectively, for their ability to arrest translation of human DHFR in a rabbit reticulocyte assay. Each of the three 14 nucleobase oligonucleotides alone was able to inhibit translation, albeit at a more modest level than the 28 or 42 nucleobase oligonucleotides.

In certain embodiments, oligomeric compounds comprise oligonucleotides that are complementary to the target nucleic acid over the entire length of the oligonucleotide. In certain embodiments, oligonucleotides are 99%, 95%, 90%, 85%, or 80% complementary to the target nucleic acid. In certain embodiments, oligonucleotides are at least 80% complementary to the target nucleic acid over the entire length of the oligonucleotide and comprise a region that is 100% or fully complementary to a target nucleic acid. In certain embodiments, the region of full complementarity is from 6 to 20, 10 to 18, or 18 to 20 nucleobases in length.

In certain embodiments, oligonucleotides comprise one or more mismatched nucleobases relative to the target nucleic acid. In certain embodiments, antisense activity against the target is reduced by such mismatch, but activity against a non-target is reduced by a greater amount. Thus, in certain embodiments selectivity of the oligomeric compound comprising an oligonucleotide is improved. In certain embodiments, the mismatch is specifically positioned within an oligonucleotide having a gapmer motif. In certain embodiments, the mismatch is at position 1, 2, 3, 4, 5, 6, 7, or 8 from the 5'-end of the gap region. In certain embodiments, the mismatch is at position 9, 8, 7, 6, 5, 4, 3, 2, 1 from the 3'-end of the gap region. In certain embodiments, the mismatch is at position 1, 2, 3, or 4 from the 5'-end of the wing region. In certain embodiments, the mismatch is at position 4, 3, 2, or 1 from the 3'-end of the wing region.

B. LRRK2

In certain embodiments, oligomeric compounds comprise or consist of any oligonucleotide comprising a region that is complementary to a target nucleic acid, wherein the target nucleic acid is LRRK2. In certain embodiments, LRRK2 nucleic acid has the sequence set forth in GENBANK Accession No: NT_029419.11 truncated from nucleotides 2759000 to U.S. Pat. No. 2,909,000 (incorporated herein as SEQ ID NO: 2) and GENBANK Accession No: NM_198578.3 (incorporated herein as SEQ ID NO: 3).

In certain embodiments, contacting a cell with an oligonucleotide complementary to SEQ ID NO: 2 or SEQ ID NO: 3 reduces the amount of LRRK2 mRNA, and optionally reduces the amount of LRRK2 protein. In certain embodiments, contacting a cell with an oligomeric compound complementary to SEQ ID NO: 2 or SEQ ID NO: 3 ameliroates one or more symptoms of Parkinson's disease. In certain embodiments, the symptom is loss of motor function, aggregate formation, and neuron death. In certain embodiments, contacting a cell with an oligonucleotide complementary to SEQ ID NO: 2 or SEQ ID NO: 3 improves motor function, reduces aggregate formation, and or preserves neurons.

C. Certain Target Nucleic Acids in Certain Tissues

In certain embodiments, oligomeric compounds comprise or consist of an oligonucleotide comprising a region that is complementary to a target nucleic acid, wherein the target nucleic acid is expressed in CNS tissue, including brain tissue, such as substantia nigra.

VI. Certain Pharmaceutical Compositions

In certain embodiments, described herein are pharmaceutical compositions comprising one or more oligomeric compound or a salt thereof. In certain embodiments, the pharmaceutical composition comprises a pharmaceutically acceptable diluent or carrier. In certain embodiments, a pharmaceutical composition comprises a sterile saline solution and one or more oligomeric compound. In certain embodiments, a pharmaceutical composition consists of a sterile saline solution and one or more oligomeric compound. In certain embodiments, the sterile saline is pharmaceutical grade saline. In certain embodiments, a pharmaceutical composition comprises one or more oligomeric compound and sterile water. In certain embodiments, a pharmaceutical composition consists of one oligomeric compound and sterile water. In certain embodiments, the sterile water is pharmaceutical grade water. In certain embodiments, a pharmaceutical composition comprises one or more oligomeric compound and phosphate-buffered saline (PBS). In certain embodiments, a pharmaceutical composition consists of one or more oligomeric compound and sterile PBS. In certain embodiments, the sterile PBS is pharmaceutical grade PBS.

In certain embodiments, pharmaceutical compositions comprise one or more or oligomeric compound and one or more excipients. In certain embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, oligomeric compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

In certain embodiments, pharmaceutical compositions comprising an oligomeric compound encompass any pharmaceutically acceptable salts of the oligomeric compound, esters of the oligomeric compound, or salts of such esters. In certain embodiments, pharmaceutical compositions comprising oligomeric compounds comprising one or more oligonucleotide, upon administration to an animal, including a human, are capable of providing (directly or indirectly) the biologically active metabolite or residue thereof. Accordingly, for example, the disclosure is also drawn to pharmaceutically acceptable salts of oligomeric compounds, prodrugs, pharmaceutically acceptable salts of such prodrugs, and other bioequivalents. Suitable pharmaceutically acceptable salts include, but are not limited to, sodium and potassium salts. In certain embodiments, prodrugs comprise one or more conjugate group attached to an oligonucleotide, wherein the conjugate group is cleaved by endogenous nucleases within the body.

Lipid moieties have been used in nucleic acid therapies in a variety of methods. In certain such methods, the nucleic acid, such as an oligomeric compound, is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions comprise a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, pharmaceutical compositions comprise one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, pharmaceutical compositions comprise a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, pharmaceutical compositions are prepared for oral administration. In certain embodiments, pharmaceutical compositions are prepared for buccal administration. In certain embodiments, a pharmaceutical composition is prepared for administration by injection (e.g., intravenous, subcutaneous, intramuscular, intrathecal, intracerebroventricular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

NONLIMITING DISCLOSURE AND INCORPORATION BY REFERENCE

Each of the literature and patent publications listed herein is incorporated by reference in its entirety. While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH in place of one 2'-H of DNA) or as an RNA having a modified base (thymine (methylated uracil) in place of a uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^m$CGAUCG," wherein $^m$C indicates a cytosine base comprising a methyl group at the 5-position.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or β such as for sugar anomers, or as (D) or (L), such as for amino acids, etc. Included in the compounds provided herein are all such possible isomers, including their racemic and optically pure forms, unless specified otherwise. Likewise, all cis- and trans-isomers and tautomeric forms are also included unless otherwise indicated. Unless otherwise indicated, compounds described herein are intended to include corresponding salt forms.

EXAMPLES

The following examples illustrate certain embodiments of the present disclosure and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif. And, for example, where a particular high-affinity modification appears at a particular position, other high-affinity modifications at the same position are considered suitable, unless otherwise indicated.

Example 1: In Vitro Inhibition of Murine LRRK2 mRNA

Modified oligonucleotides targeted to a murine Leucine-Rich Repeat Kinase 2 (LRRK2) nucleic acid were tested for their effects on LRRK2 mRNA in vitro. bEND cells cultured at a density of 4,000 cells per well were transfected using Cytofectin reagent with 70 nM modified oligonucleotide. After a treatment period of approximately 24 hours, RNA was isolated from the cells and mouse LRRK2 mRNA levels were measured by quantitative real-time PCR using the murine primer probe set RTS3043 (forward sequence GGCGAGTTATCCGCACCAT, designated herein as SEQ ID NO: 11; reverse sequence CCAAAACCAGCATGACATTCTTAA, designated herein as SEQ ID NO: 12; probe sequence TGAGAGCCATGGCCACAGCACAA, designated herein as SEQ ID NO: 13). LRRK2 mRNA levels were adjusted according to total RNA content, as measured by RIBOGREEN. Results are shown in the table below as percent inhibition of LRRK2, relative to untreated control cells.

The oligonucleotides in the table below are 5-10-5 MOE gapmers. The gapmers are 20 nucleotides in length, wherein the central gap segment has ten 2'-deoxynucleosides and is flanked on both sides (in the 5' and 3' directions) by wings with five 2'-MOE modified nucleosides each. The internucleoside linkages throughout each gapmer are phosphorothioate (P=S) linkages. All cytosine residues throughout each gapmer are 5-methylcytosines. The modified oligonucleotides listed in the table below are 100% complementary to the target, mouse LRRK2 mRNA (GENBANK Accession No. NM_025730.3), incorporated herein as SEQ ID NO: 1. "Mouse target start site" indicates the 5'-most nucleoside of SEQ ID NO: 1 to which the gapmer is complementary. "Mouse target stop site" indicates the 3'-most nucleoside of SEQ ID NO: 1 to which the gapmer is complementary.

TABLE 1

Inhibition of mouse LRRK2 mRNA levels by
gapmer modified oligonucleotides

| Oligo ID | Start Site | Stop Site | Sequence | % inhibition | SEQ ID NO |
|---|---|---|---|---|---|
| 422427 | 451 | 470 | AGTCCAACTATTGACAGGTT | 62 | 14 |
| 422439 | 2043 | 2062 | AGTGCACTAGCAGCTTGGAG | 63 | 15 |
| 422445 | 3070 | 3089 | TCCAGGTGGCTACTGAGGCA | 61 | 16 |
| 422467 | 5625 | 5644 | CAGCCAAGATCAAGTCCGGA | 61 | 17 |
| 422484 | 7166 | 7185 | CCACACCTCTACGACAGGGC | 64 | 18 |

Example 2: In Vivo Reduction of LRRK2 in Mice

Modified oligonucleotides complementary to mouse LRRK2 mRNA, shown in the table below, were synthesized and tested for their ability to modulate LRRK2 transcript levels in vivo. The oligonucleotides are 5-10-5 MOE gapmers. The gapmers are 20 nucleotides in length, wherein the central gap segment has ten 2'-deoxynucleosides and is flanked on both sides (in the 5' and 3' directions) by wings with five 2'-MOE modified nucleosides each. Each internucleoside linkage throughout each gapmer is either a phosphorothioate (P=S) linkage or a phosphorothioate (P=O) linkage. All cytosine residues throughout each gapmer are 5-methylcytosines. The oligonucleotides are 100% complementary to the target, mouse LRRK2 mRNA, SEQ ID NO: 1.

To test the ability of the oligonucleotides to inhibit LRRK2 mRNA expression in vivo, wild type Black 6 mice received a single 700 μg intracerebroventricular (ICV) injection of an oligonucleotide listed in the table below or PBS vehicle alone. Each treatment group consisted of four mice. Eight weeks after the single ICV injection, the mice were euthanized and RNA was isolated from the midbrain. RT-qPCR was performed as described in Example 1. The average results for each treatment group are presented in Table 2 below as percent inhibition of mouse LRRK2 mRNA expression, relative to the mouse LRRK2 mRNA levels in PBS treated animals.

TABLE 2

Reduction of LRRK2 with modified oligonucleotides in vivo

| Oligo ID | Inhibition of mouse LRRK2 mRNA (% PBS) |
|---|---|
| ASO A | 51.3 |
| ASO B | 70.1 |
| ASO C | 50.3 |

Example 3: Dose Dependent Reduction of LRRK2 In Vivo

The oligonucleotides listed in Example 2 were tested for dose responsive inhibition of mouse LRRK2 in wild type mice. Black 6 mice received a single ICV injection of an oligonucleotide at a dosage listed in the table below or PBS vehicle alone. Each treatment group consisted of three mice. Two weeks after the single ICV injection, the mice were euthanized and RNA was isolated from the midbrain. RT-qPCR was performed as described in Example 1. The average results for each treatment group are presented in the table below as percent inhibition of mouse LRRK2 mRNA expression, relative to the mouse LRRK2 mRNA levels in PBS treated animals. An inhibition value of 0% indicates that the average level of mouse LRRK2 mRNA in the treatment group was equal to or greater than the average level of mouse LRRK2 mRNA in the PBS treated group.

TABLE 4

Reduction of LRRK2 with modified oligonucleotides in vivo

| Oligo ID | Dose (μg) | Inhibition of mouse LRRK2 mRNA (% PBS) |
|---|---|---|
| ASO A | 10 | 1.0 |
|  | 30 | 12.3 |
|  | 100 | 23.3 |
|  | 300 | 53.7 |
|  | 700 | 59.1 |
| ASO B | 10 | 0 |
|  | 30 | 0.6 |
|  | 100 | 36.6 |
|  | 300 | 52.4 |
|  | 700 | 65.7 |
| ASO C | 10 | 11.7 |
|  | 30 | 0 |
|  | 100 | 31.2 |
|  | 300 | 48.2 |
|  | 700 | 49.1 |

Example 4: Prophylactic Reduction of LRRK2 with Modified Oligonucleotides in PFF Model Wild type mice received a single ICV injection of 700 μg of an oligonucleotide listed in the table below or PBS vehicle alone. Each treatment group consisted of eleven or twelve mice. Two weeks after oligonucleotide treatment, preformed fibrils (PFFs) of α-synuclein were injected into the striatum, resulting in formation of α-synuclein aggregates in several brain regions and motor deficits, as described (see Luk et al., Science, 2012, 338, 949-953). One control group did not receive injection of PFFs. Fifty-five days after the oligonucleotide treatment, motor function was tested in a wire hang test. The results are presented in Table 5 below as the average length of time the mice of each treatment group remained on the wire.

One day after the wire hang test, all of the mice in each treatment group were sacrificed except for the group that received no oligonucleotide and no PFF injection; only four mice in that group were sacrificed. Animals were perfused with ice-cold PBS. Ipsilateral hemispheres were fixed and processed for immunochemistry. Contralateral midbrain and striatum were dissected and frozen until RNA analysis, while entire contralateral cortex was dissected and frozen until protein analysis. LRRK2 mRNA expression was analyzed by RT-qPCR as described in the examples above, and the results are shown in Table 5 below as average percent inhibition relative to the wild type control group that received neither oligonucleotide treatment nor PFF injection.

LRRK2, α-synuclein, and hyperphosphorylated α-synuclein (p-α-syn) protein levels in the cortex were analyzed by western blot. Contralateral cortex tissue was first homogenized in RIPA buffer and centrifuged at 13,300×g. The supernatant was subjected to western blot for LRRK2 protein level, and β-tubulin was used as a loading control. The results indicated that LRRK2 protein levels in the cortex were significantly lower in the oligonucleotide treated animals than in the animals that did not receive oligonucleotide treatment. The pellet was resuspended in RIPA buffer, centrifuged at 100,000×g, and the resulting insoluble material was further suspended in 2% SDS buffer, followed by an additional 100,000×g spin. The resulting supernatant was analyzed by western blot for α-synuclein and p-α-syn. The results showed that PFF injection resulted in recruitment of endogenous mouse α-synuclein into insoluble aggregates, as reported in Luk et al. The aggregates were also hyperphosphorylated. Oligonucleotide treatments reduced formation of the aggregates, as evidenced by a reduction of insoluble mouse α-synuclein and p-α-syn in the western blots. p-α-syn aggregates in the substantia nigra were visualized by immunohistochemistry. The average number of aggregates observed for samples of equal size from each treatment group is shown in Table 5 below. One-way ANOVA test of the results showed that the differences between the PBS treated and oligonucleotide treated animals were significant.

TABLE 5

Prophylactic treatment of PFF mice with LRKK2 modified oligonucleotides

| ISIS No. | PFF injected | Time in wirehang test (sec) | Inhibition of LRPK2 mRNA (%) | | No. of p-α-syn aggregates |
|---|---|---|---|---|---|
| | | | Midbrain | Striatum | |
| PBS | No | 193 | 0 | 4.0 | 0 |
| PBS | Yes | 94 | 0 | 0 | 42 |
| ASO A | Yes | 187 | 52.0 | 49.0 | 12 |
| ASO B | Yes | 175 | 43.0 | 24.8 | 21 |

Example 5: Reduction of LRRK2 with Modified Oligonucleotide in PFF Model

The effects of oligonucleotide reduction in wild type mice after the injection of PFFs was evaluated using ASO B (see Example 2). Mice were treated as described in Example 4 except that oligonucleotide treatment occurred two weeks after PFF injection instead of two weeks before PFF injection. Each treatment group consisted of ten animals. Fifty-five days after PFF injection, the mice were assessed in a wire hang test, as described in Example 4. One day after the wire hang test, the mice were sacrificed, the midbrain, striatum, and substantia nigra were collected, and LRRK2 mRNA and p-α-syn aggregates were measured, as described in Example 4. The results are shown in the table below as the averages for each treatment group. An entry of "nd" indicates that data was not collected for that treatment group. The results show that even when the modified oligonucleotide was administered after the onset of the PFF model, motor function was improved and the number of pathological aggregates was reduced.

TABLE 6

Treatment of PFF mice with LRKK2 modified oligonucleotides

| Oligo ID | PFF injected | Time in wirehang test (sec) | Inhibition of LRRK2 mRNA (%) | | No. of p-α-syn aggregates |
|---|---|---|---|---|---|
| | | | Midbrain | Striatum | |
| PBS | No | 227 | 0 | 0 | nd |
| PBS | Yes | 58 | 0 | 0 | 49 |
| ASO B | Yes | 141 | 62.3 | 43.6 | 38 |

Example 6. Prophylactic Reduction of LRRK2 with Modified Oligonucleotides in PFF Model in a Long Term Study Modified oligonucleotides were tested in a long term study to determine if long term treatment with modified oligonucleotides is protective of dopaminergic neurons. Accumulation of α-syn aggregates in the substantia nigra pars compacta compromises survival of dopaminergic neurons over time (Luk 2012, Tran 2014).

The effects of oligonucleotide reduction in wild type mice after the injection of PFFs was evaluated using ASO B (see Example 2) or control oligonucleotide 676630, a 5-10-5 MOE gapmer with mixed phosphodiester and phosphorothioate backbone with no known target. Mice were treated as described in Example 4 except mice received a second ICV dose of ASO B at 90 days, and were sacrificed at 180 days post first ICV treatment. Each treatment group consisted of 12 animals. At sacrifice, midbrain, striatum, and substantia nigra were collected, and LRRK2 mRNA and p-α-syn aggregates were measured, as described in Example 4, and dopaminergic cells were quantified by immunohistochemistry using anti-tyrosine hydroxylase (TH) antibody. The results are shown in the table below as the averages for each treatment group. The results show that in the group treated with modified oligonucleotide complementary to LRRK2, the number of pathological aggregates was reduced over a long treatment course. Additionally, quantification of TH-positive neurons showed that ASO B-mediated LRRK2 suppression rescued TH-positive cells in the ipsilateral substantia nigra pars compacta as compared to control treated mice.

TABLE 7

Prophylactic treatment of PFF mice with LRKK2 modified oligonucleotides in long term study

| Oligo ID | PFF injected | Inhibition of LRRK2 mRNA (%) | | No. of p-α-syn aggregates | No. of dopaminergic cells |
|---|---|---|---|---|---|
| | | Midbrain | Striatum | | |
| 676630 | Yes | 0 | 0 | 160 | 5880 |
| ASO B | Yes | 61.7 | 0 | 48 | 7522 |

Example 7. Effect of Central Delivery of LRRK2 Modified Oligonucleotides on Kidney and Lung LRRK2 Levels Prior studies have shown that genetic ablation of LRRK2 resulted in accumulation of autophagic vacuoles in kidney's proximal tubule epithelial cells and lung's type II pneumocytes. See, e.g., Herzig, M. C., et al., LRRK2 protein levels are determined by kinase function and are crucial for kidney and lung homeostasis in mice. Hum Mol Genet, 2011. 20(21): p. 4209-23; Hinkle, K. M., et al., LRRK2 knockout mice have an intact dopaminergic system but display alterations in exploratory and motor co-ordination behaviors. Mol Neurodegener, 2012. 7: p. 25; Tong, Y., et al., Loss of leucine-rich repeat kinase 2 causes age-dependent bi-phasic alterations of the autophagy pathway. Mol Neurodegener, 2012. 7: p. 2. Therefore, the effect of LRRK2 modified oligonucleotides administered to the central nervous systems by intracerebroventricular administration on LRRK2 levels in the kidney and lung was measured.

Wildtype C57BL/6J mice were treated with 700 μg modified oligonucleotides or PBS via intracerebroventricular administration. Tissues were harvested 56 days later. LRRK2 mRNA was measured by RT-QPCR in the cortex, midbrain, and kidney and lungs of the mice to determine if central delivery of modified oligonucleotides is specific to reducing LRRK2 in the CNS. While ASO A and ASO B significantly reduced LRRK2 mRNA in the midbrain and cortex, neither ASO A nor ASO B affected LRRK2 mRNA in the kidney or lung when injected intracerebroventricularly. Furthermore, hematoxylin and eosin histology revealed no abnormalities, ie. vacuoles in the kidney and lungs. Therefore, central delivery of ASO A and ASO B specifically targets LRRK2 in the brain without affecting systemic LRRK2 levels or causing histological abnormalities in the periphery including kidney and lungs.

TABLE 8

LRRK2 mRNA levels in cortex, midbrain, kidney, and lung compared to PBS administration after intracerebroventricular administration

| Oligo ID | Inhibition of LRRK2 mRNA (%) | | | |
|---|---|---|---|---|
| | Cortex | Midbrain | Kidney | Lung |
| ASO A | 49.5 | 51.7 | 6.8 | 13.4 |
| ASO B | 60.4 | 70.5 | 19.2 | 6.8 |

The invention claimed is:

1. A method comprising administering to an animal having non-LRRK2 mediated Parkinson's disease an oligomeric compound comprising a modified oligonucleotide, wherein the modified oligonucleotide:
 a) consists of 12 to 30 linked nucleosides;
 b) has a nucleobase sequence that is at least 90% complementary to the nucleobase sequence of SEQ ID NO: 2 or SEQ ID NO: 3; and
 c) comprises at least one modified nucleoside comprising a modified sugar moiety and/or at least one modified internucleoside linkage.

2. A method comprising identifying an animal having non-LRRK2 mediated Parkinson's disease and administering to the animal having non-LRRK2 mediated Parkinson's disease an oligomeric compound comprising a modified oligonucleotide, wherein the modified oligonucleotide:
 a) consists of 12 to 30 linked nucleosides;
 b) has a nucleobase sequence that is at least 90% complementary to the nucleobase sequence of SEQ ID NO: 2 or SEQ ID NO: 3; and
 c) comprises at least one modified nucleoside comprising a modified sugar moiety and/or at least one modified internucleoside linkage.

3. The method of claim 1, wherein the administering results in amelioration of at least one symptom of Parkinson's disease.

4. The method of claim 1, wherein the oligomeric compound is administered prior to detection of at least one symptom of Parkinson's disease.

5. The method of claim 3, wherein the at least one symptom of Parkinson's disease is loss of motor function, aggregate formation, or neuron death.

6. The method of claim 3, wherein the amelioration of at least one symptom of Parkinson's disease is the slowing of progression of at least one symptom, the delay of onset of at least one symptom, or the reduction of severity or frequency of at least one symptom.

7. The method of claim 1, wherein expression of LRRK2 mRNA and/or LRRK2 protein is reduced in the animal.

8. The method of claim 2, wherein expression of LRRK2 mRNA and/or LRRK2 protein is reduced in the animal.

9. The method of claim 1, wherein the oligomeric compound is single-stranded.

10. The method of claim 1, wherein the modified oligonucleotide comprises at least one modified nucleoside comprising a modified sugar moiety.

11. The method of claim 10, wherein the modified oligonucleotide comprises at least one modified nucleoside comprising a bicyclic sugar moiety.

12. The method of claim 11, wherein the modified oligonucleotide comprises at least one modified nucleoside comprising a bicyclic sugar moiety having a 2'-4' bridge, wherein the 2-4' bridge is selected from —O—CH$_2$—; —O—CH$_2$—CH$_2$; and —O—CH(CH$_3$)—.

13. The method of claim 1, wherein the modified oligonucleotide comprises at least one modified nucleoside comprising a modified non-bicyclic sugar moiety.

14. The method of claim 13, wherein the modified oligonucleotide comprises at least one modified nucleoside comprising a non-bicyclic sugar moiety comprising a 2'-MOE or 2'-OMe.

15. The method of claim 1, wherein the modified oligonucleotide comprises at least one modified nucleoside comprising a sugar surrogate.

16. The method of claim 15, wherein the modified oligonucleotide comprises at least one modified nucleoside comprising a sugar surrogate selected from a morpholino, a PNA, a F-HNA, a THP, or a modified THP.

17. The method of claim 1, wherein the modified oligonucleotide has a sugar motif comprising:
 a 5'-region consisting of 1-5 linked 5'-nucleosides;
 a central region consisting of 6-10 linked central region nucleosides; and
 a 3'-region consisting of 1-5 linked 3'-region nucleosides; wherein each of the 5'-region nucleosides and each of the 3'-region nucleosides comprises a modified sugar moiety and each of the central region nucleosides comprises an unmodified DNA sugar moiety.

18. The method of claim 1, wherein the modified oligonucleotide comprises at least one modified internucleoside linkage, wherein at least one modified internucleoside linkage is a phosphorothioate internucleoside linkage.

19. The method of claim 1, wherein each internucleoside linkage of the modified oligonucleotide is either an unmodified phosphodiester internucleoside linkage or a phosphorothioate internucleoside linkage.

20. The method of claim 1, wherein the modified oligonucleotide comprises at least one 5-methylcytosine.

21. The method of claim 1, wherein the oligomeric compound comprises a conjugate group.

22. The method of claim 1, wherein the oligomeric compound is paired with a second oligomeric compound to form a duplex.

23. The method of claim 1, wherein the administering is to the central nervous system.

24. The method of claim 1, wherein the administering is intrathecal administration or intracerebroventricular administration.

25. The method of claim 1, wherein the administering does not cause toxicity in the periphery.

26. The method of claim 2, wherein the administering results in amelioration of at least one symptom of Parkinson's disease.

27. The method of claim 26, wherein the at least one symptom of Parkinson's disease is loss of motor function, aggregate formation, or neuron death.

28. The method of claim 2, wherein the oligomeric compound is administered prior to detection of at least one symptom of Parkinson's disease.

29. The method of claim 26, wherein the amelioration of at least one symptom of Parkinson's disease is the slowing of progression of at least one symptom, the delay of onset of at least one symptom, or the reduction of severity or frequency of at least one symptom.

30. The method of claim 2, wherein the oligomeric compound is single-stranded.

31. The method of claim 2, wherein the modified oligonucleotide comprises at least one modified nucleoside comprising a modified sugar moiety.

32. The method of claim 31, wherein the modified oligonucleotide comprises at least one modified nucleoside comprising a bicyclic sugar moiety.

33. The method of claim 32, wherein the modified oligonucleotide comprises at least one modified nucleoside comprising a bicyclic sugar moiety having a 2'-4' bridge, wherein the 2-4' bridge is selected from —O—CH$_2$—; —O—CH$_2$—CH$_2$—; and —O—CH(CH$_3$)—.

34. The method of claim 2, wherein the modified oligonucleotide comprises at least one modified nucleoside comprising a modified non-bicyclic sugar moiety.

35. The method of claim 34, wherein the modified oligonucleotide comprises at least one modified nucleoside comprising a non-bicyclic sugar moiety comprising a 2'-MOE or 2'-OMe.

36. The method of claim 2, wherein the modified oligonucleotide comprises at least one modified nucleoside comprising a sugar surrogate.

37. The method of claim 36, wherein the modified oligonucleotide comprises at least one modified nucleoside comprising a sugar surrogate selected from a morpholino, a PNA, a F-HNA, a THP, or a modified THP.

38. The method of claim 2, wherein the modified oligonucleotide has a sugar motif comprising:
a 5'-region consisting of 1-5 linked 5'-nucleosides;
a central region consisting of 6-10 linked central region nucleosides; and
a 3'-region consisting of 1-5 linked 3'-region nucleosides;
wherein each of the 5'-region nucleosides and each of the 3'-region nucleosides comprises a modified sugar moiety and each of the central region nucleosides comprises an unmodified DNA sugar moiety.

39. The method of claim 2, wherein the modified oligonucleotide comprises at least one modified internucleoside linkage, wherein at least one modified internucleoside linkage is a phosphorothioate internucleoside linkage.

40. The method of claim 2, wherein each internucleoside linkage of the modified oligonucleotide is either an unmodified phosphodiester internucleoside linkage or a phosphorothioate internucleoside linkage.

41. The method of claim 2, wherein the modified oligonucleotide comprises at least one 5-methylcytosine.

42. The method of claim 2, wherein the oligomeric compound comprises a conjugate group.

43. The method of claim 2, wherein the oligomeric compound is paired with a second oligomeric compound to form a duplex.

44. The method of claim 2, wherein the administering is to the central nervous system.

45. The method of claim 2, wherein the administering is intrathecal administration or intracerebroventricular administration.

46. The method of claim 2, wherein the administering does not cause toxicity in the periphery.

47. The method of claim 1, wherein the modified oligonucleotide has a nucleobase sequence that is 100% complementary to the nucleobase sequence of SEQ ID NO: 2 or SEQ ID NO: 3.

48. The method of claim 2, wherein the modified oligonucleotide has a nucleobase sequence that is 100% complementary to the nucleobase sequence of SEQ ID NO: 2 or SEQ ID NO: 3.

* * * * *